(12) United States Patent
Niklason et al.

(10) Patent No.: US 9,938,503 B2
(45) Date of Patent: Apr. 10, 2018

(54) DIFFERENTIATION OF HUMAN IPS CELLS TO HUMAN ALVEOLAR TYPE II VIA DEFINITIVE ENDODERM

(71) Applicant: YALE UNIVERSITY, New Haven, CT (US)

(72) Inventors: Laura E. Niklason, Greenwich, CT (US); Mahboobe Ghaedi, New Haven, CT (US)

(73) Assignee: Yale University, New Haven, CT (US)

( * ) Notice: Subject to any disclaimer, the term of this patent is extended or adjusted under 35 U.S.C. 154(b) by 669 days.

(21) Appl. No.: 14/055,573

(22) Filed: Oct. 16, 2013

(65) Prior Publication Data

US 2014/0105870 A1 Apr. 17, 2014

Related U.S. Application Data

(63) Continuation of application No. PCT/US2013/061687, filed on Sep. 25, 2013.

(60) Provisional application No. 61/705,427, filed on Sep. 25, 2012.

(51) Int. Cl.
*C12N 5/071* (2010.01)
*A61K 35/42* (2015.01)

(52) U.S. Cl.
CPC ............ *C12N 5/0688* (2013.01); *A61K 35/42* (2013.01); *C12N 2501/11* (2013.01); *C12N 2501/115* (2013.01); *C12N 2501/117* (2013.01); *C12N 2501/119* (2013.01); *C12N 2501/16* (2013.01); *C12N 2501/415* (2013.01); *C12N 2506/45* (2013.01); *C12N 2533/50* (2013.01); *C12N 2533/52* (2013.01); *C12N 2533/54* (2013.01); *C12N 2533/70* (2013.01); *C12N 2533/90* (2013.01)

(58) Field of Classification Search
None
See application file for complete search history.

(56) References Cited

U.S. PATENT DOCUMENTS

| | | |
|---|---|---|
| 2011/0200567 A1 | 8/2011 | Wetsel et al. |
| 2012/0064050 A1 | 3/2012 | Calle et al. |
| 2012/0088300 A1 | 4/2012 | Melton et al. |
| 2012/0100115 A1 | 4/2012 | Morrison et al. |
| 2013/0217005 A1* | 8/2013 | Snoeck ................ C12N 5/0617 435/6.1 |

FOREIGN PATENT DOCUMENTS

| | | | |
|---|---|---|---|
| WO | 03046141 A2 | 6/2003 | |
| WO | 2008103810 A1 | 8/2008 | |
| WO | WO 2010/091188 | * 8/2010 | ............. C12N 5/071 |
| WO | 2011139628 A1 | 11/2011 | |

OTHER PUBLICATIONS

PCT Search Report and Written Opinion for PCT/US2013/061687 dated Dec. 23, 2013.
Alcorn, et al., "Morphological effects of chronic tracheal ligation and drainage in the fetal lamb lung", J Anat. 123(Pt 3), Jul. 1977, 649-660.
Ali, et al., "Derivation of type II alveolar epithelial cells from murine embryonic stem cells", Tissue Eng. 8(4), 2002, 541-550.
Asselin-Labat, et al., "Adult lung stem cells and their contribution to lung tumourigenesis", Open Biol. 2(8), Aug. 2012, 120094.
Badylak, et al., "Engineered whole organs and complex tissues", Lancet 379(9819, Mar. 10, 2012, 943-952.
Banerjee, et al., "Human embryonic stem cells differentiated to lung lineage-specific cells ameliorate pulmonary fibrosis in a xenograft transplant mouse model", PLoS One 7(3), 2012, e33165.
Booth, et al., "Acellular normal and fibrotic human lung matrices as a culture system for in vitro investigation", Am J Resp Crit Care Med. 186(9), Nov. 1, 2012, 866-76.
Bove, et al., "uman alveolar type II cells secrete and absorb liquid in response to local nucleotide signaling", J Biol Chem. 285(45), Nov. 5, 2010, 34939-34949.
Calle, et al., "Procedure for lung engineering", J Vis Exp. (49), Mar. 8, 2011, pii:2651.
Chapman, et al., "Integrin α6β4 identifies an adult distal lung epithelial population with regenerative potential in mice.", J Clin Invest. 121(7), Jul. 2011, 2855-2862.
Daly, et al., "Initial binding and recellularization of decellularized mouse lung scaffolds with bone marrow-derived mesenchymal stromal cells", Tissue Eng. Part A 18(1-2), Jan. 2012, 1-16.
D'Amour, et al., "Efficient differentiation of human embryonic stem cells to definitive endoderm", Nat Biotechnol. 23 (12), Dec. 2005, 1534-1541.
Duan, et al., "Differentiation and characterization of metabolically functioning hepatocytes from human embryonic stem cells", Stem Cells 28(4), Apr. 2010, 674-686.
Fehrenbach, et al., "Alveolar epithelial type II cell: defender of the alveolus revisited", Respir Res. 2(1), 2001, 33-46.
Fujino, et al., "A novel method for isolating individual cellular components from the adult human distal lung", Am J Respir Cell Mol Biol 46(4), Apr. 2012, 422-420.
Fujino, et al., "Isolation of alveolar epithelial type II progenitor cells from adult human lungs", Lab Invest 91(3), Mar. 2011, 363-378.
Green, et al., "Generation of anterior foregut endoderm from human embryonic and induced pluripotent stem cells", Nat Biotechnol 29(3), Mar. 2011, 267-272.

(Continued)

*Primary Examiner* — Taeyoon Kim
*Assistant Examiner* — Srikanth Patury
(74) *Attorney, Agent, or Firm* — Saul Ewing Arnstein & Lehr LLP; Kathryn Doyle

(57) ABSTRACT

The present invention relates to compositions and methods for generating populations of tissue precursor cells from pluripotent cells, and preferably induction of stem cells into definitive endoderm to generate anterior foregut endoderm from pluripotent cells. The anterior foregut endoderm cells can then be differentiated into an alveolar epithelial type II cell.

9 Claims, 42 Drawing Sheets

(56) References Cited

OTHER PUBLICATIONS

Gutierrez, et al., "Mechanical distension modulates pulmonary alveolar epithelial phenotypic expression in vitro", Am J Physiol. 74(2 Pt 1), Feb. 1998, L196-202.
Kadzik, et al., "Directing lung endoderm differentiation in pluripotent stem cells", Cell Stem Cell 10(4), Apr. 6, 2012, 355-361.
Kotton, et al., "Next-generation regeneration: the hope and hype of lung stem cell research", Am J Respir Crit Care Med. 185(12), Jun. 15, 2012, 1255-1260.
Kubo, et al., "Development of definitive endoderm from embryonic stem cells in culture", Development.131(7), Apr. 2004, 1651-1662.
Lin, et al., "Tissue engineering of lung: the effect of extracellular matrix on the differentiation of embryonic stem cells to pneumocytes", Tissue Eng Part A 16(5), May 2010, 1515-1526.
Longmire, et al., "Efficient derivation of purified lung and thyroid progenitors from embryonic stem cells", Cell Stem Cell 10(4), Apr. 6, 2012, 398-411.
McCurry, et al., "Lung transplantation in the United States, 1998-2007", Am J Transplant 9(Part 2), Apr. 2009, 942-958.
Mou, et al., "Generation of multipotent lung and airway progenitors from mouse ESCs and patient-specific cystic fibrosis iPSCs", Cell Stem Cell 10(4), Apr. 6, 2012, 385-397.
Nichols, et al., "Production and utilization of acellular lung scaffolds in tissue engineering", J Cell Biochem. 113(7), Jul. 2012, 2185-2192.
Nishikawa, et al., "The promise of human induced pluripotent stem cells for research and therapy", Nat Rev Mol Cell Biol 9(9), Sep. 2008, 725-729.
Ostrowski, et al., "Inhibition of ciliated cell differentiation by fluid submersion.", Expt Lung Res. 21(6), Nov.-Dec. 1995, 957-970.
Ott, et al., "Regeneration and orthotopic transplantation of a bioartificial lung", Nat Med. 16(8), Aug. 2010, 927-933.
Petersen, et al., "Bioreactor for the long-term culture of lung tissue", Cell Transplant 20(7), 2011, 1117-1126.
Petersen, et al., "Strategies for lung regeneration", Material today 14(5), May 2011, 196-201.
Petersen, et al., "Tissue-engineered lungs for in vivo implantation", Science 329(5991), Jul. 30, 2010, 538-541.
Reilly, et al., "Intrinsic extracellular matrix properties regulate stem cell differentiation", J Biomech 43(1), Jan. 5, 2010, 55-62.
Rippon, et al., "Derivation of distal lung epithelial progenitors from murine embryonic stem cells using a novel three-step differentiation protocol", Stem Cells 24(5), May 2006, 1389-1398.
Samadikuchaksaraei, et al., "Derivation of distal airway epithelium from human embryonic stem cells", Tissue Eng. 12(4), Apr. 2006, 867-875.
Schmiedl, et al., "Distribution of surfactant proteins in type II pneumocytes of newborn, 14-day old, and adult rats: an immunoelectron microscopic and stereological study", Histochem Cell Biol. 124(6), Dec. 2005, 465-476.
Soh, et al., "CD166(pos) subpopulation from differentiated human ES and iPS cells support repair of acute lung injury", Mol Ther. 20(12), Dec. 2012, 2335-2346.
Takahashi, et al., "Induction of pluripotent stem cells from adult human fibroblasts by defined factors", Cell 131(5), Nov. 30, 2007, 861-872.
Tesei, et al., "Isolation of stem/progenitor cells from normal lung tissue of adult humans", Cell Prolif. 42(3), Jun. 2009, 298-308.
Van Haute, et al., "Generation of lung epithelial-like tissue from human embryonic stem cells", Respir Res. 10, Nov. 5, 2009, 105.
Wang, et al., "A pure population of lung alveolar epithelial type II cells derived from human embryonic stem cells", Proc Natl Acad Sci U S A. 104(11), Mar. 13, 2007, 4449-4454.
Whitsett, et al., "Integrin $\alpha 6\beta 4$ defines a novel lung epithelial progenitor cell: a step forward for cell-based therapies for pulmonary disease", J Clin Invest. 121(7), Jul. 2011, 2543-2545.
Yasunaga, et al., "Induction and monitoring of definitive and visceral endoderm differentiation of mouse ES cells", Nat Biotechnol. 23(12), Dec. 2005, 1542-1550.
Yu, et al., "Induced pluripotent stem cell lines derived from human somatic cells", Science 318(5858), Dec. 21, 2007, 1917-1920.
Ghaedi, et al., "Human iPS cell-derived alveolar epithelium repopulates lung extracellular matrix", The Journal of Clinical Investigation 123(11), Nov. 2013, 4950-4962.
Wu, et al., "Isolation and characterization of human alveolar type II cells and phenotypes maintaining study", Wei Zhong Bing Ji Jiu Yi Xue-Chinese Critical Care Medicine. 24(7), Jul. 2012, 388-392 (English Abstract Only).
Extended European Search Report for European Patent Application No. 13842781.0 dated Jun. 21, 2016.

* cited by examiner

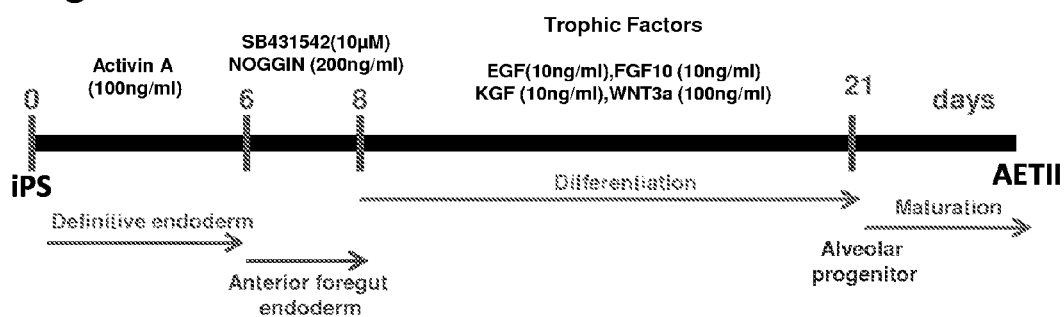

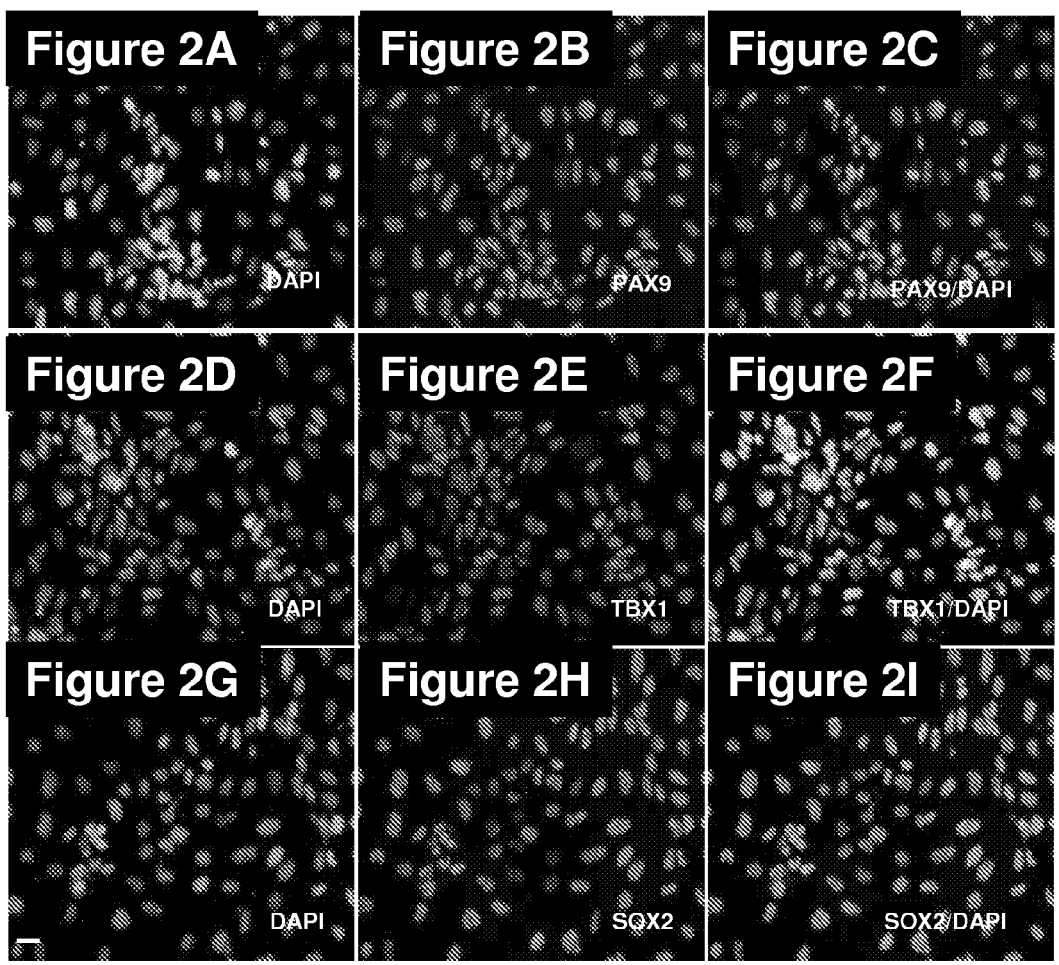

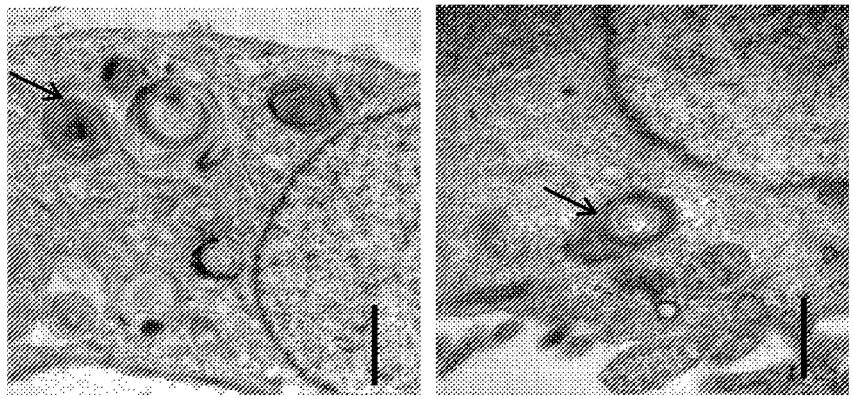
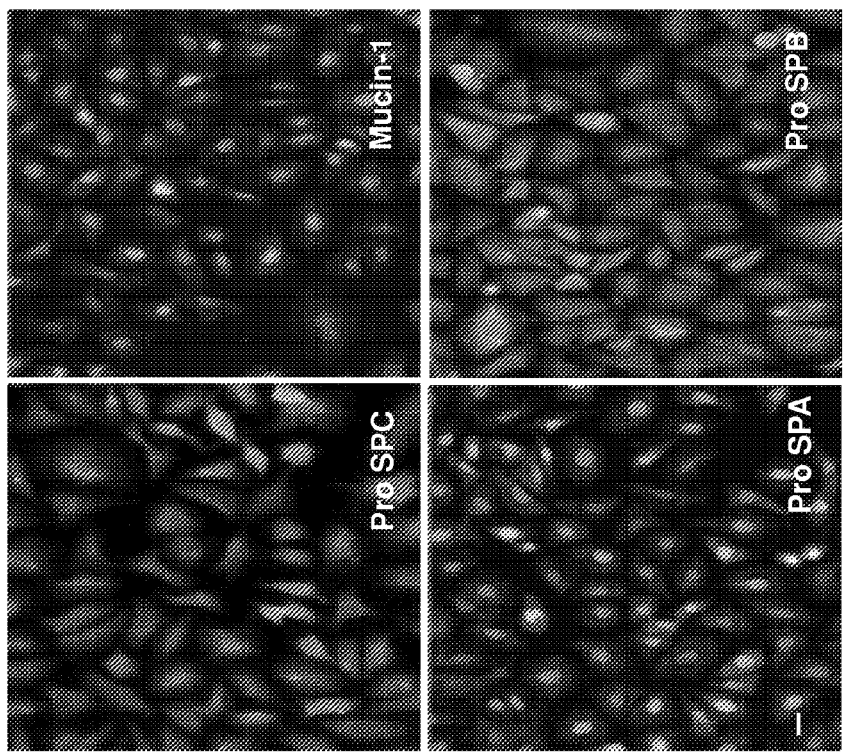

Figure 3I
Figure 3J
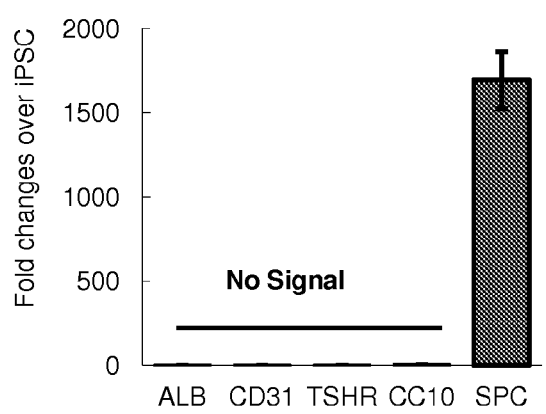
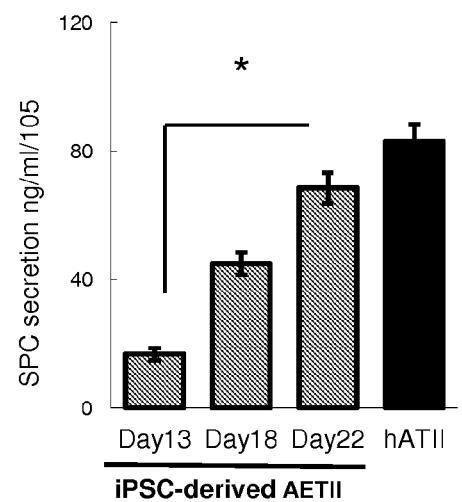
Figure 3K
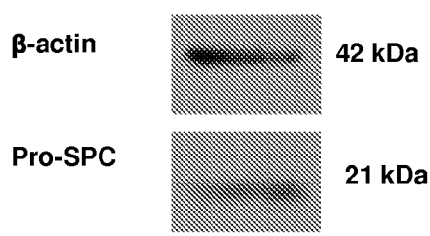

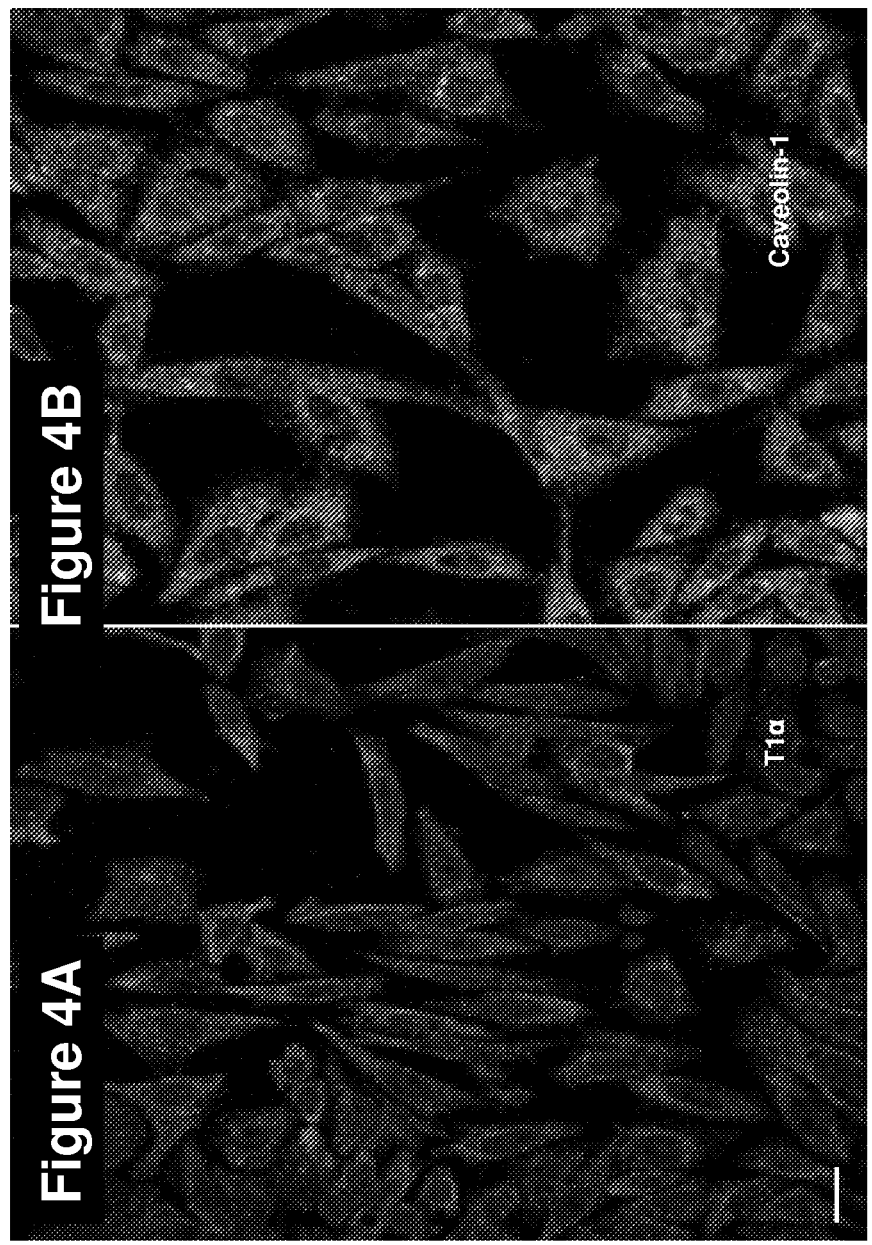

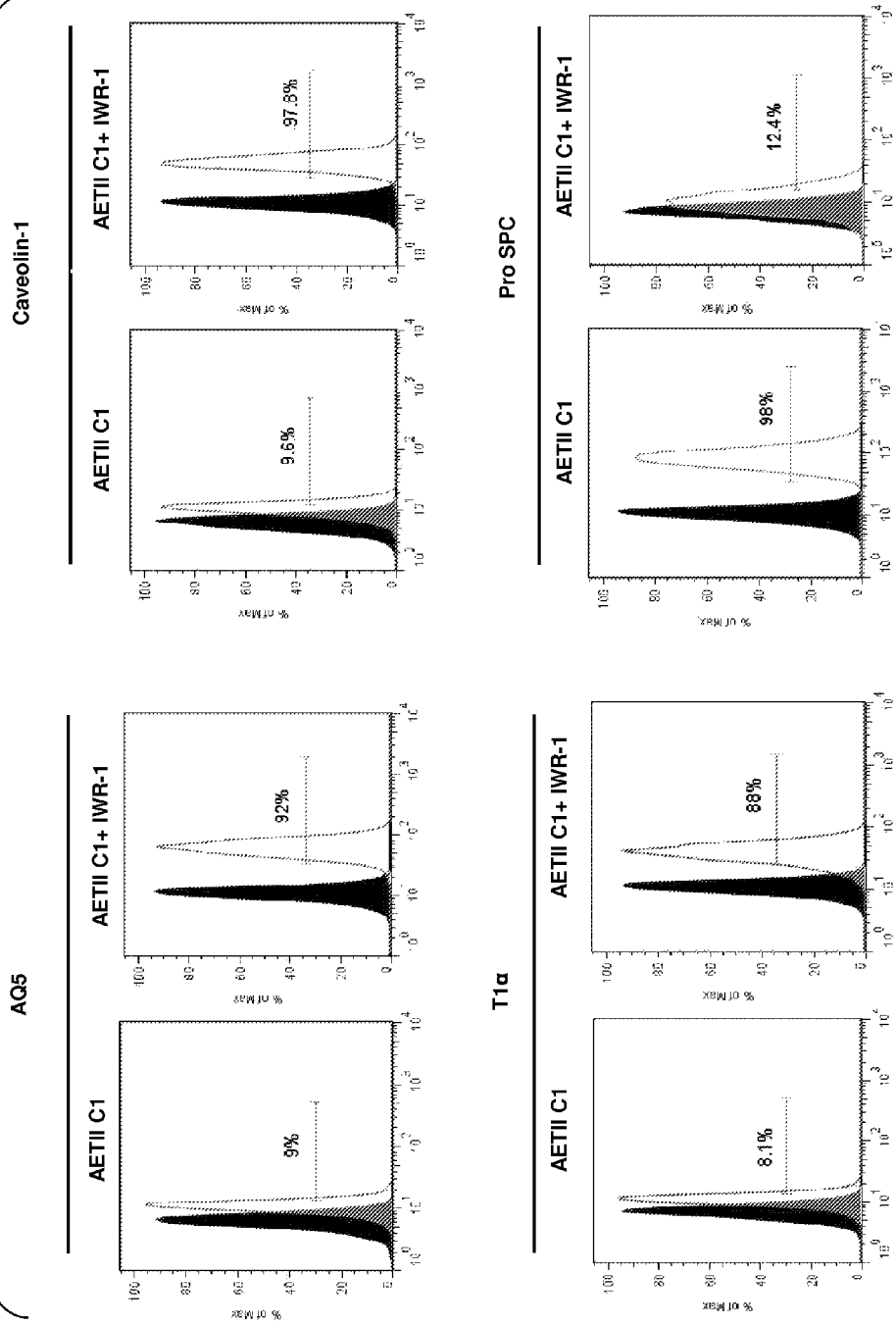

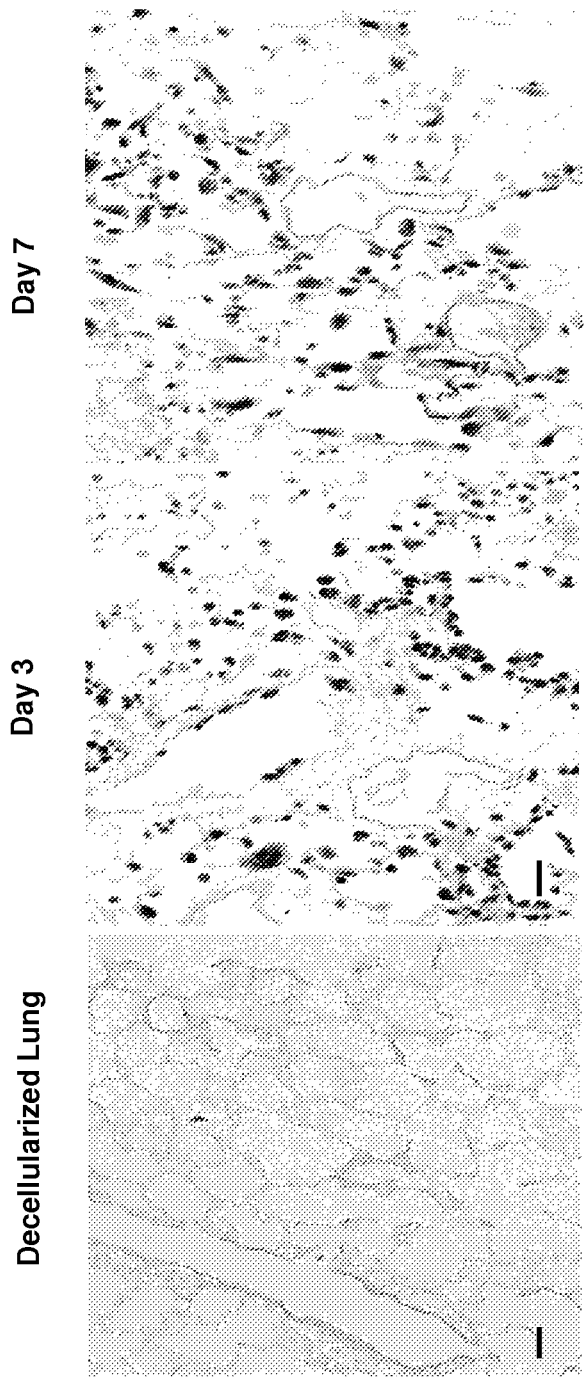

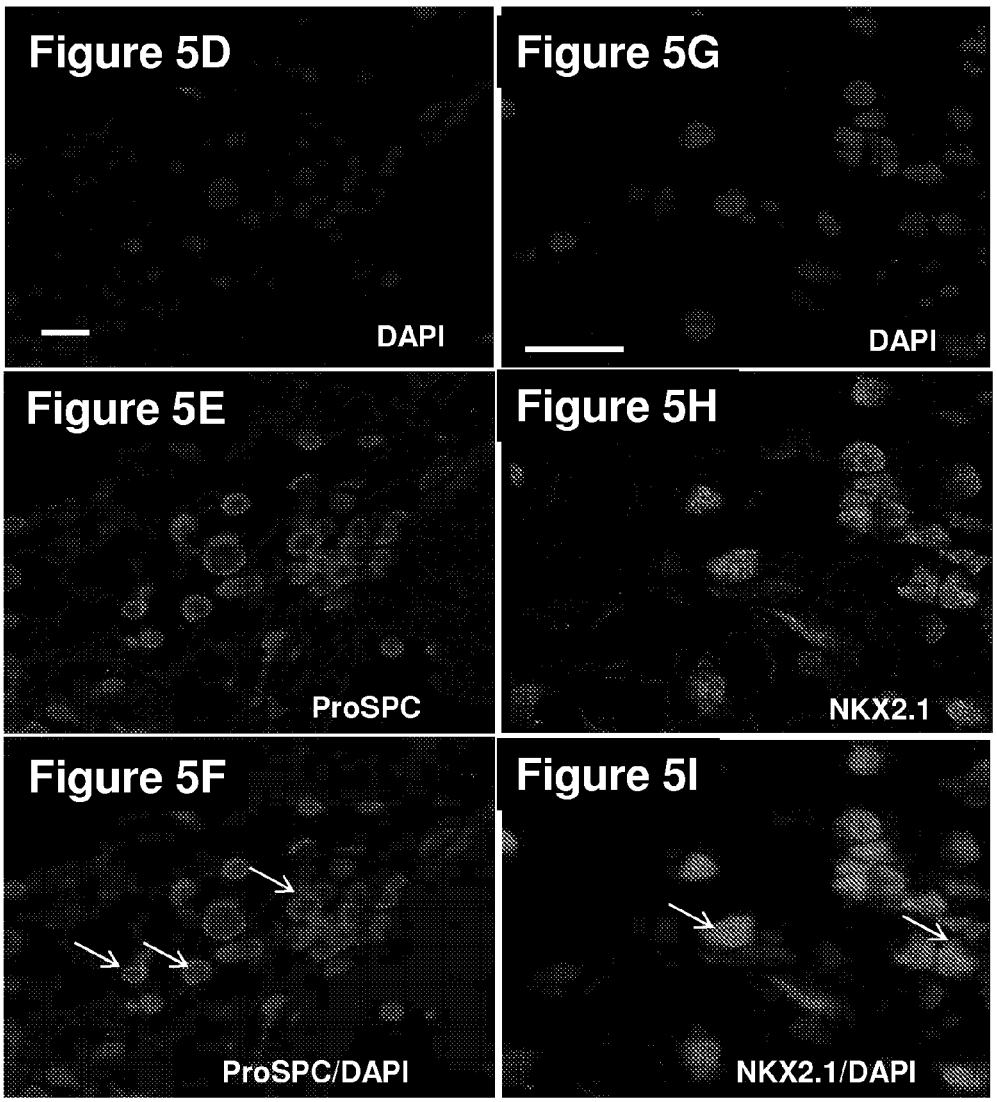

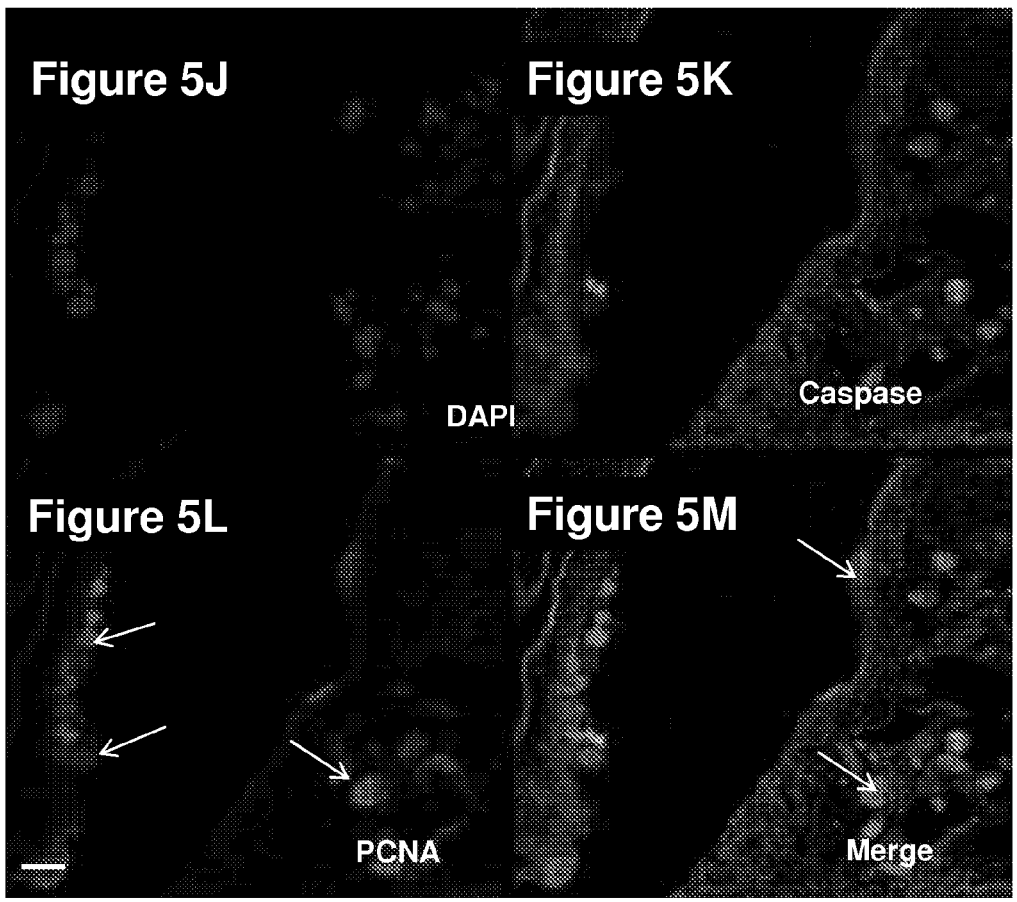
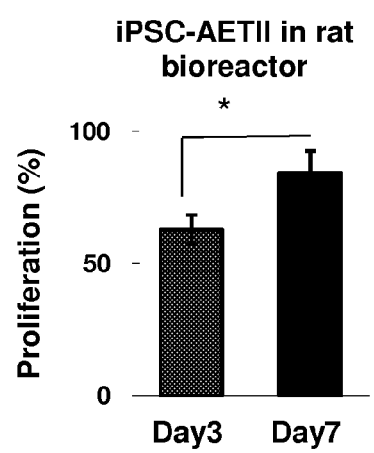
Figure 5N
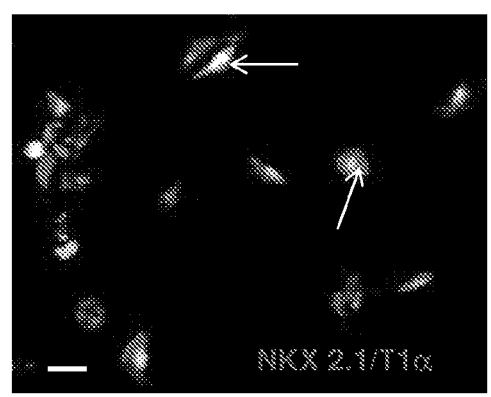
Figure 5O

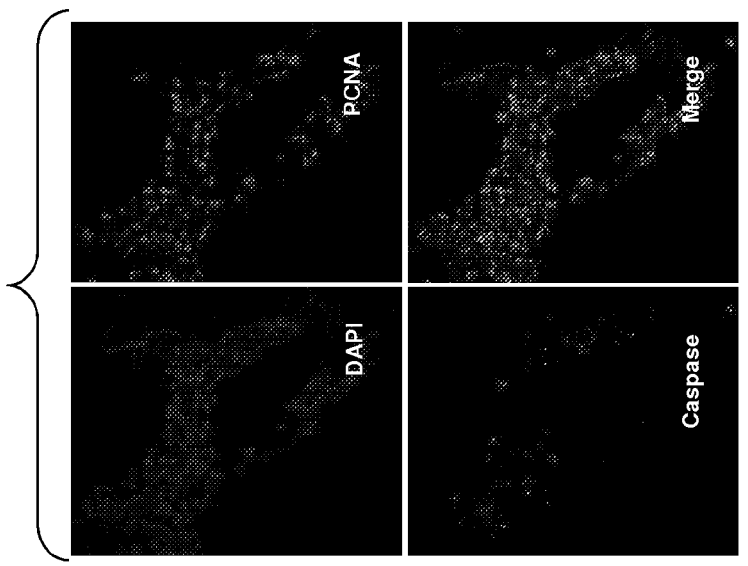
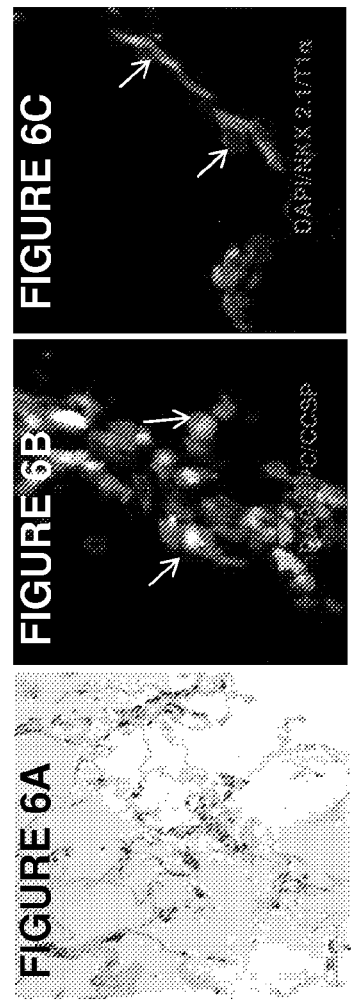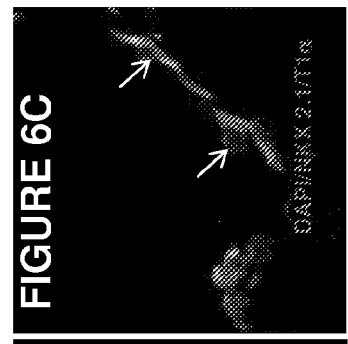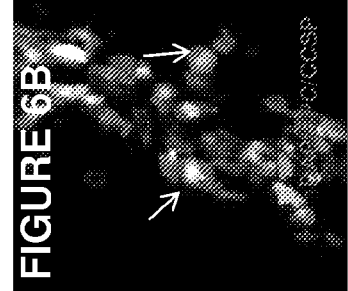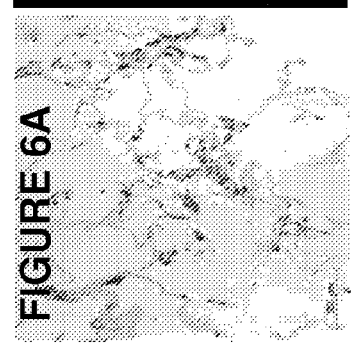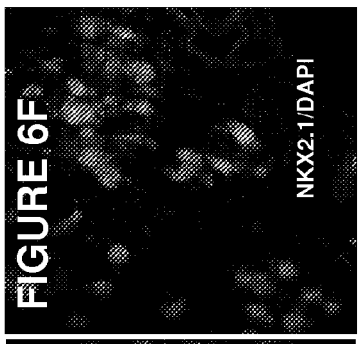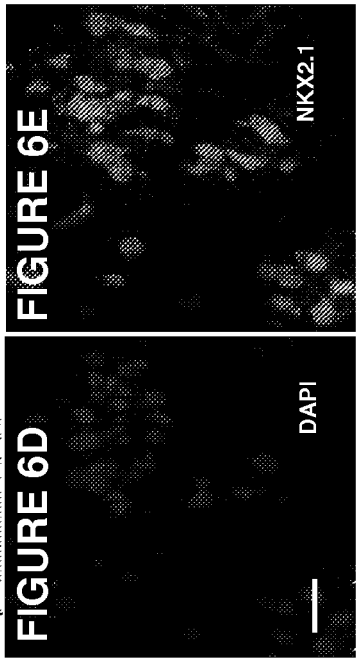

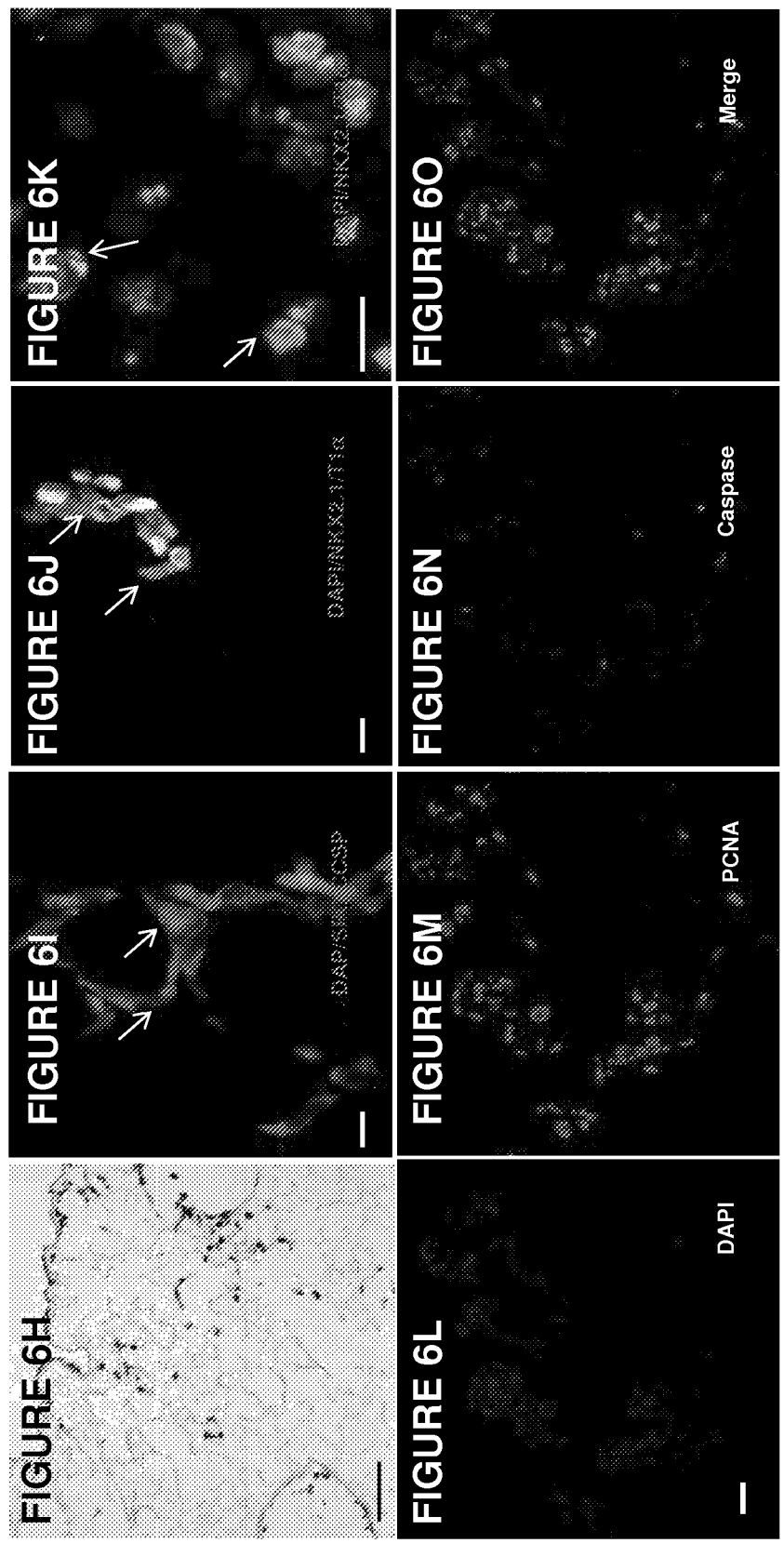

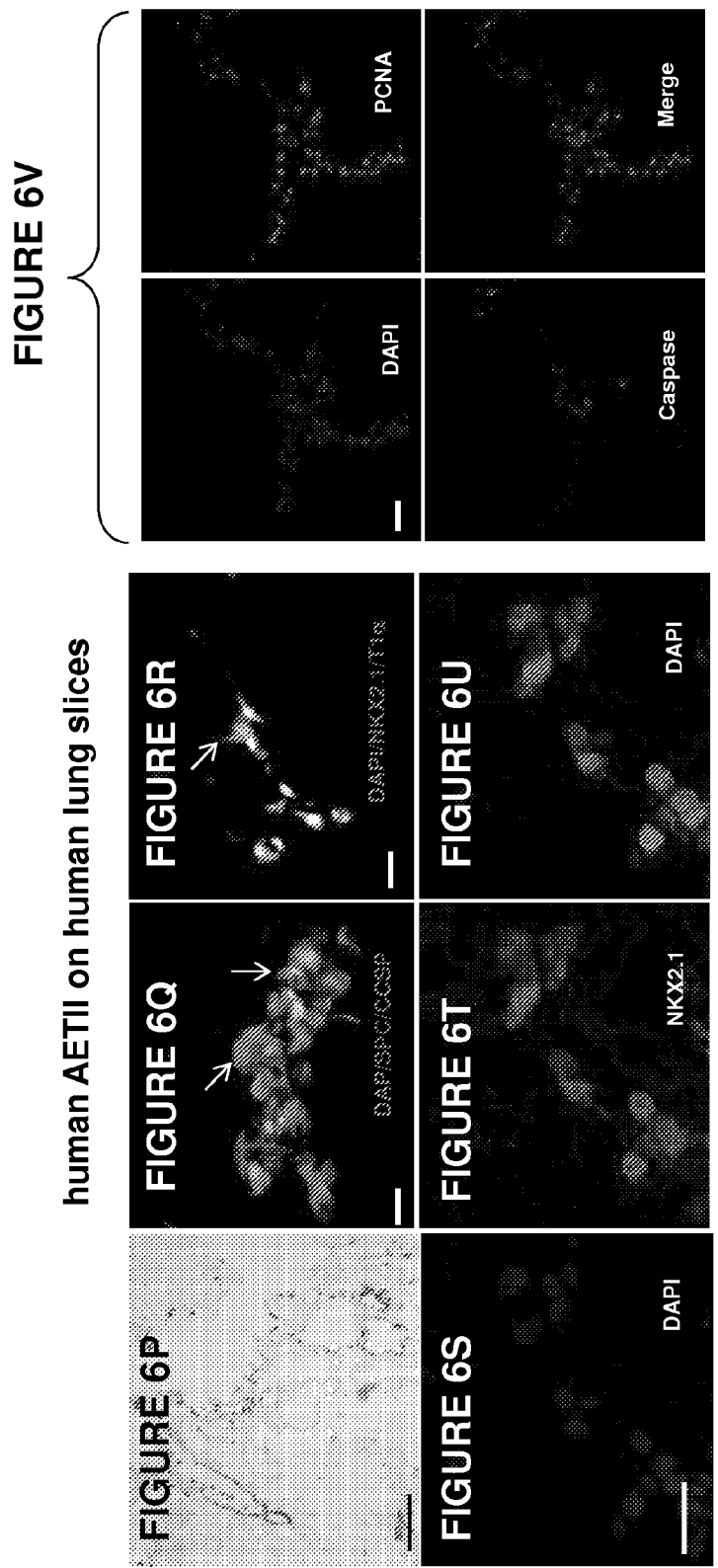

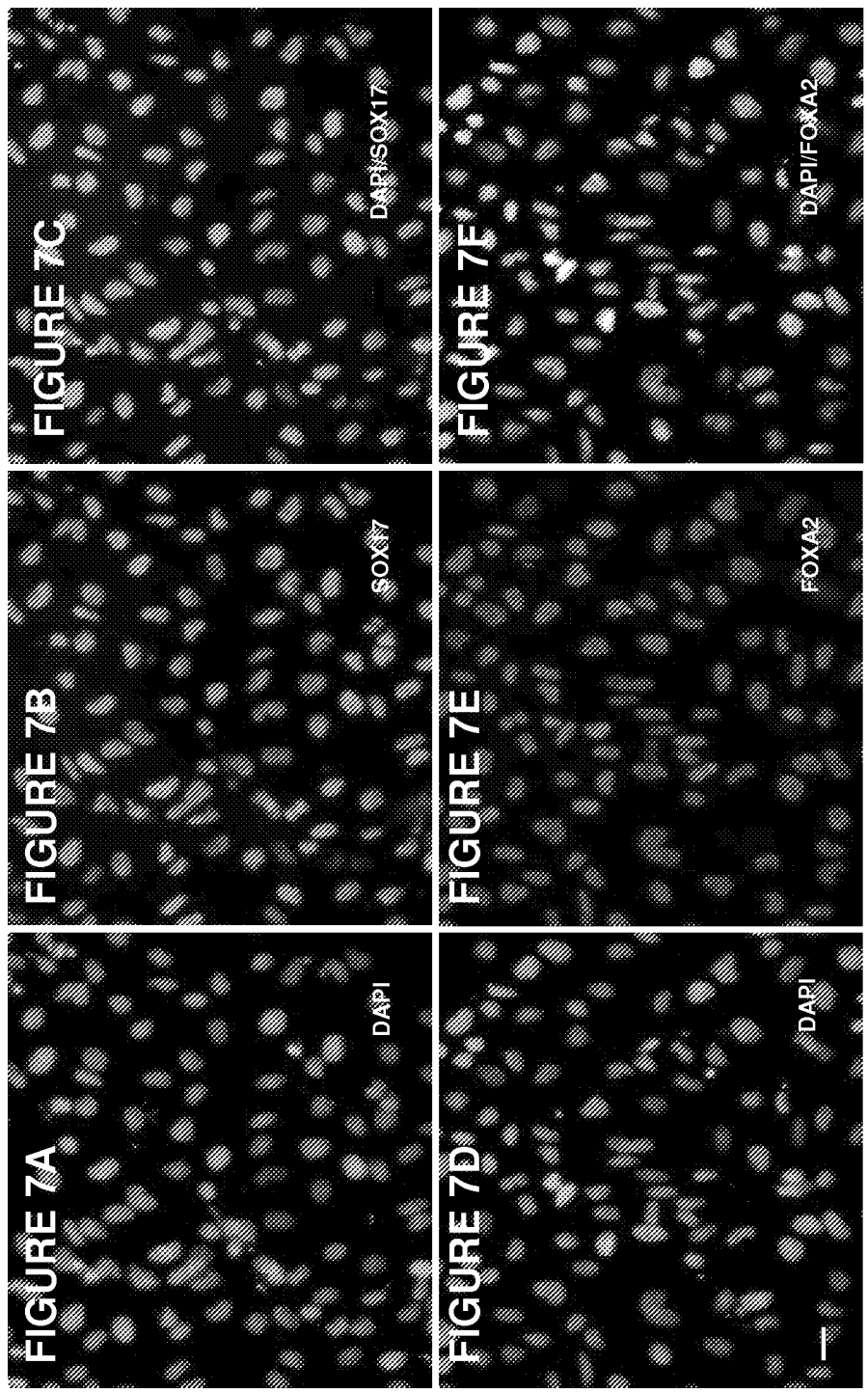

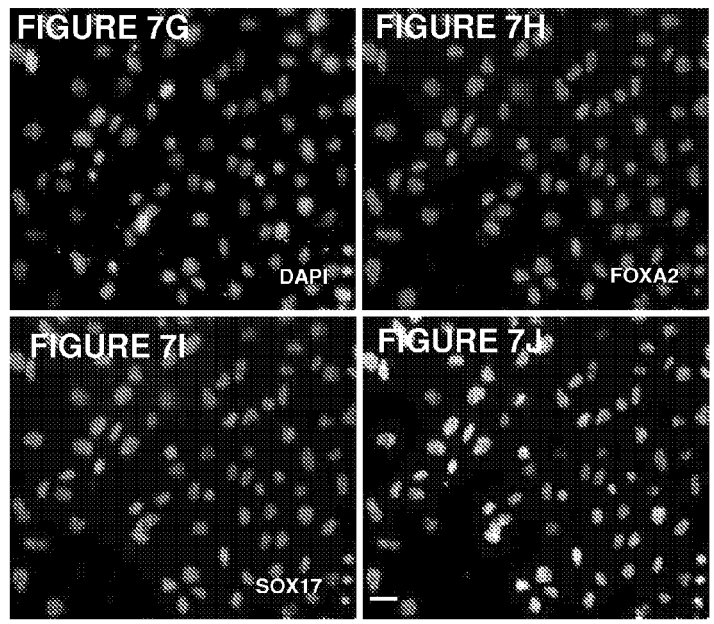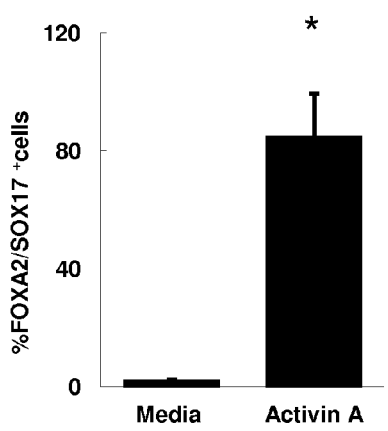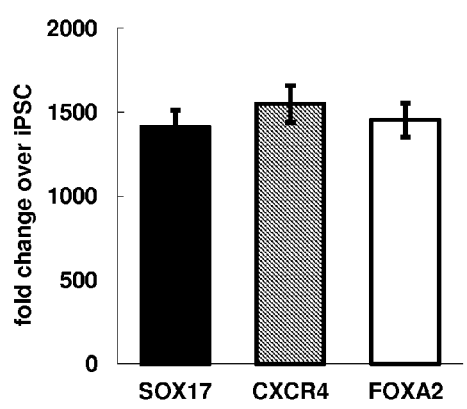

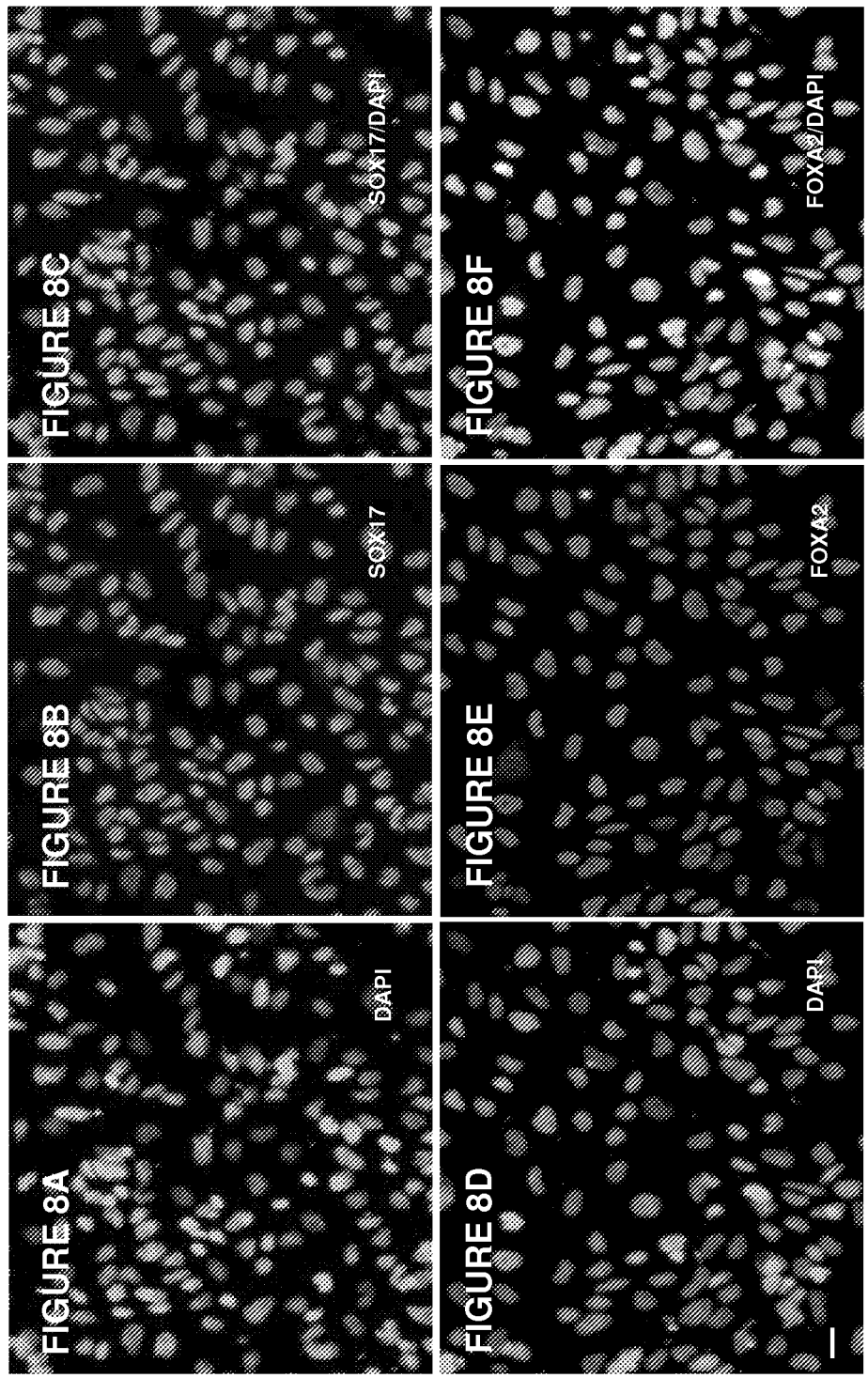

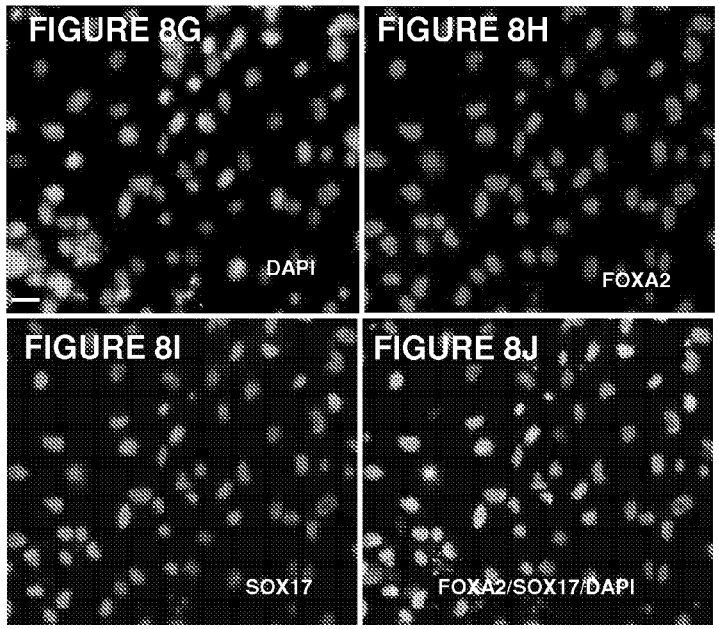
FIGURE 8K
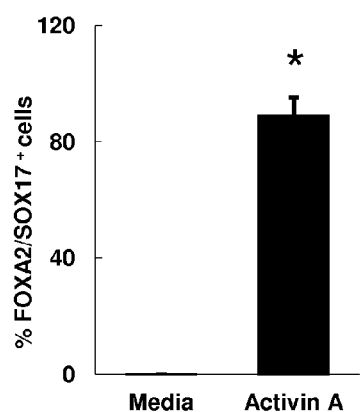
FIGURE 8L
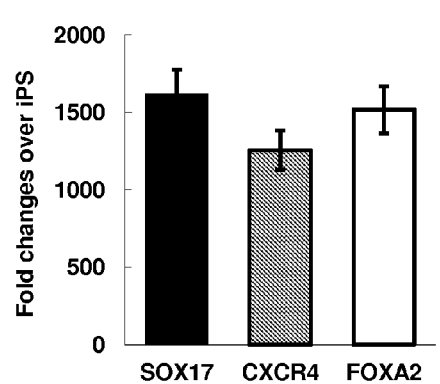

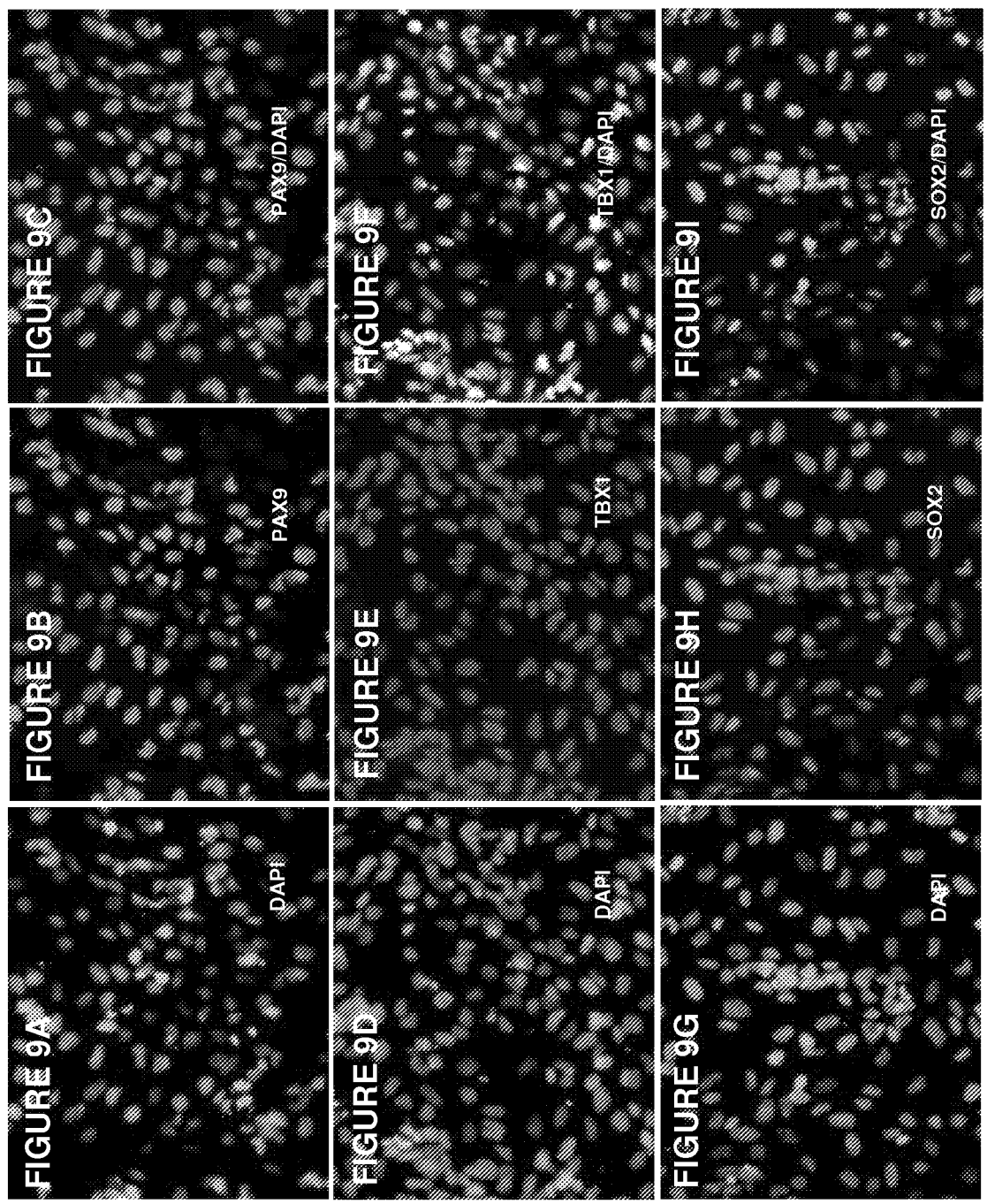

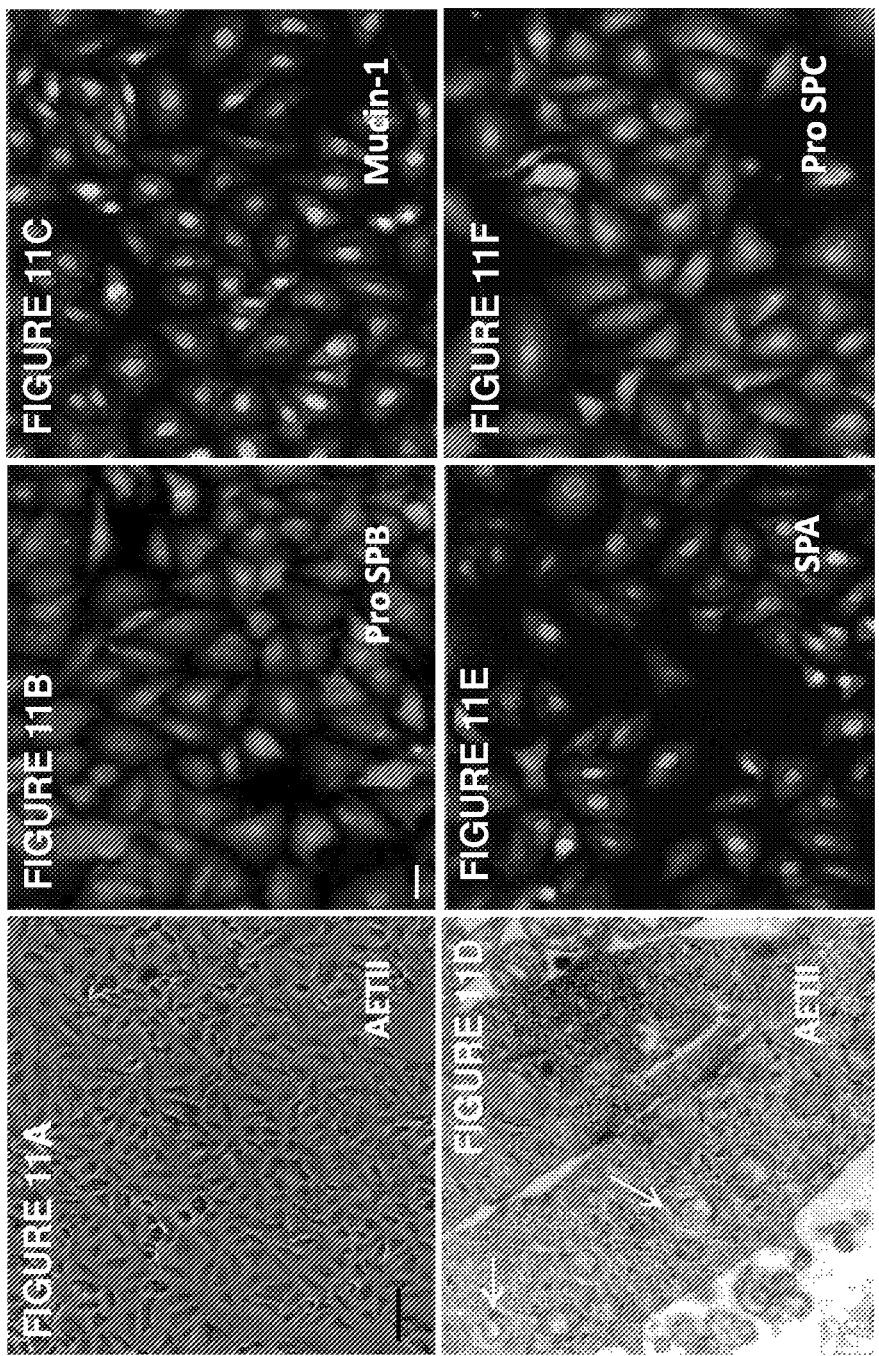

FIGURE 16D
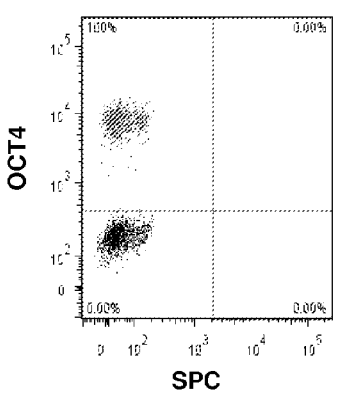
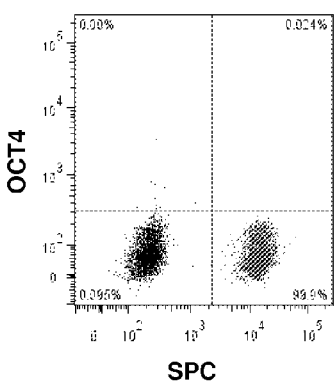
FIGURE 16E
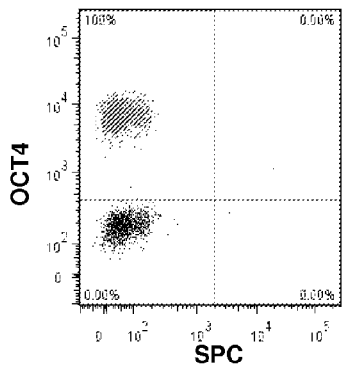
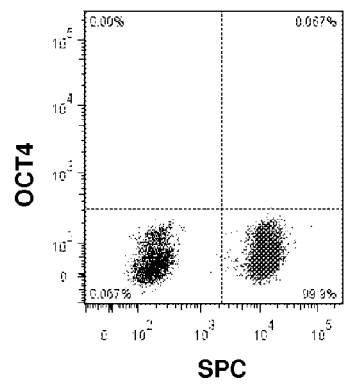

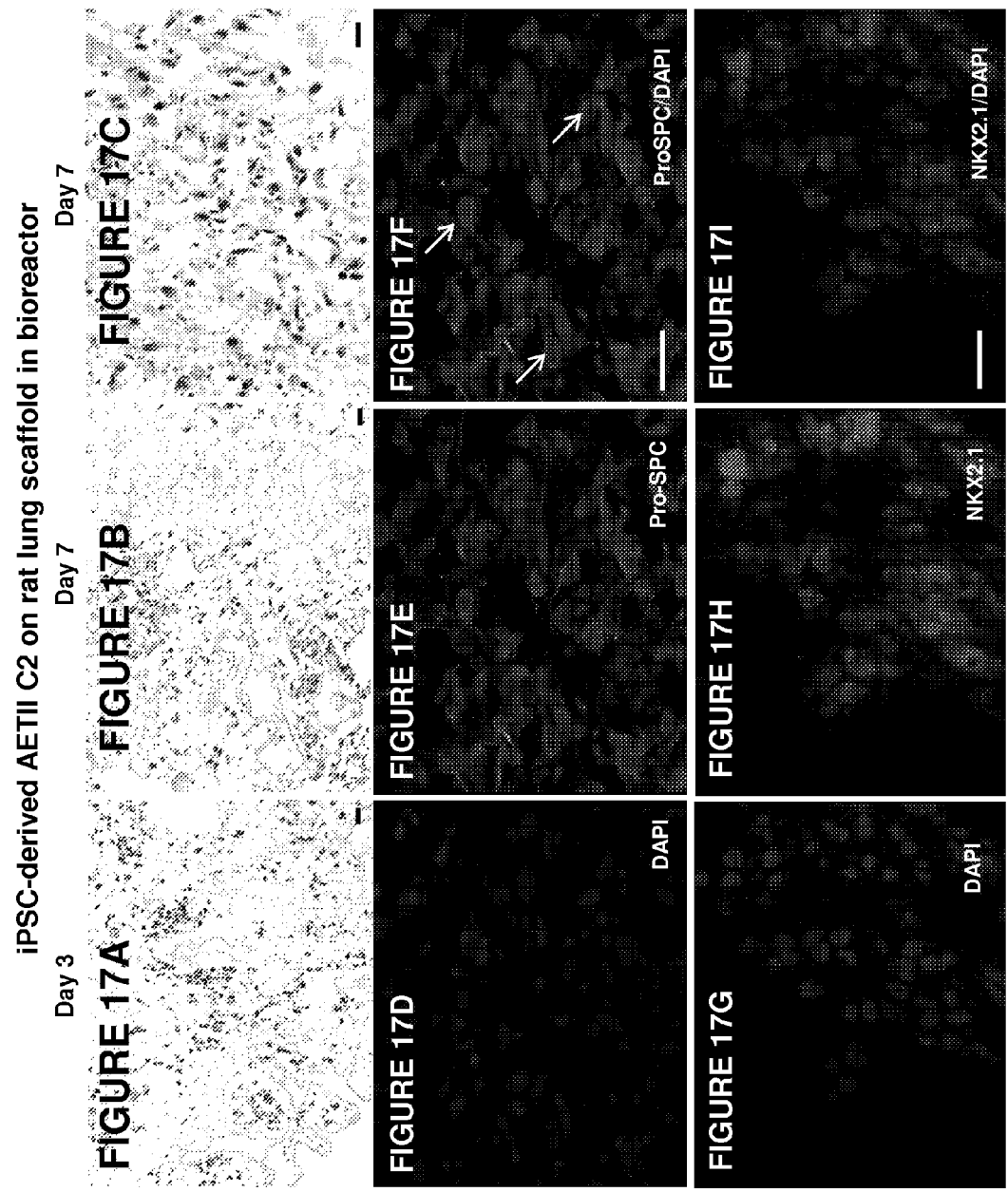

iPSC-derived AETII C2 on rat lung scaffold in bioreactor
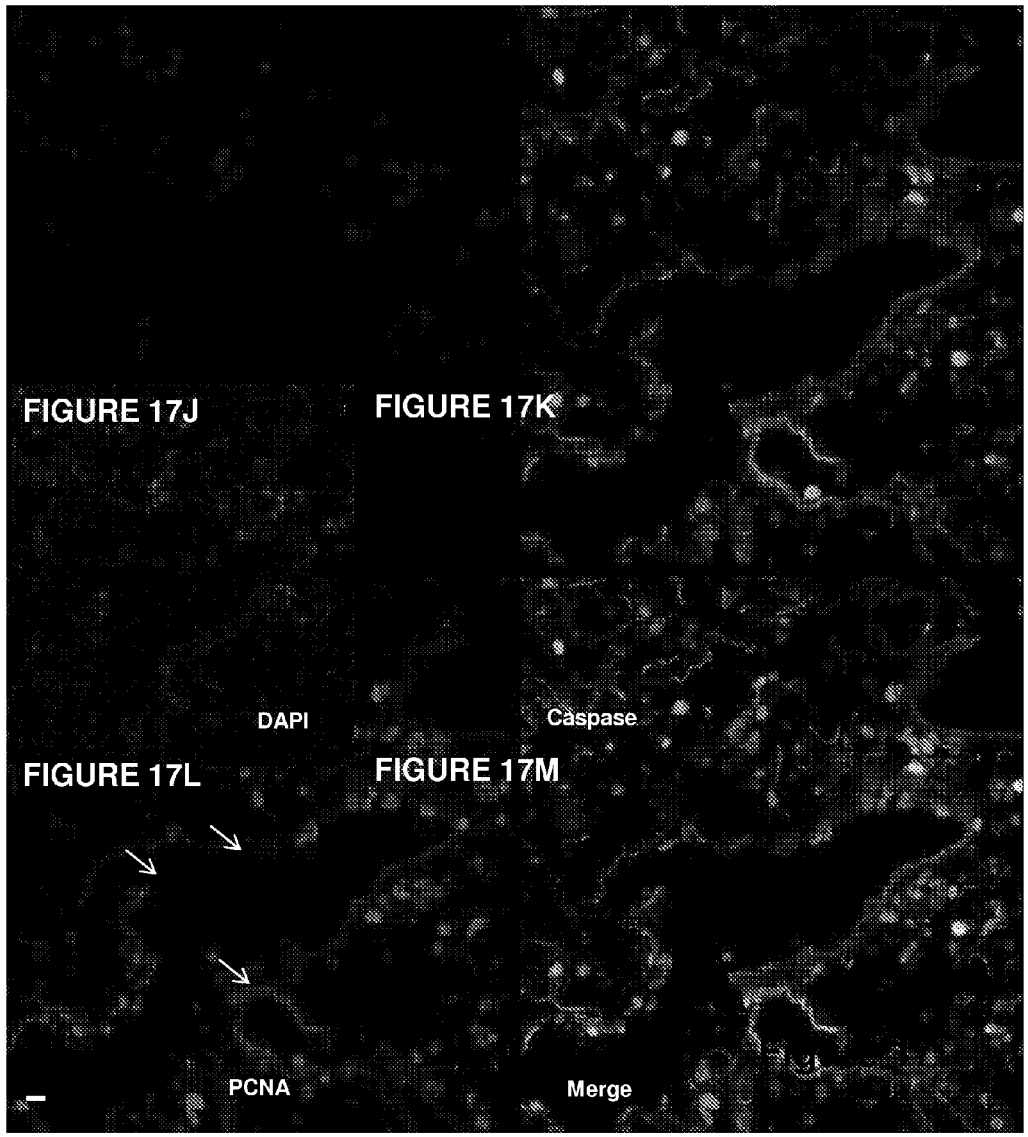

DIFFERENTIATION OF HUMAN IPS CELLS TO HUMAN ALVEOLAR TYPE II VIA DEFINITIVE ENDODERM

CROSS-REFERENCE TO RELATED APPLICATION

The present application is a continuation of International Patent Application No. PCT/US2013/061687, filed on Sep. 25, 2013, which is entitled to priority under 35 U.S.C. § 119(e) to U.S. Provisional Application Ser. No. 61/705,427, filed Sep. 25, 2012, the contents of which are incorporated by reference herein in its entirety.

STATEMENT REGARDING FEDERALLY SPONSORED RESEARCH OR DEVELOPMENT

This invention was made with government support under EB008366, HL107205, HL107768, HL111016, HL083895, and HL098220 awarded by National Institutes of Health. The government has certain rights in the invention.

BACKGROUND OF THE INVENTION

Lung disease is the third-leading cause of death in the United States, with more than 400,000 deaths annually (Longmire T A, et al. 2012. Cell Stem Cell 10(4):398-411, Petersen T H, et al. 2011. Material today 14(5):196-201). Lung transplantation is a possible treatment for people who have end-stage lung disease. Lung transplantation is limited by the low availability of donor lungs. Moreover, surgical, medical and immunological complications cause considerable morbidity and mortality in this population. As a result, many patients die each year while on a waiting list or because of transplant complications (Longmire T A, et al. 2012. Cell Stem Cell 10(4):398-411, Nichols J E, et al. 2012. J Cell Biochem 113(7):2185-2192, McCurry K R, et al. 2009. Am J Transplant 9(Part 2):942-958).

Transplantation of adult lung stem and progenitor cells or alveolar cells, isolated from human lung, is emerging as an alternative to whole organ transplantation (Wang D, et al. 2007. Proc Natl Acad Sci USA. 104(11):4449-4454). However, this approach is also limited by the scarcity of human epithelial cells, and the difficulties of expanding these cells in vitro. Moreover, the successful engraftment of such cells in vivo in injured lungs has not yet been demonstrated (Wang D, et al. 2007. Proc Natl Acad Sci USA. 104(11):4449-4454, Tesei A, et al. 2009. Cell Prolif 42(3):298-308, Fujino N, et al. 2012. Am J Respir Cell Mol Biol 46(4):422-430).

One potential future treatment for severe lung disease is transplantation with engineered lungs that are capable of gas exchange. To avoid immunological rejection, such engineered lungs should be created using individual-specific (autologous) lung and airway cells (Nichols J E, et al. 2012. J Cell Biochem 113(7):2185-2192, Petersen T H, et al. 2010. Science 329(5991):538-541, Badylak S F, et al. 2012. Lancet 379(9819):943-952). Therefore, a significant emphasis is being placed on identifying a reliable source of functional lung epithelial cells to be used in lung-related therapies (Petersen T H, et al. 2011. Material today 14(5):196-201, Kotton D N, et al. 2012. Am J Respir Crit Care Med 185(12):1255-1260).

Induced pluripotent stem (iPS) cells are the product of adult somatic cell reprogramming to an embryonic-like state by inducing a "forced" expression of specific pluripotent genes (Takahashi K, et al. 2007. Cell 131(5):861-872, Yu J, et al. 2007. Science 318(5858):1917-1920). It is postulated that the use of human iPS cells may be the most effective strategy to develop respiratory epithelial cells that may be valuable in lung-related cell therapies and tissue engineering (Nishikawa S, et al. 2008. Nat Rev Mol Cell Biol 9(9):725-729, Green M D, et al. 2011. Nat Biotechnol 29(3):267-272, Mou H, et al. 2012. Cell Stem Cell 10(4):385-397). Given that iPS cells can be derived from the patient to be treated, they could provide a cell source that is genetically identical to the patient, allowing tissue generated from these cells to avoid immune rejection (Badylak S F, et al. 2012. Lancet 379(9819):943-952, Yu J, et al. 2007. Science 318(5858):1917-1920).

The differentiation of human embryonic stem and iPS cells (hESCs and iPSCs, respectively) into pulmonary epithelium has been challenging. Several research groups have reported the successful differentiation toward a range of pulmonary epithelial cell types, including both alveolar type II cells (AETII cells) and other airway epithelium, using a variety of protocols (Longmire T A, et al. 2012. Cell Stem Cell 10(4):398-411, Wang D, et al. 2007. Proc Natl Acad Sci USA. 104(11):4449-4454, Green M D, et al. 2011. Nat Biotechnol 29(3):267-272, Mou H, et al. 2012. Cell Stem Cell 10(4):385-397, Van Haute L, et al. 2009. Respir Res 10:105, Ali N N, et al. 2002. Tissue Eng 8(4):541-550, Rippon H J, et al. 2006. Stem Cells 24(5):1389-1398, Samadikuchaksaraei A, et al. 2006. Tissue Eng 12(4):867-875). However, conditions for directing hESCs or iPSCs to differentiate along an alveolar epithelial lineage with high homogeneity have not yet been reported, and most protocols generate a mixed population of epithelial cells from hESCs or iPSCs.

Recently, the focus in organ engineering has centered on decellularizing complex organs such as heart, liver, and kidney, and using the acellular matrices as scaffolds for repopulation with organ-specific cells. Because the decellularized organ has the extracellular matrix template, it contains appropriate three-dimensional (3D) architecture and regionally-specific sites for cellular adhesion (Nichols J E, et al. 2012. J Cell Biochem 113(7):2185-2192, Petersen T H, et al. 2010. Science 329(5991):538-541). With extracellular matrix derived from donor lungs, the capacity to regenerate lung tissue from autologous cells (e.g., autologous iPS-derived epithelium) would therefore constitute a major medical advance. One way to accomplish this in lung engineering is to differentiate human iPSCs into respiratory epithelial cells and/or into putative postnatal stem cells of the respiratory system, and to reseed the lung acellular matrix with these cells (Badylak S F, et al. 2012. Lancet 379(9819):943-952).

There is a need in the art for regeneration of lung tissue from autologous cells. The present invention addresses this unmet need in the art.

SUMMARY OF THE INVENTION

The invention provides a method of differentiating a population of stem cells into a population of lung cells, the method comprising: a) inducing a stem cell into a definitive endoderm cell; b) inducing the definitive endoderm cell into an anterior foregut endoderm cell; c) inducing the anterior foregut endoderm cell into a lung cell, thereby differentiating a stem cell into a lung cell.

In one embodiment, the stem cell is cultured without serum in the presence of Activin A in order to induce the stem cell into a the definitive endoderm cell.

In one embodiment, the definitive endoderm cell is cultured in the presence of an extracellular matrix (ECM) protein and a culture medium supplemented with an inhibitor of bone morphogenic protein (BMP) and an inhibitor of TGF-β signaling in order to induce the definitive endoderm cell into an anterior foregut endoderm cell.

In one embodiment, the inhibitor of BMP is NOGGIN and the inhibitor of TGF-β signaling is SB-431542.

In one embodiment, the ECM protein is human ECM selected from the group consisting of collagen, laminin, fibronectin, tenascin, elastin, proteoglycan, glycosaminoglycan, and any combination thereof.

In one embodiment, the anterior foregut endoderm cell is cultured in the presence of a differentiation medium comprising FGF-10, EGF, Wnt3a, and KGF in order to induce the anterior foregut endoderm cell into a lung cell wherein the lung cell is an alveolar epithelial type II cell.

In one embodiment, the differentiation medium does not include BMP4.

In one embodiment, the alveolar epithelial type II cell is an alveolar epithelial type II progenitor cell.

In one embodiment, the population of lung cells is at least 95% of cells exhibiting an alveolar type II phenotype.

In one embodiment, the alveolar type II phenotype is expression of an alveolar type II cell marker selected from the group consisting of SPC, Mucin-1, SPB, CD54, and any combination thereof.

In one embodiment, the lung cell is cultured on a decellularized lung matrix.

The invention provides a population of lung cells produced by a method of differentiating a stem cell into a lung cell, the method comprising: a) inducing a stem cell into a definitive endoderm cell; b) inducing the definitive endoderm cell into an anterior foregut endoderm cell; c) inducing the anterior foregut endoderm cell into a lung cell, thereby differentiating a stem cell into a lung cell.

In one embodiment, the population is at least 95% of cells exhibiting an alveolar type II phenotype.

In one embodiment, the alveolar type II phenotype is expression of an alveolar type II cell marker selected from the group consisting of SPC, Mucin-1, SPB, CD54, and any combination thereof.

In one embodiment, the population of cells comprises genetically modified cells.

In one embodiment, the cells are genetically modified to express a therapeutic gene.

In one embodiment, the cells resemble freshly isolated human primary alveolar type II cells.

The invention also provides a method of alleviating or treating a lung defect in a mammal, the method comprising administering to the mammal a therapeutically effective amount of a composition comprising a population of lung cells produced by a method of differentiating a stem cell into a lung cell, thereby alleviating or treating said lung defect in said mammal, wherein the differentiation method comprise: a) inducing a stem cell into a definitive endoderm cell; b) inducing the definitive endoderm cell into an anterior foregut endoderm cell; c) inducing the anterior foregut endoderm cell into a lung cell, thereby differentiating a stem cell into a lung cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIGS. 1A through 1D, is a series of images depicting schematics summarizing the experiments. FIG. 1A is an image depicting a schematic protocol for directed differentiation of iPSCs to AETII in vitro in 22 days. Cytokines were added at different steps indicated on top of panel. FIG. 1B is an image depicting the summary of lung developmental steps and corresponding markers at each step. FIG. 1C is an image depicting a schematic summarizing the iPSC differentiation and decellularization-recellularization of both rat and human lung with iPSC-derived AETII cells. FIG. 1D is a series of phase-contrast images of iPSCs at day 0, DE cells at day 6, and differentiated cells at day 15 and 22, which are termed AETII cells. Scale bar, 63 μm.

FIG. 2, comprising FIGS. 2A through 2O, is a series of images depicting the characterization of cells at day 8 of differentiation to produce anterior foregut endoderm (AFE). (FIGS. 2A-2I) Immunofluorescence analysis of AFE markers; (FIGS. 2A, 2D, 2G) show DAPI staining for nuclei; (FIGS. 2B, 2E, 2H) show PAX9, TBX1 and SOX2 positive cells; (FIGS. 2C, 2F, 2I) merge at day 8. (FIG. 2O) Flow cytometric analysis of positive cells for NKX2.1. Up to 24% of AFE cells were positive for NKX2.1 at day 13. (Y axis: percentages of positive cells for NKX2.1). Bars indicate mean±SEM of n=3 independent experiments for qRT-PCR and flow cytometry. * denotes statistically significant difference p-value<0.05. Scale bar, 31 μm.

FIG. 3, comprising FIGS. 3A through 3K, is a series of imaged depicting functional characterization of AETII cells derived from iPSCs, day 22 of differentiation (C1 clone). (FIGS. 3A-3D) Immunostaining of alveolar type II marker, (FIG. 3A) ProSPC, (FIG. 3B) Mucin-1, (FIG. 3C) proSPA, (FIG. 3D) ProSPB. (Scale bar, 63 μm) (FIGS. 3E-3F) Transmission electron microscopy represent (FIG. 3E) human AETII and (FIG. 3F) iPSC-derived AETII containing characteristic cytoplasmic laminar bodies (Scale bar, 0.5 μm). (FIG. 3G) qRT-PCR analysis in undifferentiated iPSC, DE, AFE and differentiated AETII cells compared to human AETII, from three independent experiments. Values from the triplicate PCR reactions for a gene of interest (SPA, SPB, SPC, and Mucin-1) were normalized against average GAPDH Ct values from the same cDNA sample. Fold change of GOI transcript levels between iPS derived-AETII and human type II cells equals $2^{-\Delta\Delta Ct}$, where $\Delta Ct=Ct_{(GOI)}-Ct_{(GAPDH)}$, and $\Delta\Delta Ct=\Delta Ct_{(AETII)}-\Delta\Delta Ct_{(ATII)}$. (FIG. 3H) Flow cytometry analysis for the percentage of positive cells for alveolar type II and type I markers at day 22. Cells were negative for, p63 and SOX2. (FIG. 3I) Expression of albumin, CD31, TSHR, and CC10 (CCSP) in iPSC-AETII. Cells were negative for genes indicative of other lineages at day 22. (FIG. 3J) Amount of secreted SPC in the iPSC-derived AETII supernatants collected during the time course of differentiation compared to human type II cells determined by ELISA. (FIG. 3K) Western blot for proSPC in iPSC-AETII at day 22 and β-actin as an internal control. Bars indicate ±SEM and n=3 independent experiments for qRT-PCR, ELISA and flow cytometry. * denotes statistically significant difference p-value<0.05.

FIG. 4, comprising FIG. 4A through FIG. 4D, is a series of images depicting the functional characterization of AETI cells derived from iPSCs, day 29 of differentiation (C1 clone). (FIG. 4A-4B) Immunofluorescent staining of alveolar type I marker (FIG. 4A) T1α (FIG. 4B) Caveolin-1 (Scale bar, 63 μm). (FIG. 4C) Flow cytometry analysis for the percentage of positive cells for alveolar type I marker at day 29 in the presence and absence of IWR-1 (Y axis: % of positive cells). (FIG. 4D) qRT-PCR analysis in AETI cells as compared to native human type I (AETI) cells, from three independent experiments. Values from the triplicate PCR reactions for a gene of interest (AQ5, T1α, Caveolin-1) were normalized against average GAPDH Ct values from the same cDNA sample. Fold change of GOI transcript levels between iPS derived-AETI and human type I cells equals $2^{-\Delta\Delta Ct}$, where $\Delta Ct=Ct_{(GOI)}-Ct_{(GAPDH)}$, and $\Delta\Delta Ct=\Delta Ct_{(AETI)}-\Delta Ct_{(hAETI)}$ (Y axis: relative gene expression compared with human type I cells). Bars indicate ±SEM and n=3 independent experiments for qRT-PCR, ELISA and flow cytometry.

FIG. 5, comprising FIG. 5A through FIG. 5P, is a series of images depicting iPSC-derived AETII recellularized 3D rat lung tissue scaffolds in a bioreactor (FIG. 5A) H&E staining of decellularized rat lung; (FIG. 5B-5C) H&E staining of 3- and 7-day seeded rat lung with iPSC-derived AETII cells cultured in a bioreactor (scale bar 25 μm). (FIG. 5D-5F). Immunofluorescent staining for pro-SPC in AETII seeded cells at day 3 (FIG. 5D) DAPI staining; (FIG. 5E) Pro-SPC; (FIG. 5F) merge (arrows in FIG. 5F indicate positive cells for pro-SPC). (FIG. 5G-I) Immunostaining for NKX2.1 at day 7. (FIG. 5G) DAPI, (FIG. 5H) NKX2.1, (FIG. 5I) merge (arrows in FIG. 5I indicate positive cells for NKX2.1) (FIG. 5J-5M) Caspase and PCNA immunostaining at day 7, (arrows indicates positive cells for PCNA in FIG. 5L and caspase in FIG. 5M) (Scale bar, 25 μm). (FIG. 5N) Proliferation at day 7 compared with day 3. iPSC-AETII displayed a significantly increased fractional proliferation (P<0.05) after 7 days when they were stained for PCNA (Y axis: % proliferation based on the number of positive nuclei stained for PCNA). (FIG. 5O) Immunostaining of the few engrafted epithelial cells that acquired flattened morphology, positive for T1α and negative for NKX2.1 at day 7 (Scale bar, 63 μm, arrows in FIG. 5O indicate positive cells for T1α). (FIG. 5P) Flow cytometry for SPC, T1α, CCSP, p63 and SOX2 before and after seeding into rat lung scaffold in bioreactor. The number of SPC positive cells decreased during 7-day culture, while the number of positive cells for T1α increased from 9% to 31.2%. All differentiated cells from iPS cells were negative for CCSP, p63 and SOX2 before and after cell seeding.

FIG. 6, comprising FIG. 6A through FIG. 6V, is a series of images demonstrating that iPSC-derived AETII (C1 clone) adhere to sections of acellular rat and human lung matrix. (FIG. 6A-G) iPSC-AETII on human lung sections at day 7. (FIG. 6A) H&E scale bar 200 μm (FIG. 6B) Immunostaining for SPC and CCSP. (FIG. 6C) Immunostaining for NKX2.1 and T1a (arrows indicates positive cells for SPC in FIG. 6B and T1a in FIG. 6C, scale bar, 63 μm). (FIG. 6D-6F) Immunostaining for NKX2.1. (FIG. 6D) DAPI, (FIG. 6E) NKX2.1, (FIG. 6F) merge, scale bar 50 μm (FIG. 6G) Caspase and PCNA immunostaining, scale bar 49 μm. (FIGS. 6H-6O) iPSC-derived AETII cultured on rat lung sections for 7 days. (FIG. 6H) H&E, scale bar 200 μm (FIG. 6I) Immunostaining for SPC and CCSP. (FIGS. 6J-6K) Immunostaining for NKX2.1 and T1a (arrows indicates positive cells for SPC in FIG. 6I, T1α in FIG. 6J and NKX2.1 in FIG. 6K), scale bar 63 μm. (FIG. 6L) DAPI staining (FIG. 6M) Immunostaining for PCNA and (FIG. 6N) caspase, (FIG. 6O) merge (Scale bar 50 μm). (FIG. 6P-6V) Native human AETII cells, isolated from fresh adult human lung, cultured on human lung sections for 7 days. (FIG. 6P) H&E, scale bar 200 μm. (FIG. 6Q) Immunostaining for SPC and CCSP, scale bar 63 μm (FIG. 6R) Immunostaining for NKX2.1 and T1α, scale bar 63 μm (arrows indicate positive cells for SPC in FIG. 6Q and T1α in FIG. 6R). (FIG. 6S-6U) Immunostaining for NKX2.1. (FIG. 6S) DAPI, (FIG. 6T) NKX2.1, (FIG. 6U) merge, scale bar 50 μm. (FIG. 6V) Caspase and PCNA immunostaining, scale bar 49 μm.

FIG. 7, comprising FIG. 7A through FIG. 7M, is a series of images depicting the functional characteristics of definitive endoderm (DE) cells derived from iPSCs (C1 clone), at day 6. (FIG. 7A-7F) Immunofluorescence analysis of DE marker proteins, SOX17 and FOXA2 at day 6. (FIG. 7A and FIG. 7D) Nuclei were stained with DAPI, (FIG. 7B and FIG. 7E) shows SOX17, FOXA2 staining in DE cells, (FIG. 7C and FIG. 7E) Merge. (FIG. 7G-7J) immunofluorescence staining showing DE cells are positive for both SOX17 and FOXA2 at day 6, (FIG. 7K) flow cytometric analysis of double positive cells for SOX17/FOXA2 in DE cells exposed to activin A at day 6 compare to iPS cultured in media without activin A, (FIG. 7L) mRNA expression of SOX17, FOXA2 and CXCR4 from three independent experiments by qRT-PCR. (Data expressed as quantification of mRNA normalized to GAPDH and average fold change in gene expression over iPSCs), (FIG. 7M) Flow cytometric analysis of SOX17, FOXA2 and CXCR4 during activin A-mediated induction of definitive endoderm in iPSC cells at day 6 (compare to DE cells stained with corresponding isotype). Bar indicate ±SEM and n=3 independent experiments for qRT-PCR and flow cytometry. * on the graph denotes statistically significant difference p-value<0.005, Scale bar, 31 μm.

FIG. 8, comprising FIG. 8A through FIG. 8M, is a series of images depicting the characteristics of definitive endoderm cells derived from iPSCs C2 clone, at day 6: (FIG. 8A-8F) Immunofluorescent staining of definitive endodermal markers, SOX17 and FOXA2 at day 6 of activin A induction (Scale bar, 31 μm), (FIG. 8G-8J) Immunofluorescence staining showing DE cells are positive for both SOX17 and FOXA2, (FIG. 8K) flow cytometric analysis of double positive cells for SOX17/FOXA2 in DE cells exposed to activin A at day 6 compare to iPS cultured in media without activin A, (FIG. 8L) Expression of SOX17, CXCR4 and FOXA2 mRNA in C2 iPSCs quantified by qRT-PCR at day 6. (Data expressed as quantification of mRNA normalized to GAPDH and average fold change in gene expression over iPS cells), (FIG. 8M) Representative flow cytometric analysis of SOX17, CXCR4 and FOXA2 in C2 iPSCs derived DE at 6 day. Bar indicate ±SEM and n=3 independent experiments for qRT-PCR and flow cytometry. * on the graph denotes statistically significant difference p-value<0.005, Scale bar, 31 μm.

FIG. 9, comprising FIG. 9A through FIG. 9O, is a series of images depicting the analysis of AFE markers in NOG-GIN/SB-431542-treated definitive endoderm in C2 iPS cells. (FIG. 9A-9I) Immunofluorescent staining of AFE markers; SOX2, TBX1, PAX9, after 2 day of NOGGIN/SB431542 induction in C2 iPS cells (at day 8). Scale bar, 31 µm, (FIG. 9J) Immunofluorescence staining showing AFE cells are positive for both SOX2 and FOXA2 at day 8, (FIG. 9K) Flow cytometric analysis of double positive cells for SOX2/FOXA2 in AFE cells at day 8. More than 85% of cells were double positive for both SOX2 and FOXA2. (FIG. 9O) Flow cytometric analysis of positive cells for NKX2.1 in AFE cells at day 13. Exposing DE to NOGGIN/SB431542 yield 26% positive cells for NKX2. Bar indicate ±SEM and n=3 biological triplicate replicates for qRT-PCR and flow cytometry, * denotes statistically significant difference p-value<0.05.

FIG. 10, comprising (FIG. 10A) SPC, (FIG. 10B) SPB and (FIG. 10C) NKX2.1 expression in AETII differentiated on collagen I, collagen IV, fibronection, and human ECM protein and matrigel, quantified qRT-PCR. The iPSC-derived DE differentiated to AETII on different ECM protein. The gene expression in iPS derived-AETII cells on different ECM proteins were compared to the level seen in iPS derived-hAETII cells on matrigel. Ct values from three independent experiments from the triplicate PCR reactions for a gene of interest (SPB, SPC, and NKX2.1) were normalized against average GAPDH Ct values from the same cDNA sample. Fold change of GOI transcript levels between iPS derived-AETII on each ECM protein and iPS derived-AETII cells on matrigel equals $2^{-\Delta\Delta Ct}$, where $\Delta Ct = Ct_{(GOI)} - Ct_{(GAPDH)}$, and $\Delta\Delta Ct = \Delta Ct_{(iPSC-AETII\ on\ ECM\ of\ interest)} - \Delta Ct_{(iPSC-AETII\ on\ Matrigel)}$. Human ECM induced significantly higher levels of SPC, SPB and NKX2.1 expression compared to each ECM proteins individually. (Bar indicate ±SEM and n=3 independent experiments).

FIG. 11, comprising FIG. 11A through FIG. 11J, is a series of images depicting the functional characterization of differentiated AETII from C2 iPSCs line. (FIG. 11A) Phase-contrast images AETII cells. (FIG. 11B-11C and FIG. 11E-11F) Immunofluorescent staining of alveolar type II markers; (FIG. 11B) Pro surfactant protein B (ProSPB), (FIG. 11C) Mucin-1, (FIG. 11E) Surfactant protein A (SPA), (FIG. 11F) Pro surfactant protein C (ProSPC) Scale bar, 63 µm, (FIG. 11D) Transmission electron microscopy, represent AETII contain characteristic cytoplasmic laminar bodies (scale bar, 1 µm) (FIG. 11G) qRT-PCR analysis in undifferentiated iPSC, DE, AFE and AETII cells derived from C2 clone compared to hATII cells that were derived from fresh human lung, from three independent experiments values from the triplicate PCR reactions for a gene of interest (SPA, SPB, SPC, Mucin-1) were normalized against average GAPDH Ct values from the same cDNA sample. Fold change of GOI transcript levels between iPS derived-AETII and human type II cells equals $2^{-\Delta\Delta Ct}$, where $\Delta Ct = Ct_{(GOI)} - Ct_{(GAPDH)}$, and $\Delta\Delta Ct = \Delta Ct_{(AETII)} - \Delta Ct_{(ATII)}$, (FIG. 11H) Flow cytometry analysis for the percentage of positive cells for alveolar type II markers at day 22. More than 95% of population were positive for type II cells marker (CD54, SPB, SPC, Mucin-1) when they were negative for CCSP (Clara cell marker), p63 (basal stem cell marker), (FIG. 11I) Expression of albumin, CD31, TSHR, CC10 (CCSP) in iPSC-derived AETII; they were negative for genes indicative of other lineages at day 22. (FIG. 11J) The amount of secreted SPC in the iPSC-derived AETII during the time course of differentiation compared to SPC secretion from isolated AETII from human lung determined by enzyme-linked immunosorbent assay. Bars indicate ±SEM and n=3 independent experiments for qRT-PCR, ELISA and flow cytometry. * denotes statistically significant difference p-value<0.05.

FIG. 12, comprising (FIG. 12A-12B) Sequential up and downregulation of DE-specific and AFE-specific genes during differentiation to AETII cells quantified by qRT-PCR. (FIG. 12A-12B) Ratio of gene expression in DE cells compare to iPSCs during differentiation quantified by qRT-PCR in (FIG. 12A) C1 clone and (FIG. 12B) C2 clone (Data expressed as quantification of mRNA normalized to GAPDH and average fold change in gene expression over DE cells) (FIG. 12C-12D) Sequential up and downregulation of AFE-specific proteins during differentiation of iPSCs to AETII quantified by qRT-PCR in (FIG. 12C) C1 clone and (FIG. 12D) C2 clone. Data expressed as quantification of mRNA normalized to GAPDH and average fold change in gene expression over AFE cells; bar indicate ±SEM and n=3 independent experiments.

FIG. 13, comprising (FIG. 13A-13B) Kinetics of NKX2.1 and SPC mRNA expression at different days, quantified by real time qRT-PCR. (FIG. 13A) SPC expression during differentiation of iPS cells to AETII. Ct values of SPC is normalized to GAPDH and expressed to levels seen in ATII cells isolated from human lung (hATII) (FIG. 13B) NKX2.1 during differentiation of iPS cells to AETII. Data expressed as quantification of mRNA normalized to GAPDH and expressed to the level of seen in isolated human primary type II. (FIG. 13C-13D) Flow cytometry analysis for the percentage of positive cells for (FIG. 13C) NKX2.1 from day 13 to day 22 and (FIG. 13D) SPC from day 10 to day 22. Bars indicate ±SEM and n=3 independent experiments for PCR and flow cytometry.

FIG. 14, comprising (FIG. 14A-14B) NKX2.1 and SPC mRNA expression at different days, quantified by real time RT-PCR in iPSC-derived AETII (C2 clone). (FIG. 14A) SPC expression during differentiation from day 0 to day 32. Ct value for SPC is normalized to GAPDH and expressed to levels seen in AETII cells isolated from human lung (hATII) (FIG. 14B) NKX2.1 expression during differentiation. Data expressed as quantification of mRNA normalized to GAPDH and expressed to the levels seen in isolated human type II (FIG. 14C-14D) Flow cytometry analysis for the percentage of positive cells for (FIG. 14C) NKX2.1 from day 13 to day 22 and SPC (FIG. 14D) from day 10 to day 22. Bars indicate ±SEM and n=3 independent experiments for PCR and flow cytometry.

FIG. 15, comprising (FIG. 15 and FIG. 15C) Flow cytometry analysis for the percentage of positive cells for CD166 from day 10 to day 28 in AETII derived from (FIG. 15A) C1 clone and (FIG. 15C) C2 clone. (FIG. 15B and FIG. 15D) Flow cytometry analysis for the percentage of positive cells for α6β4 from day 8 to day 22 in AETII derived from (FIG. 15B) C1 clone and (FIG. 15D) C2 clone.

FIG. 16, comprising FIG. 16A through FIG. 16E, is a series of images depicting the pluripotency marker analysis in C2 clone in day 0 and during differentiation to AETII. (FIG. 16A). Immunofluorescent staining of iPSC markers; OCT4, Nanog, SSEA4, Tra1-81 in both iPSC clone C1 and C2 (Scale bar, 100 µm). Both clones were positive for pluripotency genes at day 0. (FIG. 16B-C) Downregulation of iPSC-specific genes OCT4, SOX2, and Nanog during differentiation to AETI. The expression of OCT4, SOX2, and Nanog were downregulated over the time and by day 32 these markers were undetectable in iPSC-derived AETII derived from both (FIG. 16B) clone C1 and (FIG. 16C) clone C2 (Data expressed as quantification of mRNA normalized to GAPDH and average fold change in gene expression over iPS cells at day 0, bar indicates SEM and n=3 independent experiments), (FIG. 16D-16E) Expression of OCT4 and SPC in differentiated AETII cells on day 0 compare to day 22 analyzed by flow cytometry for (FIG. 16D) C1 clone and (FIG. 16E) C2 clone. At day 22 of differentiation, SPC positive iPSC-derived AETII cells were negative for OCT4.

FIG. 17, comprising FIG. 17A through FIG. 17M, is a series of images demonstrating that AETII derived from iPSC C2 clone respond to recellularize 3D lung tissue scaffolds in bioreactor (FIG. 17A-17C) H&E staining of seeded rat lung scaffold with iPSC-derived AETII cells at (FIG. 17A) day 3 and (FIG. 17B-17C) at day 7 in bioreactor. Scale bar, 200 µm. (FIG. 17D-17F) Immunostaining for SPC on seeded rat lung scafold with iPSC-derived AETII cells cultured in bioreactor at day 7 (FIG. 17D) Nuclei were stained with DAPI; (FIG. 17E) shows Pro-SPC staining (FIG. 17F) Merge, Scale bar, 50 µm (FIG. 17G-17I) Immunostaining for NKX2.1 on seeded rat lung scafold with iPSC-derived AETII cells cultured in bioreactor at day 7 (FIG. 17G) Nuclei were stained with DAPI; (FIG. 17H) shows NKX2.1 staining (FIG. 17I) Merge, Scale bar, 50 µm (FIG. 17J-17M) Immunostaining for PCNA and caspase of bioreactor cultured iPSC-derived APTII cells at day 7. Scale bar, 49 µm

DETAILED DESCRIPTION

Figure 1C:
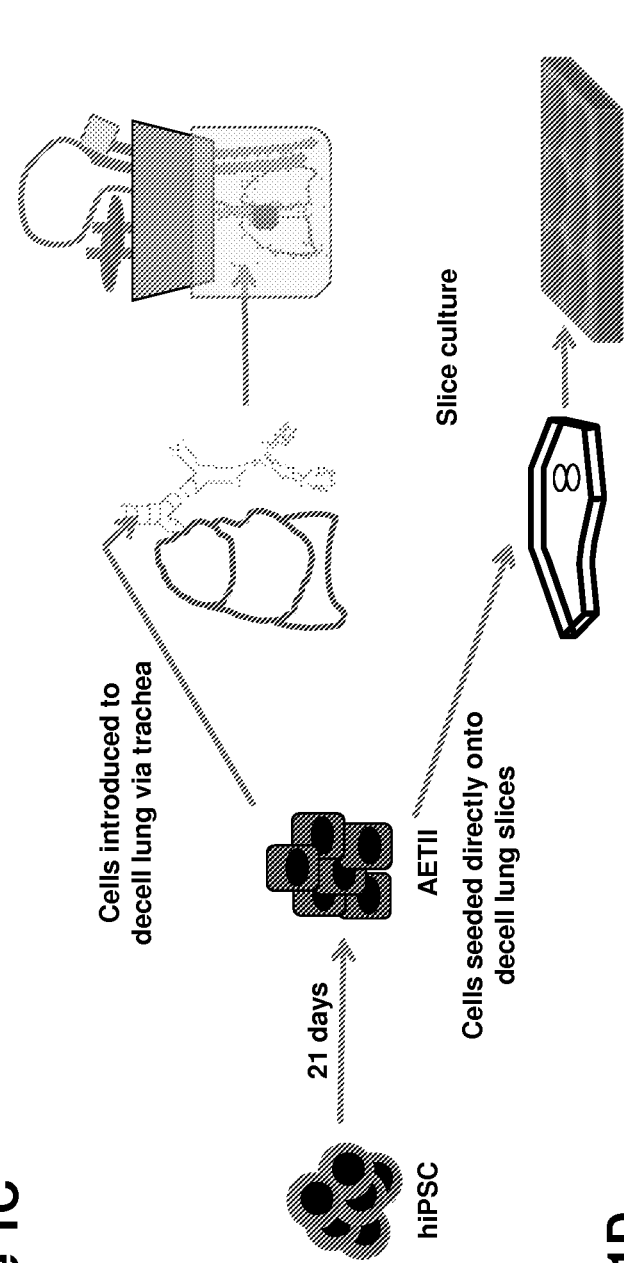
Figure 1D:
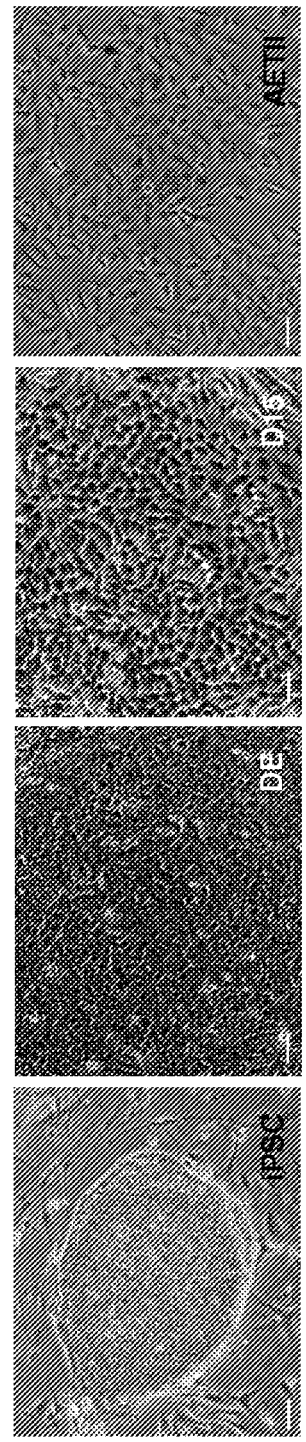

The invention provides a method of differentiating a stem cell into a lung cell, preferably an alveolar epithelial type II cell. In one embodiment, the stem cell is a human induced pluripotent stem (iPS) cell.

In one embodiment, the method of generating a lung cell comprises culturing a stem cell without serum in the presence of Activin A in order to generate a definitive endoderm (DE) population. The DE population can then be differentiated into anterior foregut endoderm (AFE) by culturing the DE cells in the presence of the combination of an extracellular matrix (ECM) protein and a culture medium supplemented with an inhibitor of BMP and an inhibitor of TGF-β signaling. Preferably, the inhibitor of BMP is NOGGIN and the inhibitor of TGF-β signaling is SB-431542.

The AFE cells can be cultured in the presence of a differentiation medium to induce differentiation into a desired cell type. For example, induction to differentiate into an alveolar epithelial type II cell comprises culturing the AFE cells in the presence of a differentiation medium comprising FGF-10, EGF, Wnt3a, and KGF. Preferably, the alveolar epithelial type II cell differentiation medium does not include BMP4.

The compositions and methods of the invention are useful for among other things, drug discovery, toxicity testing, disease pathology, investigating lung developmental biology, and the like.

The invention relates to the discovery that alveolar epithelial type II cells can be generated in vitro. Accordingly, the invention provides methods and compositions for the generation of alveolar epithelial type II cells as a form of regenerative medicine. In one embodiment, the method allows for the generation of a pure population of alveolar type II progenitor cells whereby the cells express a high percentage of lung alveolar type II markers including but is not limited to SPC, SPB, Mucin-1, and CD54.

The invention also provides a method of alleviating or treating a lung defect in a mammal, preferably a human. The method comprises administering to the mammal in need thereof a therapeutically effective amount of a composition comprising an alveolar epithelial type II cell or otherwise cells that exhibit at least one characteristic of an alveolar epithelial type II cell, thereby alleviating or treating the lung defect in the mammal.

In one embodiment, the invention provides a method of repairing injured or diseased alveolar epithelial tissue in the lung of a mammal comprising transplanting into the lung, at a site comprising injured or diseased alveolar epithelial tissue, a population of differentiated stem cells, or progeny thereof, at least 95%, preferably at least 96%, more preferably at least 97%, more preferably 98%, yet more preferably at least 99% of which exhibit an alveolar type II phenotype. The population of cells with alveolar type II phenotype is prepared using the methods of the invention, and, after transplantation, is effective to repair at least a portion of the injured or diseased alveolar epithelial tissue at the site.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture.

Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

As used herein, "anterior foregut endoderm" refers to endoderm that is anterior to the endoderm that gives rise to the liver. One of ordinary skill in the art will readily appreciate that "anterior foregut endoderm" thus includes, for example, pharyngeal endoderm and other, more highly differentiated populations of endodermal cells and that the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, "anterior foregut endoderm" refers to endoderm that is anterior to the endoderm. One of ordinary skill in the art will readily appreciate that "anterior foregut endoderm" thus includes, for example, pharyngeal endoderm and other, more highly differentiated populations of endodermal cells and that the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx.

As used herein, to "alleviate" a disease, defect, disorder or condition means reducing the severity of one or more symptoms of the disease, defect, disorder or condition.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of primate embryonic stem cells in a substantially undifferentiated state can be employed.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

"Bioactive agents," as used herein, can include one or more of the following: chemotactic agents; therapeutic agents (e.g., antibiotics, steroidal and non-steroidal analgesics and anti-inflammatories (including certain amino acids such as glycine), anti-rejection agents such as immunosuppressants and anti-cancer drugs); various proteins (e.g., short term peptides, bone morphogenic proteins, collagen, hyaluronic acid, glycoproteins, and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGF$\beta$ I-III), parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDFS, GDF6, GDF8), recombinant human growth factors (e.g., MP52, and MP-52 variant rhGDF-5), cartilage-derived morphogenic proteins (CDMP-1; CDMP-2, CDMP-3)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopedic field, it is anticipated that at least some of these substances will have use in the present invention, and such substances should be included in the meaning of "bioactive agent" and "bioactive agents" unless expressly limited otherwise. Preferred examples of bioactive agents include culture media, bone morphogenic proteins, growth factors, growth differentiation factors, recombinant human growth factors, cartilage-derived morphogenic proteins, hydrogels, polymers, antibiotics, anti-inflammatory medications, immunosuppressive mediations, autologous, allogenic or xenologous cells such as stem cells, chondrocytes, fibroblast and proteins such as collagen and hyaluronic acid. Bioactive agents can be autologous, allogenic, xenogenic or recombinant.

The term "biologically compatible carrier" or "biologically compatible medium" refers to reagents, cells, compounds, materials, compositions, and/or dosage formulations which are suitable for use in contact with the tissues of human beings and animals without excessive toxicity, irritation, allergic response, or other complication commensurate with a reasonable benefit/risk ratio.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "cell medium" as used herein, refers to a medium useful for culturing cells. An example of a cell medium is a medium comprising DMEM/F 12 Ham's, 10% fetal bovine serum, 100 U penicillin/100 µg streptomycin/ 0.25 µg Fungizone. Typically, the cell medium comprises a base medium, serum and an antibiotic/antimycotic. However, cells can be cultured with stromal cell medium without an antibiotic/antimycotic and supplemented with at least one growth factor. Preferably the growth factor is human epidermal growth factor (hEGF). The preferred concentration of hEGF is about 1-50 ng/ml, more preferably the concentration is about 5 ng/ml. The preferred base medium is DMEM/F12 (1:1). The preferred serum is fetal bovine serum (FBS) but other sera may be used including horse serum or human serum. Preferably up to 20% FBS will be added to the above media in order to support the growth of stromal cells. However, a defined medium could be used if the necessary growth factors, cytokines, and hormones in FBS for cell growth are identified and provided at appropriate concentrations in the growth medium. It is further recognized that additional components may be added to the culture medium. Such components include but are not limited to antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing cells. Rather, any media capable of supporting cells in tissue culture may be used.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, the heart, lung, kidney, liver, pancreas, spleen, bladder, ureter and urethra, cartilage, bone, brain, spine cord, peripheral nerve.

As used herein "definitive endoderm (DE)" and definitive endoderm cells (DE-cells) refers to cells exhibiting such as but not limited to protein or gene expression and or/or morphology typical to cells of the definitive endoderm or a composition comprising a significant number of cells resembling the cells of the definitive endoderm. A definitive endoderm cell can expresses the marker Sox17. Other markers of definitive endoderm cells include, but are not limited to MIXL2, GATA4, HNF3b, GSC, FGF17, VWF, CALCR, FOXQ1, CMKOR1 and CRIP1. Definitive endoderm cells have the capacity to differentiate into cells including those of the liver, lung, pancreas, thymus, intestine, stomach and thyroid.

The term "dedifferentiation", as used herein, refers to the return of a cell to a less specialized state. After dedifferentiation, such a cell will have the capacity to differentiate into more or different cell types than was possible prior to re-programming. The process of reverse differentiation (i.e., de-differentiation) is likely more complicated than differentiation and requires "re-programming" the cell to become more primitive.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming lung cells and other endoderm cell types. Endoderm cells can also be differentiate into other cells of endodermal origin, e.g. lung, liver, intestine, thymus etc.

"Differentiation medium" is used herein to refer to a cell growth medium comprising an additive or a lack of an additive such that a stem cell, fetal pulmonary cell or other such progenitor cell, that is not fully differentiated, develops into a cell with some or all of the characteristics of a differentiated cell when incubated in the medium.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

As used herein, "epithelial cell" means a cell which forms the outer surface of the body and lines organs, cavities and mucosal surfaces.

As used herein, "endothelial cell" means a cell which lines the blood and lymphatic vessels and various other body cavities.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of respiratory and digestive tracts (e.g. the intestine), the liver and the pancreas.

"Expandability" is used herein to refer to the capacity of a cell to proliferate, for example, to expand in number or, in the case of a population of cells, to undergo population doublings.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

As used herein, a "fetal pulmonary cells" (FPCs) refer to cells isolated from the lung tissue of an embryo. A mixed population of FPCs can include, but is not limited to epithelial, mesenchymal, and endothelial cells.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft," "autologous transplant," "autologous implant" and "autologous graft." A graft comprising cells from a genetically different individual of the same species is referred to herein by the following interchangeable terms: "allograft", "allogeneic transplant," "allogeneic implant" and "allogeneic graft." A graft from an individual to his identical twin is referred to herein as an "isograft", a "syngeneic transplant", a "syngeneic implant" or a "syngeneic graft." A "xenograft," "xenogeneic transplant" or "xenogeneic implant" refers to a graft from one individual to another of a different species.

As used herein, the term "growth factor product" refers to a protein, peptide, mitogen, or other molecule having a growth, proliferative, differentiative, or trophic effect on a cell. Growth factors include, but are not limited to, fibroblast growth factor (FGF), basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor (PDGF), vascular endothelial cell growth factor (VEGF), activin-A, bone morphogenic proteins (BMPs), insulin, growth hormone, erythropoietin, thrombopoietin, interleukin 3 (IL-3), interleukin 6 (IL-6), interleukin 7 (IL-7), macrophage colony stimulating factor, c-kit ligand/stem cell factor, osteoprotegerin ligand, insulin, nerve growth factor, ciliary neurotrophic factor, cytokines, chemokines, morphogens, neutralizing antibodies, other proteins, and small molecules. Preferably, the FGF is selected from the group selected from FGF2, FGF7, FGF10, and any combination thereof.

As used herein, the term "growth medium" is meant to refer to a culture medium that promotes growth of cells. A growth medium will generally contain animal serum. In some instances, the growth medium may not contain animal serum.

As used herein, "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in literature often denoted as human embryonic stem (hES) cells, (see, e.g., Thomson et al. (1998), Heins et. al. (2004), as well as induced pluripotent stem cells (see, e.g. Yu et al., (2007) Science 318:5858); Takahashi et al., (2007) Cell 131(5):861). The various methods and other embodiments described herein may require or utilize hPS cells from a variety of sources. For example, hPS cells suitable for use may be obtained from developing embryos. Additionally or alternatively, suitable hPS cells may be obtained from established cell lines and/or human induced pluripotent stem (hiPS) cells.

As used herein "hiPS cells" refers to human induced pluripotent stem cells.

An "isolated cell" refers to a cell which has been separated from other components and/or cells which naturally accompany the isolated cell in a tissue or mammal.

An "isolated nucleic acid" refers to a nucleic acid segment or fragment which has been separated from sequences which flank it in a naturally-occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

The term "lung specific" refers to a nucleic acid molecule or polypeptide that is expressed predominantly in the lung as compared to other tissues in the body. In a preferred embodiment, a "lung specific" nucleic acid molecule or polypeptide is expressed at a level that is 5-fold higher than any other tissue in the body. In a more preferred embodiment, the "lung specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately measure protein levels, such as Western blot analysis.

"Lung tissue" can include, but is not limited to, all lung tissue structures and associated tissues, including, but not limited to, veins, arteries, vessels, capillaries, and cells of the type that are part of, or associated with, such structures; lung and pleural tissue; and vascular smooth muscle, pericyte, and vascular endothelial lineages and/or phenotypes.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the phrase "stem cells" refers both to the earliest renewable cell population responsible for generating cell mass in a tissue or body and the very early progenitor cells, which are somewhat more differentiated, yet are not committed and can readily revert to become a part of the earliest renewable cell population.

As used herein, a "substantially purified" cell is a cell that is essentially free of other cell types. Thus, a substantially purified cell refers to a cell which has been purified from other cell types with which it is normally associated in its naturally-occurring state.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, the terms "tissue grafting" and "tissue reconstructing" both refer to implanting a graft into an individual to treat or alleviate a tissue defect, such as a lung defect or a soft tissue defect.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver.

Generally, a "trophic factor" is defined as a substance that promotes survival, growth, proliferation and/or maturation of a cell, or stimulates increased activity of a cell.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to the successful generation of a pure population of alveolar epithelial type II cells from stem cells. The alveolar epithelial type II cells differentiated from stem cells serve as a promising source of cells for use therapeutically to treat distal lung diseases, lung injuries, and genetic diseases that affect the lung.

The present invention provides a method of differentiating stem cells into cells that exhibit at least one characteristic of an alveolar epithelial type II cell. In one embodiment, the method comprises two phases wherein the first phase comprises generating a definitive endoderm (DE) population from a stem cell population and the second phase comprising differentiating the DE population into cells of the anterior foregut endoderm (AFE). With respect to the first phase, in one embodiment, stem cells are initially cultured without serum in the presence of Activin A in order to generate a DE population. With respect to the second phase, in one embodiment, the DE population is cultured in the presence of a human extracellular matrix (ECM) protein in combination with a culture medium supplemented with an inhibitor of BMP and an inhibitor of TGF-β signaling and in the absence of Activin A in order to induce differentiation into AFE. Preferably, the inhibitor of BMP is NOGGIN and the inhibitor of TGF-β signaling is SB-431542.

After AFE cells are generated, they can be cultured in the presence of a differentiation medium to induce differentiation into a desired cell type. For example, the AFE cells can be induced to differentiation into a cell that exhibits at least one characteristic of an alveolar epithelial type II cell wherein the differentiation medium comprises FGF-10, EGF, Wnt3a, and KGF. Preferably, the alveolar epithelial type II cell differentiation medium does not include BMP4.

Accordingly, the invention provides a method for directed differentiation of stem cells into cell types and tissues derived from the AFE including but is not limited to alveolar type II cells.

The invention is partly based upon the discovery that the unique protocol disclosed elsewhere herein allows for the highly efficient conversion of AFE cells into alveolar type II progenitor cells. For example, the use of ECM protein-coated surfaces in combination with specific growth factors generated a cell population that expressed a high percentage of lung alveolar type II cell markers. In one example, the methods of the invention allows for the generation of a pure population of alveolar type II cells derived from human stem cells, preferably human induced pluripotent stem (iPS) cells.

In one embodiment, the method of differentiating stem cells towards an alveolar type II cell phenotype is distinct from prior art in that the step of differentiating AFE to an alveolar type II cell phenotype requires the use of the combination of growth factors and ECM proteins. In one embodiment, the combination of growth factors includes FGF-10, EGF, Wnt3a, and KGF. In another embodiment, the combination of growth factors excludes BMP4. With respect to ECM proteins, the cells in one embodiment, can be cultured in the presence of ECM proteins that mimic ECM proteins that exist during embryogenesis for lung development (e.g., collagens, laminin, fibronectin, tenascin, elastin, and a number of proteoglycans and glycosaminoglycans).

Definitive Endoderm

During embryonic development, the tissues of the body are formed from three major cell populations: ectoderm, mesoderm and definitive endoderm. These cell populations, also known as primary germ cell layers, are formed through a process known as gastrulation. Following gastrulation, each primary germ cell layer generates a specific set of cell populations and tissues. Mesoderm gives rise to, for example, blood cells, endothelial cells, cardiac and skeletal muscle, and adipocytes. Definitive endoderm generates, for example, liver, pancreas and lung. Ectoderm gives rise to, for example, the nervous system, skin and adrenal tissues.

Described herein is the demonstration that definitive endoderm can be produced, purified and expanded from stem cells. Thus purified or sub-cultured stem cell-derived definitive endoderm can be used as a platform for differentiation toward lung progenitors (e.g., alveolar type II progenitor cells). In one embodiment, the invention provides a method of generating cell populations comprising definitive endoderm cells from a cell population substantially initially consisting essentially of stem cells, preferably human induced pluripotent stem (iPS) cells.

In one embodiment, the invention provides a method of producing endoderm cells, such as definitive endoderm cells by exposing stem cells such as embryonic stem cells (ES) or iPS cells to an effective amount of at least one compound described herein to differentiate the stem cells into the endoderm cells such as definitive endoderm cells. Differentiated endoderm cells produced by the methods disclosed herein can be differentiated into endoderm derivatives such as pancreas, thymus, liver, stomach, intestine and lung. Another aspect of the present invention relates to a method of producing alveolar type II progenitor cells by exposing endoderm cells, such as definitive endoderm cells to an effective amount of at least one compound described herein to differentiate the definitive endoderm cells into alveolar type II progenitor cells.

Methods of the invention can be used for stimulating differentiation of stem cells into DE cells in medium which is free of serum and free of serum extract. Preferably, such methods are also carried out in the absence of feeder cells and/or feeder cell extracts.

For example, differentiation of stem cells into DE cells can be carried out comprising the steps of: 1) maintaining stem cells in a first culture medium for a period of time, optionally on feeders, in the presence of serum or an extract of serum or in a serum free/serum extract free medium; 2) replacing the first medium with a second serum free medium comprising activin or removing the serum or the serum extract from the first medium and withdrawing the feeders (if present) and adding activin, so that the first medium is free of feeders, serum and serum extract; and 3) subsequently propagating the stem cells in the medium comprising activin in order to obtain cells comprising DE cells.

In one embodiment, directed differentiation of pluripotent cells, e.g., stem cells, into definitive endoderm can be obtained by application of high concentrations of Activin A. Without wishing to be bound by any particular theory, it is believed that the scientific basis for this strategy is that signaling by the morphogen nodal is required for endoderm formation. Activin A activates the same receptor as nodal, but is available as a soluble cytokine.

In one embodiment, generation of definitive endoderm stem cells may be accomplished by adapting a protocol used to develop definitive endoderm from mouse ES cells (Kubo et al, 2004 Development 131: 1651-1662). Preferably, the stem cells are initially cultured without serum in the presence of a high concentration of Activin A (about 50-500 ng/ml, about 75-150 ng/ml, about 100 ng/ml).

One can use any means common to one of ordinary skill in the art to confirm the presence of an endoderm cell, e.g. a definitive endoderm cell produced the methods of the invention. In some embodiments, the presence of endoderm cells can be detected using suitable markers such as those listed in U.S. Pat. No. 7,326,572, which is incorporated herein by reference.

In some embodiments, the presence of definitive endoderm markers, e.g. chemically induced definitive endoderm cells, can be evaluated by detecting the presence or absence of one or more markers indicative of a definitive endoderm cell. In some embodiments, the method can include detecting the positive expression (e.g., the presence) of a marker for definitive endoderm cells. In some embodiments, the marker can be detected using a reagent, e.g., a reagent for the detection of one or more of SOX17, HNF3β (Fox2A), MIXL2, GATA4, GSC, FGF17, VWF, CALCR, FOXQ1, CMKOR1, CRIP1, and the like. In particular, definitive endoderm cells express Sox17 and/or HNF3B, and do not express significant levels of extra-embryonic endoderm markers such as GATA4, SPARC, APF, and DAB. Other positive markers for definitive endoderm cells also include but are not limited to Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, and Rbm35a.

Negative markers (e.g., the absence of significant levels of expression) for definitive endoderm cells include extra-embryonic (EE) endoderm markers such as Gata4, SPARC, APF and DAB, as well as negative markers Zic, Pax6, Flk1 or CD31. Negative markers of definitive endoderm cells are useful for the purposes of negative selection of non-definitive endoderm cells (e.g., selection and discarding cells which express Gata4, SPARC, APF, DAB, Zic, Pax6, Flk1 or CD31) or for identification of cells which do not express these negative markers (e.g. definitive endoderm cells).

A reagent for a marker can be, for example, an antibody against the marker or primers for a RT-PCR or PCR reaction, e.g., a semi-quantitative or quantitative RT-PCR or PCR reaction. Such markers can be used to evaluate whether a definitive endoderm cell has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The progression of a pluripotent stem cell to a definitive endoderm can be monitored by determining the expression of markers characteristic of definitive endoderm cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of definitive endoderm cells as well as the lack of significant expression of markers characteristic of the pluripotent stem cell from which it was derived is determined.

Anterior Foregut Endoderm (AFE)

Lung, esophagus and trachea are derived from anterior foregut endoderm distal to the pouches. The ability to generate populations of anterior foregut/pharyngeal endoderm cells from pluripotent cells would be useful in cell replacement therapy for these tissues, in assays for agents that affect cell growth and differentiation, and in studies on tissue development and differentiation.

The definitive endoderm cells of the present invention may be allowed to differentiate into cells of the anterior foregut endoderm. It has been discovered that although Activin A induces endoderm, Activin A posteriorizes this tissue. Preparation of anterior foregut endoderm thus requires reducing or removing Activin A following formation of definitive endoderm. In certain aspects, the present invention thus provides a method for the formation of a population of cells enriched for anterior foregut endoderm, and the depletion of mid- and posterior endoderm signals.

In one embodiment, the definitive endoderm cell population can then be differentiated into anterior foregut endoderm by culturing the definitive endoderm cells in the presence of the combination of an extracellular matrix (ECM) protein and a culture medium supplemented with an inhibitor of BMP and an inhibitor of TGF-β signaling. Preferably, the inhibitor of BMP is NOGGIN and the inhibitor of TGF-β signaling is SB-431542.

In certain embodiments, the invention thus provides cell populations enriched for anterior foregut endoderm cells. Enriched populations of anterior foregut endoderm comprise at least 25%, at least 50%, at least 75%, at least 90%, at least 95% at least 99% or at least 99.9% anterior foregut endoderm cells.

Endoderm cell populations are characterized and distinguished by markers known in the art. Within definitive endoderm, the embryonic stem cell marker SOX2 reemerges as a marker of anterior foregut endoderm, while CDX2 is a marker of posterior endoderm (hindgut). Prolonged culture of cells induced for 4 to 5 days to form endoderm by Activin A leads to an increase of CDX2 and a loss of SOX2, suggesting posteriorization in these conditions. Anteriorization of definitive endoderm may be accomplished by withdrawing or blocking Activin A and adding anteriorizing morphogens. Preferred anteriorizing morphogens are inhibitors of BMP and TGF-β signaling. Inhibitors of BMP and TGF-β signaling may be used singly or in combination. Preferably, inhibitors of BMP and TGF-β signaling are used in combination. Examples of BMP inhibitors are Noggin, Chordin, and follistatin. A preferred inhibitor of BMP is Noggin. Examples of inhibitors of TGF-β signaling are Ly364947 (SD208), SM16, SB-505124, SB-431542, and anti-TGF-β antibodies. A preferred inhibitor of TGF-β signaling is SB-431542. In a preferred embodiment, a combination of Noggin and SB-431542 is used to induce anteriorization of definitive endoderm. In certain embodiments, a combination of Noggin and SB-431542 is added for about 2 days in culture to induce anteriorization of definitive endoderm. Anteriorization of definitive endoderm with Noggin and SB-431542 may be confirmed by, for example, detecting expression of, for example, one or more of SOX2, TBX1 (pharynx), PAX9 (pharynx, thymus), FOXP2 (lung, airway epithelium), DLX3 (esophagus), FOXA2 (definitive endoderm), and/or SOX7 (early endodermal marker); and optionally detecting lack of expression of PAX6 (ectoderm) and/or BRACHYURY (mesoderm).

In certain embodiments, the invention provides a method of deriving anterior foregut endoderm comprising culturing definitive endoderm with an inhibitor of BMP or an inhibitor of TGF-β signaling and in the absence of Activin A. In preferred embodiments, definitive endoderm is cultured with both an inhibitor of BMP and an inhibitor of TGF-β signaling and in the absence of Activin A.

In some embodiments, an inhibitor of BMP is Noggin. In some embodiments Noggin is present in cultures at a concentration of about 1 ng/ml to 10 μg/ml, 10 ng/ml to 1 μg/ml, 10 ng/ml to 500 ng/ml, 10 ng/ml to 250 ng/ml, or 10 ng/ml to 100 ng/ml. In preferred embodiments, Noggin is present in cultures at a concentration of about 25 ng/ml to 150 ng/ml, 50 ng/ml to 150 ng/ml or 75 ng/ml to 150 ng/ml. In most preferred embodiments, Noggin is present in cultures at a concentration of about 100 ng/ml.

In some embodiments, an inhibitor of TGF-β is SB-431542. In some embodiments of the methods described herein, SB-431542 is present in cultures at a concentration of about 0.1 μM to 100 mM, 1 μM to 10 mM, 1 μM to 500 μM, 1 μM to 250 μM, or 1 μM to 100 μM. In most preferred embodiments, SB-431542 is present in cultures at a concentration of about 10 mM.

Also preferred are embodiments wherein cultures used in the methods of the invention comprise Noggin at a concentration of about 75 ng/ml to 150 ng/ml and SB-431542 at a concentration of about 500 μM to 10 mM. Preferably, Noggin is at a concentration of about 200 ng/ml and SB-431542 is at a concentration of about 10 mM.

With respect to ECM proteins, the definitive endoderm cell population can be cultured in the presence of ECM proteins. That is, the present invention is based on the discovery that culturing definitive endoderm cells in the presence of the combination of ECM proteins and culture medium supplemented with NOGGIN and SB-431542 resulted in highly efficient anterior forgut endoderm differentiation. In one embodiment, the ECM proteins useful for anterior forgut endoderm differentiation mimic ECM proteins that exist during embryogenesis for lung development (e.g., collagens, laminin, fibronectin, tenascin, elastin, and a number of proteoglycans and glycosaminoglycans).

In another embodiment, the present invention provides a method of culturing cells in the presence of ECM proteins on a surface (e.g., two-dimensional or three-dimensional) in a suitable growth medium. In one embodiment, the ECM is coated on the surface of a culturing apparatus.

In another embodiment, the present invention includes a tissue culture system. In various aspects, the culture system is composed of the ECM compositions described herein, such as being included in two-dimensional or three-dimensional support materials. In another aspect, the ECM compositions described herein serve as a support or two-dimensional or three-dimensional support for the growth of various cell types. For example, the culture system can be used to support the growth of stem cells. In one aspect, the culture system can be used to support the differentiation of stem cells. In yet another embodiment, the culture system can be used to support the differentiation of definitive endoderm cells into cells of the anterior foregut endoderm.

ECM is known to be secreted by certain cells and is comprised mainly of fibrous proteins, polysaccharides, and other minor constituents. Its components include structural elements such as collagen and elastin, adhesive proteins such as the glycoproteins fibronectin, laminin, vitronectin, thrombospondin I and tenascins, as well as proteoglycans such as decorin, biglycan, chondroitin sulfate and heparin sulfate and glycosaminoglycans (GAG) such as hyaluronic acid (HA).

In one embodiment, the ECM compositions can include any or all of the following: fibronectin, fibrillin, laminin, elastin, members of the collagen family (e.g., collagen I, III, and IV), glycosaminoglycans, ground substance, reticular fibers and thrombospondin. Preferably, human ECM is used for culturing the definitive endoderm. In one embodiment, human ECM includes collagens, laminin, fibronectin, tenascin, elastin, and a number of proteoglycans and glycosaminoglycans.

In another embodiment, it is desirable to culture the cells on a solid support that comprises a reconstituted basement membrane, wherein the membrane can be obtained by being extracted and prepared from a suitable cell tissue that is contained in the thin, membranous extracellular matrix present below the cell layer in vivo and contains proteins and glycoproteins such as laminin, collagen IV and heparin sulphate proteoglycan as well as various cell growth factors and activating factors, etc.

In one embodiment, the predominant major extracellular matrix component is fibrillar collagen, particularly collagen type I. However, other fibrillar and non-fibrillar collagens, including collagen types II, III, IV, V, VI, VII, VIII, IX, X, XI, XII, XIII, XIV, XV, XVI, XVII, XVIII, XIX, and others.

The ECM compositions of the present invention may be processed in a variety of ways. Accordingly, in one embodiment, the present invention includes a tissue culture system. In various aspects, the culture system is composed of the ECM compositions described herein. The ECM compositions of the present invention may be incorporated into the tissue culture system in a variety of ways. For example, compositions may be incorporated as coatings, by impregnating three-dimensional scaffold materials as described herein, or as additives to media for culturing cells. Accordingly, in one aspect, the culture system can include three-dimensional support materials impregnated with any of the ECM compositions described herein, such as growth factors or embryonic proteins.

Alveolar Type II Progenitor Cells

Cells that are able to differentiate into the alveolar epithelial system are cells involved in tissue repair after a lung injury, and are therefore clinically very important cells for regenerative medicine, etc. Furthermore, these cells are also useful as materials for discovering new markers for identifying human lung tissue stem cells, and it is believed that analyzing the differentiation signals, etc. of these cells may lead to the discovery of new drugs.

In one embodiment, the anterior foregut endoderm cells of the invention can be induced to differentiate into a desired cell type by culturing the cells in an appropriate differentiation medium.

Differentiation can be induced using one or more differentiation agents, including without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate).

In one embodiment, the anterior foregut endoderm cells of the invention can be induced to differentiate into cells having a lung phenotype. For example, anterior foregut endoderm cells can be induced to differentiate into type II alveolar cells, which also are known as type II pneumocytes. A medium can be used that contains one or more of pituitary extract (e.g. a bovine pituitary extract), steroid hormones (e.g. hydrocortisone, or a salt thereof such as the acetate), growth factors (e.g., epidermal growth factor, preferably human epidermal growth factor), catecholamines (e.g., epinephrine, either in racemic or enantiomeric form), iron-binding proteins (e.g., a transferrin), insulin, vitamins (e.g., retinoic acid), thyroid hormones (e.g., triiodothyronine), serum albumins (e.g., bovine or human serum albumin, including recombinant preparations), antibiotics (e.g., aminoglycoside antibiotics, such as gentamicin), and/or antifingals (e.g., amphotericin-B). For example, a medium can include hydrocortisone, epidermal growth factor, insulin, triiodothyronine, transferrin, and bovine serum albumin and in some embodiments, further can include retinoic acid, pituitary extract, and epinephrine. SAGM™ medium from Cambrex (catalog CC-3118) is particularly useful for differentiating anterior foregut endoderm cells into type II alveolar cells.

The present inventors have been able to obtain, through use of appropriate differentiation factors, a pure population of lung cells. Preferably, the lung cell is a distal lung cell type, preferably an alveolar-type cell, more preferably, a type-I or type-II alveolar-type cell.

In some embodiments, the methods of the invention efficiently induce direct differentiation of stem cells into alveolar type II cells. In some embodiments, the method results in a sufficiently pure population of alveolar type II cells (e.g., at least 95% alveolar type II phenotype).

In one embodiment, the anterior foregut endoderm cells of the invention can be induced to differentiate into cells that exhibit at least one characteristic of an alveolar type II cell. For example, the anterior foregut endoderm cells can be cultured in the presence of a differentiation medium comprising FGF-10, EGF, Wnt3a, and KGF for a period of time sufficient for differentiation towards an alveolar type II cell phenotype In some embodiments, an agonist of Wnt signaling is Wnt3a; others can also be used, as described herein. For use in the methods described herein, Wnt3a is present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, Wnt3a is present in cultures at a concentration of about 25 ng/ml to 150 ng/ml, 50 ng/ml to 150 ng/ml or 75 ng/ml to 150 ng/ml. In further preferred embodiments, Wnt3a is present in cultures at a concentration of about 100 ng/ml.

In some embodiments, agonists of FGF signaling are FGF7 or FGF10; others can also be used, as described herein. For use in the methods described herein, FGF7 or FGF10 are present in cultures at a concentration of about 1 ng/ml to 10 µg/ml, 10 ng/ml to 1 µg/ml, 10 ng/ml to 500 ng/ml, 10 ng/ml to 250 ng/ml, or 10 ng/ml to 100 ng/ml. In preferred embodiments, FGF7 or FGF10 are present in cultures at a concentration of about 25 ng/ml to 150 ng/ml, 50 ng/ml to 150 ng/ml or 75 ng/ml to 150 ng/ml. In most preferred embodiments, both FGF7 and FGF 10 are present in cultures at a concentration of about 10 ng/ml.

Exemplary stem cell differentiated alveolar type II cells appear morphologically normal, express the characteristic surfactant proteins A, B, and C, CFTR and α-1AT RNA as well as synthesize and secrete complement proteins C3 and C5. Thus, a unique approach is provided to reliably generate significant quantities of sufficiently pure stem cell-derived alveolar type II cells that can be used therapeutically to reconstitute damaged lung alveolus and other lung diseases or disorders such as, but not limited to, genetic diseases that affect the lung.

Preferably, the cells form histiotypic alveolar-like structures, comprised of differentiated distal epithelial cells (proSpC expressing) forming ductal structures. Thus, the implanted cells will develop characteristics that liken it to the surrounding tissue. Using these methods, the biological scaffolding can augment the tissue; the biological scaffolding of the invention can be used for tissue engineering and in any conventional tissue engineering setting.

In one embodiment, the present methods result in direct differentiation of stem cells into alveolar type II cells which contrasts with previous attempts at differentiation of alveolar type II cells from stem cells, in which multiple steps were used to derive alveolar type II cells from stem cells through embryonic body formation. Previous approaches require prolonged time periods to develop the endoderm from which the alveolar type II cells are derived, and yet in the end the produce scarcely detectable numbers of alveolar type II cells in mixed cell populations. Therefore, in addition to providing sufficiently pure and numerous alveolar type II cells, embodiments of the present methods decrease the time and effort in generating stem cell-derived alveolar type II cells and facilitate their therapeutic and clinical use.

Differentiation to lung cells (e.g., alveolar type II cells) can be confirmed, for example, by a lung morphology as assessed by light microscopy and the presence of lamellar bodies and microvesicular bodies as assessed by transmission electron microscopy. Lamellar bodies are secretory lysosomes that serve as the storage form of lung surfactant, surfactant protein C (SPC), which is an integral membrane protein that is expressed only in alveolar type II cells. The presence of SPC mRNA can be detected by reverse-transcriptase PCR and the presence of SPC protein can be detected by immunofluorescence staining.

Methods

The invention relates to the discovery that stem cells (e.g., iPS cells) can be differentiated to alveolar type II cells by way of the definitive endoderm. For example in one embodiment, the invention provides a method of differentiating a population of stem cells into a population of lung cells comprising: 1) inducing a stem cell into a cell of the definitive endoderm; 2) inducing the cell of the definitive endoderm into an anterior foregut endoderm cell; 3) inducing the anterior foregut endoderm cell into a lung cell, thereby differentiating a stem cell into a lung cell. The cells of the invention are useful for investigating lung developmental biology. In addition, the cells of the invention are useful for among other things, drug discovery, toxicity testing, disease pathology, and the like. Accordingly, the invention provides methods and compositions for the generation of vascularized pulmonary tissues as a form of regenerative medicine.

The production of a population of in vitro cultured cells of alveolar epithelial type II cell lineage derived from at least one stem cell includes culturing at least stem cell in vitro according to the method of the invention in order to produce differentiated cells, preferably without formation of an embryonic body. In one embodiment, the method of production further includes identifying the differentiated cells of alveolar epithelial type II cell phenotype by detecting expression of at least one biomarker of alveolar epithelial type II cells, and isolating the differentiated cells having alveolar epithelial type II cell phenotype. In some cases, this may include selecting a purified population of differentiated cells wherein at least 95%, preferably at least 96%, preferably at least 97%, more preferably at least 98%, more preferably at least 99% of the cells have alveolar epithelial type II cell phenotype.

The cells of the invention and cells derived therefrom can be derived from, inter alia, humans, primates, rodents and birds. Preferably, the cells of the invention are derived from mammals, especially mice, rats and humans. Stem cells from which the of alveolar epithelial type II cells are derived may be either wild-type or genetically modified stem cells.

The cells of the present invention, whether grown in suspension or as adherent cell cultures, are grown in contact with culture media.

Culture media used in the present invention preferably comprise a basal medium, optionally supplemented with additional components.

Basal medium is a medium that supplies essential sources of carbon and/or vitamins and/or minerals for the cells. The basal medium is generally free of protein and incapable on its own of supporting self-renewal/symmetrical division of the cells.

Preferably, the suitable cell is isolated from a mammal, more preferably a primate and more preferably still, a human. The cells useful in the methods of the present invention are isolated using methods discussed herein, for example in the Examples section, or by any method known in the art. Following isolation, the suitable cells are cultured in a culture medium. Media formulations that support the growth of cells include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with nonessential amino acids), and the like.

It is further recognized that additional components may be added to the culture medium. Such components include, but are not limited to, antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 μg/ml. However, the invention should in no way be construed to be limited to any one medium for culturing the cells of the invention. Rather, any media capable of supporting the cells of the invention in tissue culture may be used.

In certain embodiments, culture media used in the invention do not contain any components which are undefined (e.g. serum and/or feeder cells), that is to say components whose content is unknown or which may contain undefined or varying factors that are unspecified. An advantage of using fully defined media, free of serum and free of serum extracts, is that efficient and consistent protocols for culture and subsequent manipulation of the cells of the invention and cells derived therefrom can be obtained.

Typical substrates for culture of the cells in all aspects of the invention are culture surfaces recognized in this field as useful for cell culture, and these include surfaces of plastics, metal, composites, though commonly a surface such as a plastic tissue culture plate, widely commercially available, is used. Such plates are often a few centimeters in diameter. For scale up, this type of plate can be used at much larger diameters and many repeat plate units used.

The culture surface may further comprise a cell adhesion protein, usually coated onto the surface. Receptors or other molecules present on the cells bind to the protein or other cell culture substrate and this promotes adhesion to the surface and promotes growth.

In certain embodiments, the cultures of the invention are preferably adherent cultures, i.e. the cells are attached to a substrate.

In some instances, the cells of the invention can be cultured on a decellularized tissue, preferably a decellularized lung tissue. In some instances, cells of the invention are cultured on the decellularized tissue for regeneration of lung tissue. An example of a decellularized lung tissue is disclosed in PCT/US2010/023213, the content of which is incorporated herein by reference in its entirety.

In one embodiment, the invention provides cells that "seed" the decellularized tissue scaffold. The cells can differentiate in vitro by culturing the cells on the scaffold in the presence of an appropriate differentiation medium. Differentiated cells can be identified by their gross morphology and by the connections they form with other cells. For example, cells that differentiate into lung cells can develop complex morphology resembling bronchioles.

The present invention also provides an in vivo method of repairing injured or diseased alveolar epithelial tissue in the lung of a mammal is provided in accordance with some embodiments. Such method comprises transplanting into a lung that contains injured or diseased alveolar epithelial tissue, a population of differentiated stem cells, or progeny thereof, at least 95% of which have alveolar epithelial type II phenotype. The population of cells is prepared in accordance with a method described herein, and is effective to repair at least a portion of the injured or diseased alveolar epithelial tissue. In some embodiments, the mammal suffers from a genetic disease affecting alveolar epithelial tissue in the lung, and said therapeutic transgene encodes a gene product for ameliorating the detrimental effects of said genetic disease in said alveolar epithelial tissue. In some embodiments, at least one differentiated stem cell, or progeny thereof, comprises a therapeutic transgene operably linked to a cell-specific promoter, wherein the transgene encodes a therapeutic gene product. In some embodiments, an above-described population of cells is transplanted directly to injured or diseased alveolar epithelial tissue in said lung. In some embodiments, transplanting the population of cells comprises administering them into the lung endotracheally via oropharynx intubation.

In one embodiment, the methods of the invention provides the generation of lung progenitor cells from differentiated cultures of stem cells. Moreover, with the recent discovery that iPS cells can be created from dermal skin fibroblasts, investigations have begun to examine the possibility of generating lung progenitor epithelial cells from somatic cells. If these efforts succeed, patient-specific iPS cells could be obtained, thereby avoiding the immune rejection problems that might occur if heterologous sources of embryonic stem cells were employed. Moreover, iPS cells offer the possibility of generating gene-corrected, patient-specific lung progenitor cells from individuals with genetic diseases affecting the lung, including cystic fibrosis, alpha-1-antitrypsin deficiency, and surfactant protein deficiencies.

Many embodiments of the present compositions and methods efficiently induce direct differentiation of human stem cells into alveolar epithelial type II cells without EB formation and also produce a highly pure population of human alveolar epithelial type II cells. In some embodiments the method results in a clonal population of alveolar epithelial type II phenotype cells sufficiently pure (e.g., at least 95% and in many cases at least 99% alveolar epithelial type II phenotype) suitable for implantation into a mammalian host lung tissue without significant risk of producing a teratoma.

Transplantation of the stem cell-derived alveolar epithelial type II cells, produced using embodiments of the described methods reversed or prevented acute lung injury when transplanted 1 or 2 days following injury, as demonstrated by recovery of body weight and arterial blood oxygen saturation, decreased collagen deposition, and increased survival. Interestingly, some injured lung alveolar epithelium regions appeared healthy after transplantation of the stem cell-derived alveolar epithelial type II cells, produced using embodiments of the described methods, despite having no observable engrafted stem cell-derived alveolar epithelial type II cells. This suggests that stem cell-derived alveolar epithelial type II cells, produced using embodiments of the described methods, may provide paracrine repair/protection to injured lung epithelium, such as, but not limited to, the release of anti-inflammatory mediators such as IL-10, angiopoietin-1, and keratinocyte growth factor.

In some embodiments, the alveolar type II epithelial cells derived from stem cells (such as but not limited to human iPS cells, as used in the examples) is used therapeutically in the treatment of lung injury. Therapeutic activity is demonstrated herein using alveolar type II epithelial cells derived from stem cells in an animal model of acute lung injury. When transplanted into lungs of mice subjected to bleomycin-induced acute lung injury, stem cell derived-alveolar epithelial type II cells behaved as normal primary alveolar epithelial type II cells, differentiating into cells expressing phenotypic markers of alveolar type I epithelial cells. Without experiencing tumorigenic side effects, lung injury was abrogated in mice transplanted with stem cell derived-alveolar epithelial type II cells, demonstrated by recovery of body weight and arterial blood oxygen saturation, decreased collagen deposition, and increased survival. Therefore, transplantation of stem cell derived-alveolar epithelial type II cells shows promise as an effective therapeutic to treat acute lung injury and related disorders.

In one embodiment, the invention provides a method of repairing injured or diseased alveolar epithelial tissue in the lung of a mammal comprising transplanting a population of differentiated stem cells, or progeny thereof of the invention into the mammal. Preferably, cells of the invention are transplanted at a site comprising injured or diseased alveolar epithelial tissue. In another embodiment, the cells of the invention are transplanted directly into the lung of the mammal. In one embodiment, the population of differentiated stem cells, or progeny thereof of the invention is at least 95%, preferably at least 96%, preferably at least 97%, more preferably at least 98%, more preferably at least 99% of which exhibit alveolar epithelial type II phenotype, wherein the population of cells is prepared in accordance with the methods of the invention, and is effective to repair at least a portion of the injured or diseased alveolar epithelial tissue at the site. The differentiated stem cell, or progeny thereof, may comprise a transgene, which encodes a desirable gene product (e.g., a therapeutic protein or peptide), operably linked to a cell-specific promoter.

In one embodiment, the invention provides a method of treating a genetic disease affecting alveolar epithelial tissue in the lung of a mammal comprising transplanting a population of differentiated stem cells, or progeny thereof of the invention into the mammal. Preferably, the cells of the invention are transplanted into the lung, at a site comprising alveolar epithelial tissue detrimentally affected by the genetic disease. The differentiated stem cell, or progeny thereof of the invention can comprise a transgene that encodes a gene product which ameliorates the genetic disease or its detrimental effects in the alveolar epithelial tissue at least at the site of implantation when expressed in vivo. The cells of the invention may comprise a transgene operably linked to a cell-specific promoter, wherein the transgene encodes a therapeutic gene product.

Methods of treatment of the diseases encompassed by the invention can comprise the transplantation of single cells, cell lines, compositions, or cell populations of the invention into a mammal in need thereof. Preferably, the mammal is a human.

In one embodiment, the cells of the invention can be used to assay the effectiveness of inductive or blocking factors on the differentiation of the cells of the invention. Such an assay may comprise contacting a cell of the invention (i.e. as present in the compositions, cell lines, and populations, or a single cell) with the factor to be tested. The effect of the factor on the differentiation of the cell can be suitably assessed by determining the marker profile of the resultant cells, i.e. to show whether the cells have a similar marker profile to the cells of the invention, or whether these markers have been lost. The cells of the invention are also suitable for assaying pharmaceuticals, for example, the treatment of lung disease.

Genetic Modification

The cells of the invention can be used to treat a lung disease including but not limited to emphysema, bronchiolitis obliterans, and cystic fibrosis. For example, cells and be delivered to a recipient via tracheal instillation, inhalation, or injection, among other ways. Such cells that are expanded in culture can be used to affect therapy in the recipient.

In the context of gene therapy, the cells of the invention can be treated with a gene of interest prior to delivery of the cells into the lung of a recipient. In some cases, such cell-based gene delivery can present significant advantages of other means of gene delivery to the lung, such as inhalation of adenoviral gene delivery vectors. This superiority of cell-based gene delivery to a host stems from the observation that inhaled gene delivery vectors typically result in poor efficiency of cellular transduction, due to barriers imposed by the mucous layer and the host immune system. Delivery of a therapeutic gene that has been pre-inserted into cells avoids the problems associated with penetration of gene therapy vectors into recipient lung cells.

Accordingly, the invention provides the use of genetically modified cells that have been cultured according to the methods of the invention. Genetic modification may, for instance, result in the expression of exogenous genes ("transgenes") or in a change of expression of an endogenous gene. Such genetic modification may have therapeutic benefit. Alternatively, the genetic modification may provide a means to track or identify the cells so-modified, for instance, after implantation of a composition of the invention into an individual. Tracking a cell may include tracking migration, assimilation and survival of a transplanted genetically-modified cell. Genetic modification may also include at least a second gene. A second gene may encode, for instance, a selectable antibiotic-resistance gene or another selectable marker.

Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, His$_6$, and the like).

When the purpose of genetic modification of the cell is for the production of a biologically active substance, the substance will generally be one that is useful for the treatment of a given disorder. For example, it may be desired to genetically modify cells so that they secrete a certain growth factor product associated with bone or soft tissue formation. Growth factor products to induce growth of other, endogenous cell types relevant to tissue repair are also useful. For instance, growth factors to stimulate endogenous capillary and/or microvascular endothelial cells can be useful in repair of soft tissue defect, especially for larger volume defects.

The cells of the present invention can be genetically modified by having exogenous genetic material introduced into the cells, to produce a molecule such as a trophic factor, a growth factor, a cytokine, and the like, which is beneficial to culturing the cells. In addition, by having the cells genetically modified to produce such a molecule, the cell can provide an additional therapeutic effect to the mammal when transplanted into a mammal in need thereof. For example, the genetically modified cell can secrete a molecule that is beneficial to cells neighboring the transplant site in the mammal.

The cells of the invention may be genetically modified using any method known to the skilled artisan. See, for instance, Sambrook et al. (2001, Molecular Cloning: A Laboratory Manual, Cold Spring Harbor Laboratory Press, Cold Spring Harbor, N.Y.), and in Ausubel et al., Eds, (1997, Current Protocols in Molecular Biology, John Wiley & Sons, New York, N.Y.). For example, a cell may be exposed to an expression vector comprising a nucleic acid including a transgene, such that the nucleic acid is introduced into the cell under conditions appropriate for the transgene to be expressed within the cell. The transgene generally is an expression cassette, including a polynucleotide operably linked to a suitable promoter. The polynucleotide can encode a protein, or it can encode biologically active RNA (e.g., antisense RNA or a ribozyme). Thus, for example, the polynucleotide can encode a gene conferring resistance to a toxin, a hormone (such as peptide growth hormones, hormone releasing factors, sex hormones, adrenocorticotrophic hormones, cytokines (e.g., interferins, interleukins, lymphokines, etc.), a cell-surface-bound intracellular signaling moiety (e.g., cell adhesion molecules, hormone receptors, etc.), a factor promoting a given lineage of differentiation (e.g., bone morphogenic protein (BMP)), etc.

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICP0-IEEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit .beta.-globin regulatory elements), constitutively active promoters (e.g., the .beta.-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated virus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). The choice of vector will largely determine the method used to introduce the vector into the cells (e.g., by protoplast fusion, calcium-phosphate precipitation, gene gun, electroporation, DEAE dextran or lipid carrier mediated transfection, infection with viral vectors, etc.), which are generally known in the art.

Examples of techniques sufficient to direct persons of skill through in vitro amplification methods, including the polymerase chain reaction (PCR), the ligase chain reaction (LCR), and other DNA or RNA polymerase-mediated techniques are found in Sambrook et al., MOLECULAR CLONING: A LABORATORY MANUAL, volumes 1-3 ($3^{rd}$ ed., Cold Spring Harbor Press, N Y 2001).

Once the nucleic acid for a protein is cloned, a skilled artisan may express the recombinant gene(s) in a variety of lung cells. It is expected that those of skill in the art are knowledgeable in the numerous expression systems available for expressing the desired transgene.

Bioreactor

The invention provides a system (e.g., a bioreactor) for culturing the cells of the invention that have been introduced to a decellularized lung. The bioreactor enables the maintenance of cell viability, cellular differentiation state, and lung morphology. The bioreactor of the invention incorporates key features of the vivo environment. The bioreactor can be designed to allow modifications for optimizing decellularization and/or recellularization processes.

In one embodiment, the bioreactor is capable of perfusing media through the vasculature at a rate specified by the user and within the physiological flow and pressure levels of a mammal. In another embodiment, the bioreactor is capable of ventilating the tissue (e.g., lung) with air or media through the trachea. Preferably, negative pressure ventilation is used in order to be consistent with normal physiological conditions, though ventilation using positive pressure can also be done. In yet another embodiment, the bioreactor is capable of allowing different media types to bathe the vascular and airway compartments of the tissue. In another embodiment, the bioreactor allows for gas exchange into the culture medium, while simultaneously meeting the desired requirements for ventilation. In another embodiment, the bioreactor has ports to allow for pressure measurements, for example measurements of the pulmonary artery and tracheal pressures. Preferably, pressures are within normal physiological values. In another embodiment, the bioreactor has a means of allowing media exchange on a periodic basis.

The bioreactor of the invention generally includes at least one cannulation device for cannulating a tissue, a perfusion apparatus for perfusing media through the cannula(s), and means (e.g., a containment system) to maintain a sterile environment for the organ or tissue. A cannulation device generally includes size-appropriate hollow tubing for introducing into a vessel, duct, and/or cavity of a tissue. Typically, one or more vessels, ducts, and/or cavities are cannulated in a tissue. A perfusion apparatus can include a holding container for the liquid (e.g., a cellular disruption medium) and a mechanism for moving the liquid through the organ (e.g., a pump, air pressure, gravity) via the one or more cannulae. The sterility of a tissue during decellularization and/or recellularization can be maintained using the methods discussed elsewhere herein.

The bioreactor for can be used to recellularize tissues as described herein. The process can be monitored for certain perfusion characteristics (e.g., pressure, volume, flow pattern, temperature, gases, pH), mechanical forces (e.g., ventricular wall motion and stress), and electrical stimulation (e.g., pacing). The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the bioreactor and/or the tissue. Sonomicromentry, micromanometry, and/or conductance measurements can be used to acquire pressure-volume. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue; and/or the biological activity of a recellularizing tissue. In addition to having sensors for monitoring such features, a system for recellularizing a tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

The bioreactor is capable of providing sufficient nutrient supply and mechanical stimulation to the lung tissue in order to support cell survival and differentiation. The bioreactor can be used for in vitro lung tissue culture and for engineered lung tissue culture. Preferably, the bioreactor is used to culture engineered lung tissue using the decellularized lung scaffolds in combination with the cells of the invention.

The development of a bioreactor capable of the in vitro culture of true 3-dimensional segments of lung tissue is an important step in the development of clinically useful engineered lung tissue. For example, growth and maturation of the engineered lung tissue can take place in the bioreactor prior to implantation of the engineered lung into a recipient, thereby enhancing the functionality of the final implanted lung tissue in vivo. In addition, the bioreactor for in vitro lung culture can be used to assist the study of pulmonary biology, physiology, and development. That is, the interactions of lung endothelial and epithelial cells to form the alveolar-capillary barrier can be studied using the engineered lung tissue and bioreactor of the invention. A skilled artisan would be able to study lung behavior in a more controlled environment than the various animal models currently used. The engineered lung tissue and bioreactor could also be used for pharmacologic testing and investigation in human or animal tissue before proceeding to time-consuming and costly human or animal trials.

Administration

The invention contemplates use of the cells of the invention in both in vitro and in vivo settings. Thus, the invention provides for use of the cells of the invention for research purposes and for therapeutic or medical/veterinary purposes. In research settings, an enormous number of practical applications exist for the technology. One example of such applications is use of the cells of the invention in an ex vivo cancer model, such as one to test the effectiveness of various ablation techniques (including, for example, radiation treatment, chemotherapy treatment, or a combination) in a lab, thus avoiding use of ill patients to optimize a treatment method. For example, one can attach a recently removed lung to a bioreactor and treat the lung to ablate tissue. Another example of an in vivo use is for tissue engineering.

The invention also provides a method of alleviating or treating a lung defect in a mammal, preferably a human. The method comprises administering to the mammal in need thereof a therapeutically effective amount of a composition comprising the cells of the invention, thereby alleviating or treating the lung defect in the mammal.

The cells of the present invention have use in vivo. Among the various uses, mention can be made of methods of in vivo treatment of subjects (used interchangeably herein with "patients", and meant to encompass both human and animals). In general for certain embodiments, methods of treating subjects comprise implanting a cell of the invention into or on the surface of a subject, where implanting of the cell results in a detectable change in the subject. The detectable change can be any change that can be detected using the natural senses or using man-made devices. While any type of treatment is envisioned by the present invention (e.g., therapeutic treatment of a disease or disorder, cosmetic treatment of skin blemishes, etc.), in many embodiments, the treatment is a therapeutic treatment of a disease, disorder, or other affliction of a subject. As such, a detectable change may be detection of a change, preferably an improvement, in at least one clinical symptom of a disease or disorder affecting the subject. Exemplary in vivo therapeutic methods include regeneration of organs after treatment for a tumor, preparation of a surgical site for implantation of a medical device, skin grafting, and replacement of part or all of a tissue or organ, such as one damaged or destroyed by a disease or disorder. In view of the fact that a subject may be a human or animal, the present invention has both medical and veterinary applications.

The invention also provides methods of treating a patient by implanting the cells of the invention into a mammal in need thereof. In some instances, the cells of the invention comprise suitable cells, for example alveolar epithelial type II cells. However, the invention should not be limited to any particular type of cells. After implantation, the grafted cells can respond to environmental cues that will cause it to develop characteristics of the endogenous tissue. Preferably, the cells form histiotypic alveolar-like structures, comprised of differentiated distal epithelial cells (proSpC expressing) forming ductal structures. Thus, the implanted cells will develop characteristics that liken it to the surrounding tissue. Using these methods, the biological scaffolding can augment the tissue; the biological scaffolding of the invention can be used for tissue engineering and in any conventional tissue engineering setting.

Accordingly, the invention encompasses tissue regeneration applications. The objective of the tissue regeneration therapy approach is to deliver high densities of repair-competent cells (or cells that can become competent when influenced by the local environment) to the defect site in a format that optimizes both initial wound mechanics and eventual neotissue production. The composition of the instant invention is particularly useful in methods to alleviate or treat lung tissue defects in individuals. Advantageously, the composition of the invention provides for improved lung tissue regeneration. Specifically, the tissue regeneration is achieved more rapidly as a result of the inventive composition.

Advantageously, the compositions and methods of the invention represent an improvement over prior art methods. Preferably the composition for use in treating a lung tissue defect comprises alveolar epithelial type II cells as described elsewhere herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Differentiation and Characterization of Alveolar Type II Cells from Human Induced Pluripotent Stem Cells The experiments presented herein were designed to explore whether lung tissue can be regenerated in vitro. A relatively homogeneous population of alveolar epithelial type II (AETII) and type I cells (AETI) was generated from human iPS cells which had phenotypic properties similar to mature human alveolar type II and type I cells. Up to 97% of cells were positive for surfactant protein C, 95% for Mucin-1, 93% for surfactant protein B, and 89% for the epithelial marker, CD54. Additionally, exposing AETII to a Wnt/β-catenin inhibitor (e.g., IWR-1) changed the iPSC-AETII like phenotype to a predominantly AETI like phenotype. Of the cells that were AET1 cells, more than 90% of were positive for the type I markers, T1α and caveolin-1. Acellular lung matrices were prepared by treating whole rat or human adult lungs with decellularization reagents, followed by seeding these matrices with alveolar cells derived from human iPS cells. Under appropriate culture conditions, these progenitor cells adhered to and proliferated within the 3D lung tissue scaffold, and displayed markers of differentiated pulmonary epithelium.

The materials and method employed in these experiments are now described.

Chemical and Reagents

Mouse embryonic fibroblasts (MEFs) (GSC-6201) were purchased from Global stem, Matrigel (354277) were purchased from BD, Recombinant human WNT3a (5036WN) was purchased from R&D. Dispase (07923) was obtained from Stem Cell Technology. Keratinocyte growth factor (KGF) (PHG0094), fibroblast growth factor 10 (FGF-10) (PHG0204), epidermal growth factor (EGF) (PHG0311), human basic fibroblast growth factor (bFGF) (13256-029), NOGGIN (PHC1506), Activin A (PHG9014), knock out serum replacement (108280280), Superscript first strand synthesis system for RT-PCR (18080-051) were purchased from Invitrogen. Dulbecco's Modified Eagle Medium: Nutrient Mixture F-12 (DMEM/F-12) (11330-032), Dulbecco's Modified Eagle Medium (DMEM) (11905-092), RPMI 1640 (11875-093), IMDM (12440-053), non-essential amino acids (1140-050), L-glutamine (25030164), sodium pyruvate (11360-070), 2-mercaptoethanol (21985-023), B27 supplement (17504-044), Trypsin (25200-056), Penicillin-streptomycin (15140-122) fetal bovine serum (FBS) were purchased from GIBCO by life technology. Retinoic acid (R2625) gelatin (G1393), SB431542(54317), human ECM protein (E0282), IWR-1(I0161), human collagen type I (C7624) and IV (C7521), human fibronectin (F0895), human ECM protein (E0282), CHAPs C3023), Benzonase (E1014), Sodium Deoxycholate (D6750), Elastase (E8140) Triton X-100 (T9284), were purchased from Sigma-Aldrich. Sodium Nitroprusside Dihydrate (71778) was obtained from Fluka. DNase I (LS006333) was purchased from Worthington Biochemical Corporation. Small Airway Growth Medium (SAGM) (CC-3119), Amphotericin B (17836R) was purchased from Lonza. Human SPC ELISA kit (E01S0168) was obtained from Life Science Advanced Technologiest Inc. Peracetic acid or PAA (P05020) was obtained from Pfalz & Bauer. Fetal bovine serum (FBS) (SH30071.03) was obtained from Hyclone. iQ™ SYBR Green Supermix (170-8882) was obtained from Bio-Rad. All antibodies were used in this study are listed in Table 1.

TABLE 1

List of antibodies used in staining, flow cytometry and western blot for various experiments

| Primary Antibodies | | | |
| --- | --- | --- | --- |
| Antigen | Type | Provider (Cat #) (lot #) | Application |
| Beta-actin | Monoclonal | Abcam (Cat# ab8226, Lot# GR88207-1) | WB |
| Caspase3 | Rabbit polyclonal | Abcam (Cat# ab13847, Lot# GR62173-2) | IHC |
| CCSP | Rabbit polyclonal | Millipore (Cat# 07-623, Lot# 1972321) | IHC |
| CCSP | Goat polyclonal | Biovender (Cat# RD81022220, Lot# RD2412) | IHC |
| CD54-PE | Mouse Monoclonal | BD Pharmingen (Cat# 560971, Lot# 10609) | FC |
| CXCR4-APC | Monoclonal | BD Pharmingen (Cat# 560936, Lot# 41560) | FC |
| Cytokeratin-5 | Rabbit polyclonal | Abbiotec (Cat# 251431, Lot# 11092101) | IHC |
| FoxA2 | Goat polyclonal | R&D Systems (Cat# AF2400, Lot# ULB0311101) | ICC, FC |
| Muc-1 | Monoclonal | R&D Systems (Cat# MAB6298, Lot# CDYA0111031) | ICC, FC |
| Nanog | Rabbit monoclonal | Abcam (Cat# ab80892, Lot# GR40243-14) | ICC |
| Nkx2.1 | Rabbit polyclonal | Abcam (Cat# ab76013, Lot# GR76790-2) | ICC, IHC, FC |

TABLE 1-continued

List of antibodies used in staining, flow cytometry and western blot for various experiments

| | | | |
|---|---|---|---|
| Oct4 | Goat polyclonal | Abcam (Cat# ab27985, Lot# GR56247-1) | ICC, FC |
| p63 | Monoclonal | Santa Cruz (Cat# sc-71825, Lot# H2510) | IHC |
| Pax9 | Rat monoclonal | Abcam (Cat# ab28538, Lot# GR53993-1) | ICC |
| Pax9 | Goat polyclonal | Santa Cruz (Cat# sc-7746, Lot# K121) | ICC |
| PCNA | Monoclonal | Abcam (Cat# ab29, Lot# GR70504-2) | IHC |
| proSPB | Rabbit polyclonal | Millipore (Cat# ab3430, Lot# NG1820771) | ICC, FC |
| proSPC | Rabbit monoclonal | Millipore (Cat# ab3786, Lot# 2117989) | ICC, IHC, FC |
| proSPC | Rabbit polyclonal | Abcam (Cat# ab40879, Lot# GR86765-1) | WB |
| Sox2 | Rabbit polyclonal | Abcam (Cat# ab97959, Lot# Unknown) | ICC |
| Sox2-AF647 | Monoclonal | BD Pharmingen (Cat# 562139, Lot# 18245) | ICC, FC |
| Sox17 | Goat polyclonal | R&D Systems (Cat# AF1924, Lot# KGA0411031) | ICC, FC |
| Sox17 | Mouse monoclonal | Abcam (Cat#ab84990) | ICC |
| SPA | Rabbit polyclonal | Millipore (Cat# ab3420, Lot# NG1888873) | ICC |
| SPA | Rabbit polyclonal | Santa Cruz (Cat# sc-13977, Lot# K0807) | WB |
| SPC | Rabbit polyclonal | Santa Cruz (Cat# sc-13979, Lot# L1710) | ICC, IHC, FC |
| SPC | Monoclonal | Life Sciences Advanced Tech.(Cat #E01S0168) | ELISA |
| SSEA4 | Monoclonal | Millipore(Cat# MAB4304, Lot # LV1488380 | ICC |
| T1α | Monoclonal | Abcam (Cat# ab10288, Lot# GR47830-3) | IHC |
| Tbx1 | Rabbit polyclonal | Abcam(Cat # ab18530) | ICC |
| TRA-1-81 | Monoclonal | Millipore(Cat#MAB4381, Lot # LV1512392) | ICC |
| CD166-PE | Mouse Monoclonal | (Cat# 559263, Lot# 3018832) | FC |
| CD104-FITC | Mouse Monoclonal | (Cat# 64233, Lot # 3039557 | FC |

| Detection Antbodies | | |
|---|---|---|
| Type | Provider(Cat #) (lot #) | Application |
| Alexa Fluor ® 555 Donkey Anti-Goat IgG (H + L) | Invitrogen (Cat# A21432, Lot# 439379) | ICC, IHC |
| Alexa Fluor ® 568 Donkey Anti-Mouse IgG | Invitrogen (Cat# A10037, Lot# 1110068) | ICC, IHC |
| Alexa Fluor ® 488 Donkey Anti-Rat IgG (H + L) | Invitrogen (Cat# A21208, Lot# 1017330) | ICC |
| Alexa Fluor ® 488 Rabbit Anti-Goat IgG (H + L) | Invitrogen (Cat# A11078, Lot# 1069847) | ICC, IHC |
| Alexa Fluor ® 555 Goat Anti-Rabbit IgG (H + L), highly cross-absorbed | Invitrogen (Cat# A21429, Lot# 1010124) | ICC, IHC |
| Alexa Fluor ® 488 Goat Anti-Rabbit IgG (H + L), highly cross-adsorbed | Invitrogen (Cat# A11034, Lot# 1008720) | ICC, IHC |
| Alexa Fluor ® 555 Goat Anti-Mouse IgG (H + L), highly cross-adsorbed | Invitrogen (Cat# A21424, Lot# 1214852) | ICC, IHC |
| Alexa Fluor ® 555 Goat Anti-Rat IgG (H + L) | Invitrogen (Cat# A21434, Lot# 1008806) | ICC |
| Alexa Fluor ® 488 Chicken Anti-Rabbit IgG (H + L) | Invitrogen (Cat# A21441, Lot# 1003212) | ICC, IHC |
| Alexa Fluor ® 488 Chicken Anti-Goat IgG (H + L) | Invitrogen (Cat# A21467, Lot# 474697) | ICC, IHC |
| Goat anti-Mouse IgG ® H&L (FITC) | Abcam (Cat# ab6785, Lot# GR6891-4) | ICC, IHC |
| Goat anti-Rabbit IgG-HRP | Santa Cruz (Cat# sc-2004, Lot# H2806) | WB |
| HRP-conjugated | Life Sciences Advanced Tech.(Cat #E01S0168 | ELISA |
| APC Mouse IgG2a,κ Isotype Control | BD Pharmingen (Cat# 555576, Lot# 33828) | Isotype control |
| PE Mouse IgG1, κ Isotype Control | eBiosciences (Cat# 12-4714-82, Lot# E01672-1630) | Isotype control |

TABLE 1-continued

List of antibodies used in staining, flow cytometry and western blot for various experiments

| | | |
|---|---|---|
| Alexa Fluor ® 647 Mouse IgG1, κ Isotype Control | BD Pharmingen (Cat# 557714, Lot# 34876) | Isotype control |
| Mouse IgG2a κ Isotype Control FTIC - | eBiosciences (Cat# 11-4724-81, Lot# E00590-1630) | Isotype control |
| Isotype FITC Goat Anti mouse Ig | (Cat# 611233, Lot# 039557) | |
| PE mouse IgG κ isotype control | (Cat# 555749, Lot# 38193) | |

Abbreviations:
IHC, immunohistochemistry;
ICC, immunocytochemistry;
FC, flow cytometry;
WB, Western Blot;
ELISA, Enzyme-linked immunosorbent assay;
PE, Phycoerythrin,
APC, Allophycocyanin;
FITC, Fluorescein isothiocyanate;
HRP, horseradish peroxidase;
CCSP, Clara cell secretory protein;
PCNA, Proliferating cell nuclear antigen;
SSEA4, Stage-Specific Embryonic Antigen-4;
Oct4, Octamer-binding transcription factor 4;
Muc-1, Mucin 1;
SPA, Surfactant protein A;
SPB, Surfactant protein B;
SPC, Surfactant protein C;
Nkx2.1, NK2 homeobox 1;
Sox2, SRY (sex determining region Y)-box 2;
Sox17, SRY-box 17;
Tbx1, T-box 1;
Pax 9, Paired box gene 9;
CXCR4, C-X-C chemokine receptor type 4;
FoxA2, forkhead box protein A2;
AF647, Alexa Fluor ® 647.

Cultivation of Human iPS Cells.

The human iPS cell lines, iPSC (IMR90, C1) and iPSC (neonatal foreskin, C2), were obtained (Takahashi K, et al. 2007. Cell 131(5):861-872). Both human iPS cell lines were generated by lentiviral transduction of isolated human skin fibroblasts (IMR90, C1 clone) and neonatal foreskin fibroblast (C2 clone) with OCT-4, SOX2, Nanog and lin28 genes. These induced pluripotent human stem cells have been extensively characterized; they have normal karyotypes and telomerase activity, express cell surface markers and genes that characterize human ES cells, and maintain the developmental potential to differentiate into advanced derivatives of all three primary germ layers (Takahashi K, et al. 2007. Cell 131(5):861-872). Both lines were cultured and maintained as described previously (Takahashi K, et al. 2007. Cell 131(5):861-872). Briefly, iPS cells were propagated on irradiated mouse embryonic fibroblast (MEF) feeder layers in DMEM-F12 media supplemented with 20% knock out serum replacement, 4 ng/ml bFGF, 1 mM glutamine, 1% mM non-essential amino acids and 0.1 mM β-mercaptoethanol at 37° C., 5% CO2 and 90-95% humidity, with medium changes every day. Undifferentiated iPS cells were passaged every 4-5 days onto fresh feeders by mechanical dissociation using a Stem Cell Cutting Tool (VWR).

In Vitro Differentiation of iPS Cells to AETII Cells

Human iPSCs were differentiated to alveolar epithelium in a directed differentiation protocol via definitive endoderm (DE) and anterior foregut endoderm (AFE). iPS cells were differentiated towards definitive endoderm under conditions described previously (Duan Y, et al. 2010. Stem Cells 28(4):674-686, Kubo A, et al. 2004. Development. 131(7): 1651-1662). Briefly, h-iPSC were cultured in RPMI 1640 medium supplemented with 100 ng/ml activin A, 2 mM L-glutamine and 1% antibiotic-antimycotic for 48 hours; 1xB27 supplement, 0.5 mM sodium butyrate and 0.1% FBS were added into the same medium and the cells were cultured for another 4 days, with daily medium changes (D'Amour K A, et al. 2005. Nat Biotechnol 23(12):1534-1541).

DE generated by exposure to activin A were trypsinized, reseeded at a ratio of 1:1-2 on human ECM protein-coated plates and differentiated to anterior foregut endoderm with IMDM+5% FBS, 2 mM L-glutamine, 1 mM nonessential amino acids, 1% antibiotic-antimycotic supplemented with 200 ng/ml NOGGIN and 10 mM SB-431542 for 2 days (Longmire T A, et al. 2012. Cell Stem Cell 10(4):398-411, Green M D, et al. 2011. Nat Biotechnol 29(3):267-272).

AFE cells were maintained in IMDM differentiation medium with 10% FBS, 2 mM L-glutamine, 1 mM nonessential amino acids, 1% antibiotic-antimycotic, retinoic acid (0.5 µM), FGF-10 (10 ng/ml), EGF (10 ng/ml), Wnt3a (100 ng/ml), and KGF (10 ng/ml each) for 10-14 days. Cells were maintained in SAGM culture medium (Lonza), plus 1% fetal bovine serum (FBS) until seeding into lung matrices (Longmire T A, et al. 2012. Cell Stem Cell 10(4):398-411, Green M D, et al. 2011. Nat Biotechnol 29(3):267-272).

Differentiated cells at day 22 were then maintained in DMEM medium with 10% FBS, 2 mM L-glutamine, 1 mM nonessential amino acids, 1% antibiotic-antimycotic and 100 mM IWR-1 for 7 days.

Isolation of Human Type II Cells

Alveolar type II (AETII) cells were isolated from human lungs rejected for transplant as previously described (Bove P F et al. 2010. J Biol Chem 285(45):34939-34949). Briefly, the right middle lobe was cannulated through the main stem bronchus and removed from the rest of the lung. The distal airspaces were lavaged 6-10 times using a $Ca^{2+}$- and $Mg^{2+}$-free solution (0.5 mm EGTA, 140 mm NaCl, 5 mm KCl, 2.5 mm Na$_2$HPO$_4$, 10 mm HEPES, and 6 mm glucose) and lavaged 3 times with a modified version of this solution (no glucose, 2.0 mm CaCl$_2$ and 1.3 mm MgSO$_4$). Elastase (13 units/ml), was instilled into the distal airspaces and incubated at 37° C. for 30 min. Isolated cells were resuspended in DMEM and decanted onto PBS- and DMEM-rinsed Petri dishes coated with human IgG antibody. After 60 min at 37° C., non-adherent AETII cells were incubated with a monoclonal antibody against fibroblasts (AS02) and pan-mouse IgG Dynabeads for removal by magnet. AETII cells were resuspended in DMEM containing 10% FBS, amphotericin B, ceftazidime, tobramycin, and vancomycin.

Flow Cytometry and Immunochemistry

DE, AFE and iPSC-AETII cell populations were assessed by immunofluorescence or/and flow cytometry before differentiation, during the induction of DE and AFE and iPSC-AETII, and after cultivation in the decellularized lung matrix.

For immunostaining, cells were washed with PBS, fixed in 4% paraformaldehyde for 20 min at room temperature (RT) and permeabilized with 0.1% Triton X-100 in PBS for 15 min at RT. Cells were blocked in 3% BSA in PBS for 60 min at RT and incubated with primary antibody overnight at 4° C. The next day, cells were washed with PBS and incubated with secondary antibody for 2 h at RT. After washing, the cells were incubated with 4, 6-diamidino-2-phenylindole (DAPI) (1:1000) nuclear stain.

Paraffin sections of cell-seeded lung scaffolds were stained with H&E. Additional sections were permeabilized with 0.2% Triton X for 15 min after heat-mediated citric acid antigen retrieval and blocked with 5% BSA for 1 hr. at RT.

Primary antibodies were applied overnight at 4° C. Sections were incubated with secondary antibodies for 1 hr at RT, rinsed, treated with DAPI for 1 minute, and mounted with PVA-DABCO cover slipping solution. Stained cells and slides were imaged with a Zeiss Axiovert 200M inverted microscope and a Hamamatsu camera.

For flow cytometry, cells were dissociated into single-cell suspensions by incubation with 0.25% trypsin for 2 min, and fixed (Fixation/Permeabilization kit, BD Biosciences). After blocking for 30 min on ice, the cells were incubated with primary antibody in blocking solution for 30 min on ice. The cells were resuspended in 350 µl of Perm/Wash buffer after incubation with conjugated secondaries for 30 min on ice, washed twice, and analyzed by flow cytometry. See Table 1 for antibody information.

Real Time Quantitative RT-PCR

Total RNA was extracted using the RNeasy Mini Kit from Qiagen, following the manufacturer's instructions. First-strand complementary DNA (cDNA) was synthesized with random hexamers as primers, using SuperScript First-Strand Synthesis System according to manufacturer's protocol (Invitrogen). Each sample was run in triplicate with iQ™ SYBR Green Supermix (Bio-Rad). PCR conditions included an initial denaturation step of 4 min at 95° C., followed by 40 cycles of PCR consisting of 15s at 95° C., 30 s at 60° C., and 30 s at 72° C. Average threshold cycle (Ct) values from the triplicate PCR reactions for a gene of interest (GOI) were normalized against average GAPDH Ct values from the same cDNA sample. Fold change of GOI transcript levels between sample A and sample B equals $2^{-\Delta\Delta Ct}$, where $\Delta Ct = Ct_{(GOI)} - Ct_{(GAPDH)}$, and $\Delta\Delta Ct = \Delta Ct_{(A)} - \Delta Ct_{(B)}$. See Table 2 for primers.

TABLE 2

Sequences of primers used in qRT-PCR for various experiments

| Gene | Length (bp) | Primer Sequences |
|---|---|---|
| hSPA | 180 | Forward: TCCAAGCCACACTCCACGA; (Seq id no: 1)<br>Reverse: TTCCTCTGGATTCCTTGGG; (Seq id no: 2) |
| hSPB | 69 | Forward: TGGGAGCCGATGACCTATG; (Seq id no: 3)<br>Reverse: GCCTCCTTGGCCATCTTGT; (Seq id no: 4) |
| hNKX2.1 | 93 | Forward: GGACGTGAGCAAGAACATG; (Seq id no: 5)<br>Reverse: TCGCTCCAGCTCGTACACC; (Seq id no: 6) |
| hSPC | 94 | Forward: CCTTCTTATCGTGGTGGTGGT; (Seq id no: 7)<br>Reverse: TCTCCGTGTGTTTCTGGCTCAT; (Seq id no: 8) |
| hMucin-1 | 88 | Forward: AGCTTCTACTCTGGTGCACAA; (Seq id no: 9)<br>Reverse: GGTGGCTGGGAATTGAGA; (Seq id no: 10) |
| hOCT4 endogenous | 164 | Forward: CCTCACTTCACTGCACTGTA; (Seq id no: 11)<br>Reverse: CAGGTTTTCTTTCCCTAGCT; (Seq id no: 12) |
| hSOX2 endogenous | 151 | Forward: CCCAGCAGACTTCACATGT; (Seq id no: 13)<br>Reverse: CCTCCCATTTCCCTCGTTTT; (Seq id no: 14) |
| hNANOG endogenous | 239 | Forward: CCAAATTCTCCTGCCAGTGAC; (Seq id no: 15)<br>Reverse: CACGTGGTTTCCAAACAAGAAA; (Seq id no: 16) |
| hCC10 | 105 | Forward: CCCTGGTCACACTGGCTCTC; (Seq id no: 17)<br>Reverse: TCATAACTGGAGGGTGTGTC; (Seq id no: 18) |
| hCXCR4 | 79 | Forward: CACCGCATCTGGAGAACCA; (Seq id no: 19)<br>Reverse: GCCCATTTCCTCGGTGTAGTT; (Seq id no: 20) |
| hFOXA2 | 89 | Forward: GGGAGCGGTGAAGATGGA; (Seq id no: 21)<br>Reverse: TCATGTTGCTCACGGAGGAGTA; (Seq id no: 22) |

TABLE 2-continued

Sequences of primers used in qRT- PCR for various experiments

| Gene | Length (bp) | Primer Sequences |
|---|---|---|
| hSOX17 | 61 | Forward: GGCGCAGCAGAATCCAGA; (Seq id no: 23)<br>Reverse: CCACGACTTGCCCAGCAT; (Seq id no: 24) |
| hPAX9 | 132 | Forward: GTTATGTTGCTGGACATGGGT; (Seq id no: 25)<br>Reverse: GAAGCCGTGACAGAATGACTAC; (Seq id no: 26) |
| hTBX1 | 117 | Forward: GCTCCTACGACTATTGCCC; (Seq id no: 27)<br>Reverse: CGTATTCCTTGCTTGCCCT; (Seq id no: 28) |
| hCD31 | 140 | Forward: ATTGCAGTGGTTATCATCGGAGTG; (Seq id no: 29)<br>Reverse: CTCGTTGTTGGAGTTCAGAAGTGG; (Seq id no: 30) |
| hTSHR | 156 | Forward: TTTCTTACCCAAGCCACTGC; (Seq id no: 31)<br>Reverse: TTCTCTTCATATTCCTGGTGG; (Seq id no: 32) |
| hALB | 149 | Forward: AAACGCCAGTAAGTGACAGAG; (Seq id no: 33)<br>Reverse: ATATCTGCATGGAAGGTGAAT; (Seq id no: 34) |
| hGAPDH | 122 | Forward: GACAACAGCCTCAAGATCATCAG; (Seq id no: 35)<br>Reverse: ATGGCATGGACTGTGGTCATGAG; (Seq id no: 36) |

Transmission Electron Micrograph

Cell samples were prepared following a modified protocol from Schmiedl et al (Schmiedl, et al. *Histochem Cell Biol* 1-12). Briefly, native human AETII and iPSC-AETII cells were fixed at 37° C. with a 2.5% glutaraldehyde/2.0% paraformaldehyde mixture in 0.2M sodium cacodylate for 30 minutes, followed by 2 hour incubation at 4° C. The samples were dehydrated following a standard ethanol series. The samples were post-processed by $OsO_4$ fixation and en block uranyl acetate staining. Sections (70 to 80-nm) were taken and incubated in uranyle acetate and lead citrate for increased contrast. Images were taken using a Philips Tecnai transmission electron microscope.

Preparation of Decellularized Extracellular Matrix Scaffolds

Three-month-old Fischer or Sprague Dawley rats were anesthetized with sodium pentobarbital, according to the guidelines set forth by the American Veterinary Medical Association (60 mg/kg IP). Lung extracellular matrix scaffolds were prepared as previously described (Petersen T H, et al. 2010. *Science* 329(5991):538-541, Calle E A, et al. 2011. *J Vis Exp* (49). pii: 2651). Lungs were perfused with heparin (50 U/ml, Sigma) in PBS, and removed with the heart and trachea. The pulmonary artery and trachea were cannulated and the lungs were perfused through the pulmonary artery with sodium nitroprusside (1 ml/ml, Fluka) before being treated with decellularization solution (8 mM CHAPS, 1M NaCl, 5 mM EDTA in PBS) for 2-3 hours at 37° C. Scaffolds were treated with benzonase endonuclease (90U/ml, Sigma) for 1 hr. at 37° C., followed by extensive rinsing with PBS, antibiotics and antimycotics.

Human lungs were obtained from beating-heart donors or warm autopsy as arranged through Gift of Life Michigan, and were decellularized as recently described (Booth A J. 2012. *Am J Resp Crit Care Med.* 186(9): 866-76). Lung samples were agitated in sterile deionized, distilled water and incubated in 0.1% Triton X-100 for cell lysis. Samples were washed with sterile PBS, incubated with 2% sodium deoxycholate and washed again. Lungs were incubated in 1M NaCl to lyse residual nuclei. After decanting NaCl, tissues were rinsed and incubated with 30 µg/mL DNAse in 1.3 mM $MgSO_4$ and 2 mM $CaCl_2$. The DNAse solution was decanted and tissues were washed with sterile PBS. (Booth A J, et al. 2012. *Am J Resp Crit Care Med.* 186(9): 866-76).

Culture of Cells on Rat Lung Extracellular Matrix Scaffolds

Rat scaffolds were mounted in the bioreactor as described previously (Petersen T H, et al. 2010. *Science* 329(5991): 538-541). Cannulas were connected to tubing loops to provide perfusion and introduction of cells to the scaffold. Forty million iPSC-AETII cells were suspended in 3-5 ml of culture medium (SAGM-1% FBS) and introduced into the airway compartment; perfusion was initiated at 1 ml/min immediately after cell seeding. In additional experiments, $6 \times 10^6$ native human AETII cells—isolated from human lung—were introduced into the upper right lobe of a decellularized rat lung. The full volume of culture media was changed once at day 3 or 4 and samples were harvested at days 1, 3 and 7 and saved for histology. In parallel experiments, iPSC-AETII cells were seeded onto sections of decellularized rat lung at a concentration of $1.5 \times 10^5$ cells/slice in SAGM-1% FBS media for 7 days. Finally, $3 \times 10^5$ of either AETII cells or native human AETII cells were transferred onto decellularized human lungs slices in SAGM-1% FBS and cultured for 1 week; media was changed every other day.

Enzyme-Linked Immunosorbent Assay Analysis (ELISA) for SPC

ELISA was performed on cell culture media collected during iPSC-AETII differentiation to quantify secreted SPC (Life Science Advanced Technology) according to the manufacturer's instructions. SPC values were normalized to the total number of cells.

Western Blotting

Cells were incubated in RIPA buffer supplemented with protease inhibitors (Complete Mini, Roche,) on ice for 30 min. Protein concentration was determined from cell lysates using a bicinchoninic acid protein assay (Thermo Fisher Scientific). Cell lysates were denatured and equal amounts of protein per sample were subjected to SDS-PAGE and immunoblotting as described previously. HRP-conjugated goat anti-mouse and goat anti-rabbit secondaries were detected by enhanced chemiluminescence.

Proliferation Assay

To assess cell proliferation within the lung scaffold, lungs seeded and cultured with AETII for 3 days and 7 days were fixed in 4% PBS-buffered paraformaldehyde (pH 7.4) and post-fixed with 70% EtOH. The immunocytochemical staining against human caspase and PCNA was performed as described in elsewhere herein. The images were visualized with a Zeiss Axiovert 200M inverted microscope and imaged with Hamamatsu camera. The percentage of positive nuclear staining was calculated based on total cell numbers in three high power fields.

Statistical Analyses

Statistics were done with Origin (OriginLab, Northampton, Mass.). The data were expressed as mean±SEM. (standard error of measurement, all error bars represent ±SEM). Unpaired, two-tailed Student's t-tests were performed to evaluate whether the two groups were significantly different from each other. p values less than 0.05 (two-tailed) were considered statistically significant. All error bars represent ±SEM The results of the experiments are now described.

The experiments presented herein demonstrate an efficient and consistent, step-wise differentiation method to generate definitive endoderm (DE), anterior foregut endoderm (AFE), and subsequently, a relatively homogeneous population of human AETII and AETI cells from human iPSCs (iPSCs) (FIG. 1A). These cells not only demonstrate the phenotype of mature human alveolar type I and type II cells, but also express a high percentage of type I and II cell markers when compared to freshly isolated human primary alveolar type I and type II cells. Additionally, these iPSC-derived AETII cells are capable of repopulating an acellular lung matrix, and give rise to cell types that reside in the distal lung (FIG. 1B).

Efficient Derivation of Definitive Endoderm Cells

Figure 7M:
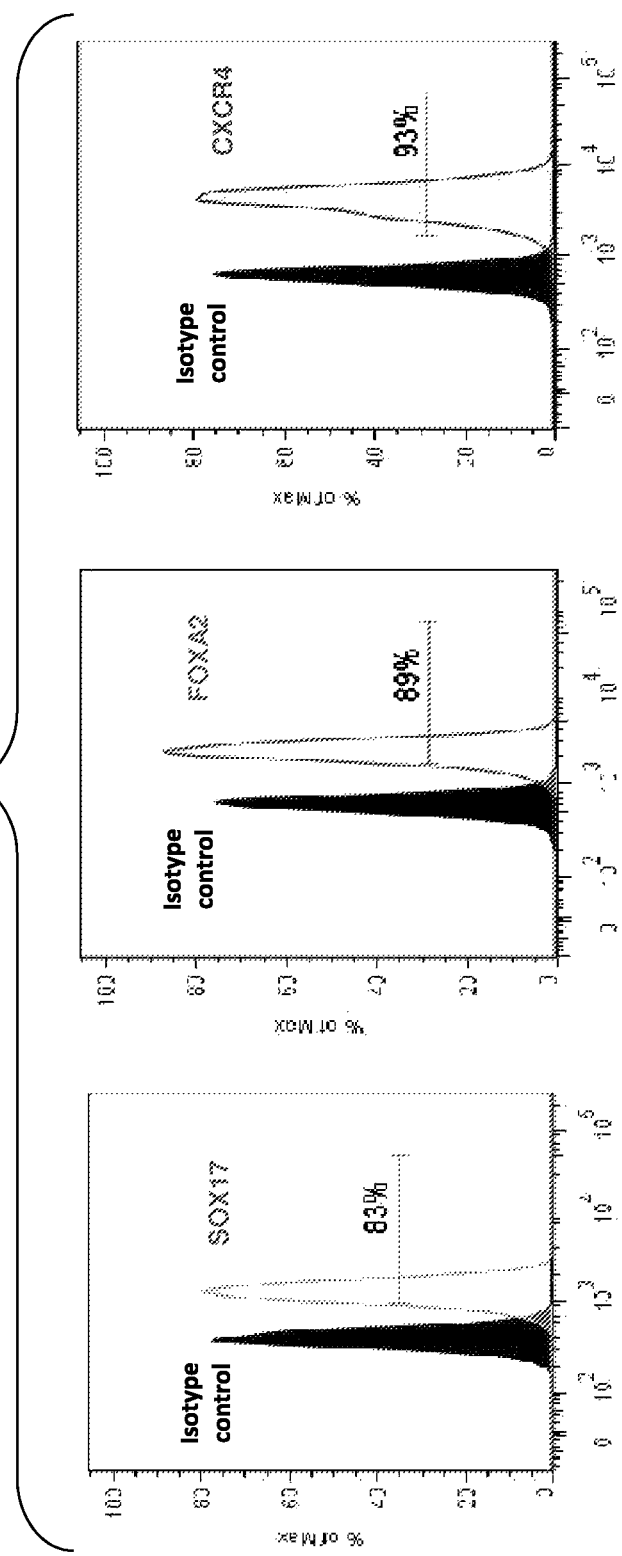
Figure 8M:
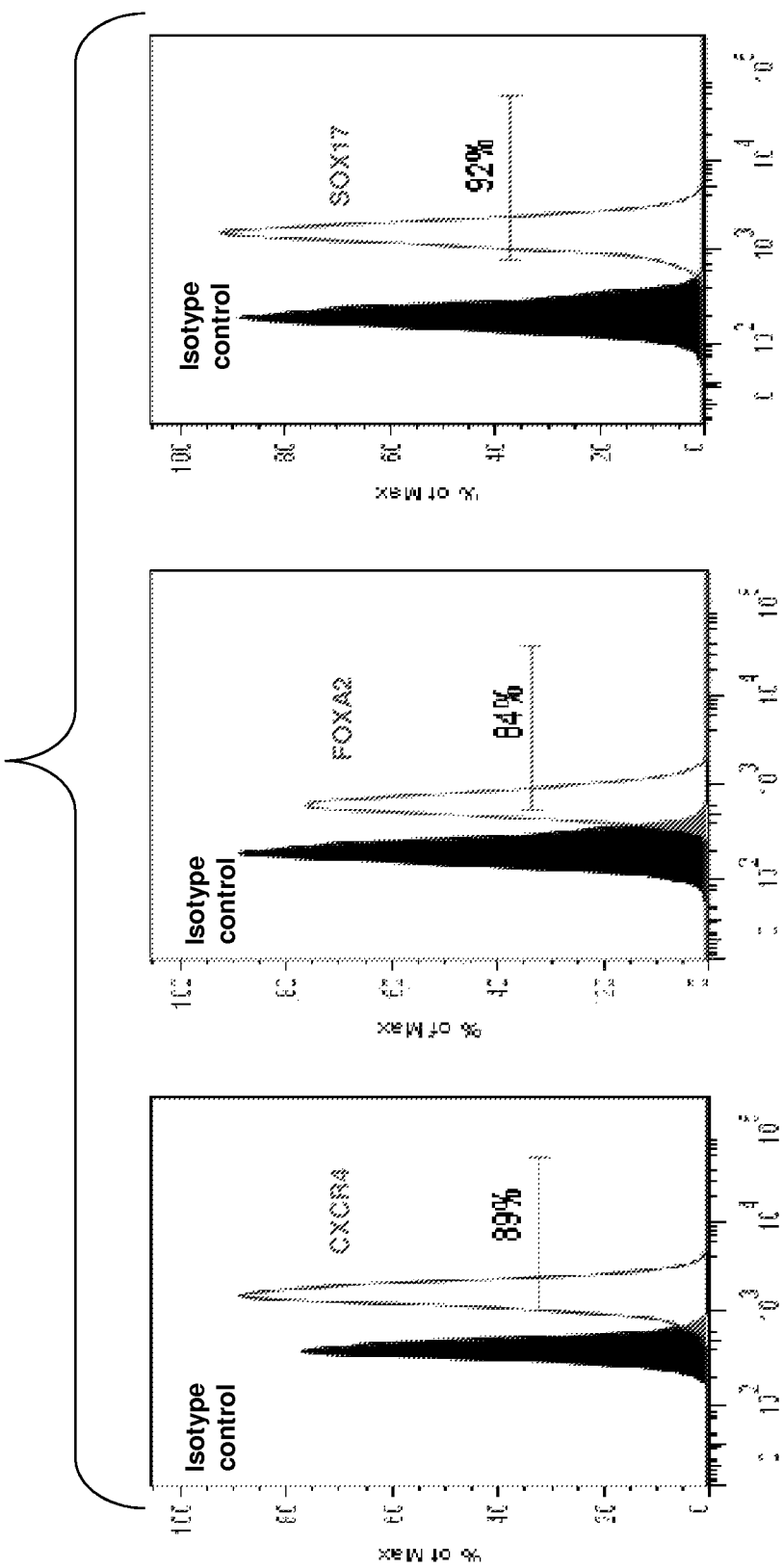

Embryonic lung arises from definitive endoderm (DE) (Green M D, et al. 2011. *Nat Biotechnol* 29(3):267-272, Banerjee E R, et al. 2012. *PLoS One* 7(3):e33165, Kadzik R S, et al. 2012. *Cell Stem Cell* 10(4):355-361). Therefore, in the first step, iPSC were differentiated to DE by exposing them to saturating concentrations of activin A during the first 6 days of differentiation. iPSC were initially cultured without serum for 48 hours with 100 ng/ml activin A, and then changed to a low serum concentration provided with 1xB27 culture medium. During the time that iPSC were exposed to activin A, the majority of the cells in the colonies converted to DE cells, while those cells that did not gradually died as monitored through visual observation. After 6 days of differentiation, both iPSC clones (denoted as C1 and C2) stained positively for SOX17 and FOXA2, and the majority of the cells were positive for both SOX17 and FOXA2 (FIG. 1D, FIG. 7A-7J for C1 cells, FIG. 8A-8J for C2 cells). When endoderm marker expression was monitored using qRT-PCR for SOX17, CXCR4 and FOXA2, no expression of these markers was observed at day 0; expression then increased from day 0 to day 6 in iPS cells exposed to activin A (FIG. 7L and FIG. 12A for C1 cells, FIG. 8L and FIG. 12B for C2). Flow cytometric analysis demonstrated that the cell population derived from iPS cells at day 6 expressed a high percentage of markers associated with definitive endoderm, including 92.71±4.0% for CXCR4, 83.7 6±2.0% for SOX17, and 87.66±1.2% FOXA2 in C1 and 87.23±2.0% for CXCR4, 91.42±3.0% for SOX17, and 83.54±1.8% FOXA2 in C2 (FIG. 7M for C1 cells, FIG. 8M for C2). It was found that the protocol used herein was highly efficient for generating a relatively homogeneous population of DE from iPSC; based on the dual expression of SOX17 and FOXA2 in iPSC clones. It was observed that more than 85% of C1 and 89% of C2 was comprised of endodermal cells (FIG. 7K for C1 cells, FIG. 8K for C2). Both the C1 clone (which is of fetal lung origin) and the C2 clone (which is derived from neonatal fibroblasts) yield similar results. This suggests that this protocol may be generalized to other iPSC lines from other cell origins or that are reprogrammed using other techniques.

Generating Anterior Foregut Endoderm from Definitive Endoderm Cells

Figure 2J:
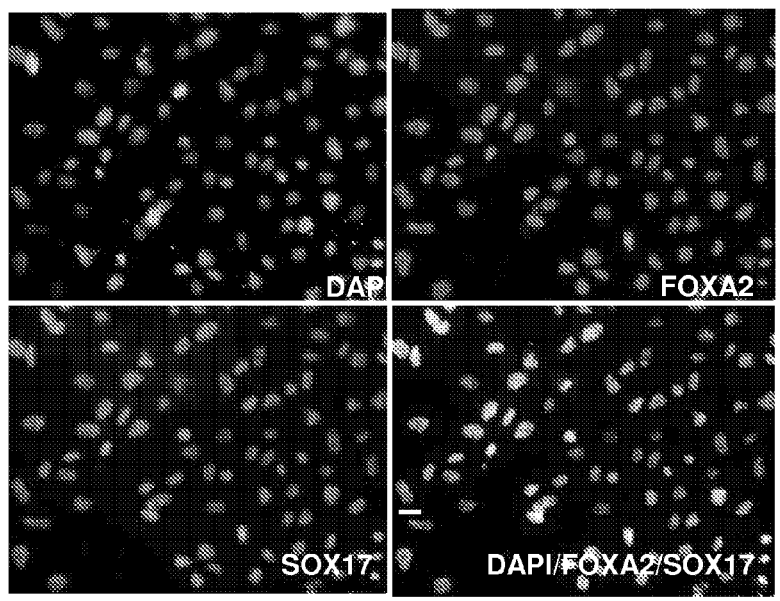
(FIG. 2J) Immunofluorescence staining showing AFE cells are positive for both SOX2 and FOXA2.
Figure 2K:
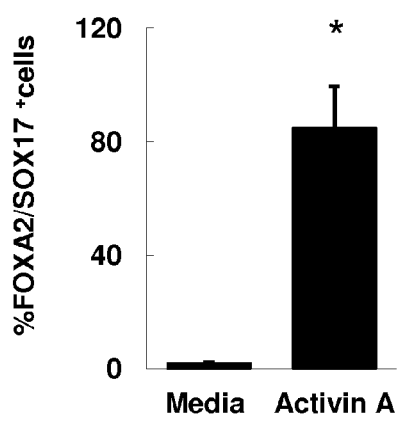
(FIG. 2K) Flow cytometric analysis of double positive cells for SOX2 and FOXA2 in AFE cells at day 8 compared to cells cultured in activin A and RPMI medium only (Y axis: % positive cells for FOXA2/SOX2).
Figure 2L:
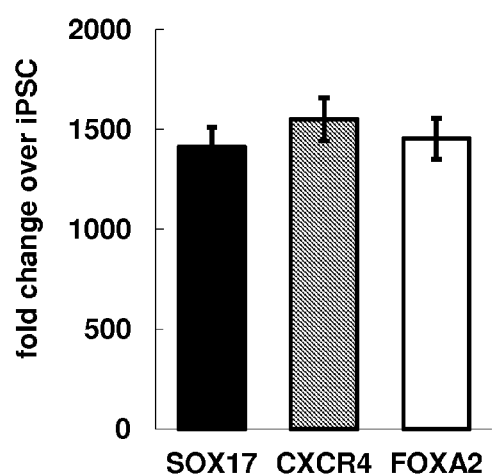
(FIG. 2L) mRNA expression of SOX2, TBX1 and PAX9 in AFE generated from DE cells in vitro at day 8 (data expressed as quantification of mRNA normalized to GAPDH and average fold change in gene expression over iPS cells. Y axis: fold changes in gene expression compared with iPSC) (FIG. 2M) Expression of NKX2.1 on day 13 after induction anterior foregut endoderm quantified by DAPI staining for nuclei, NKX2.1 positive cells, and merge.
Figure 9J:
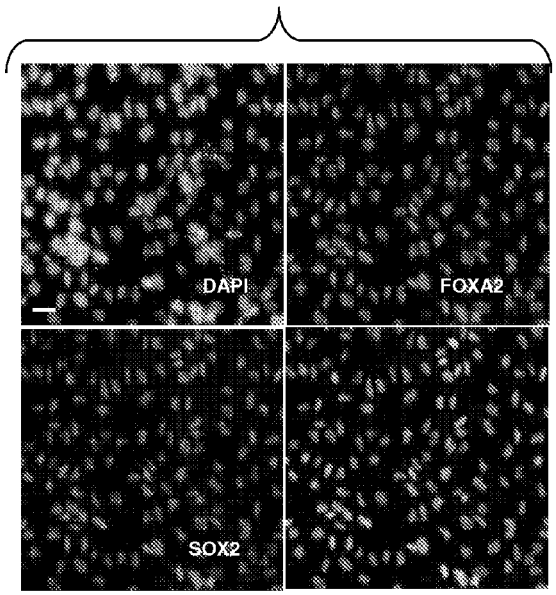
Figure 9K:
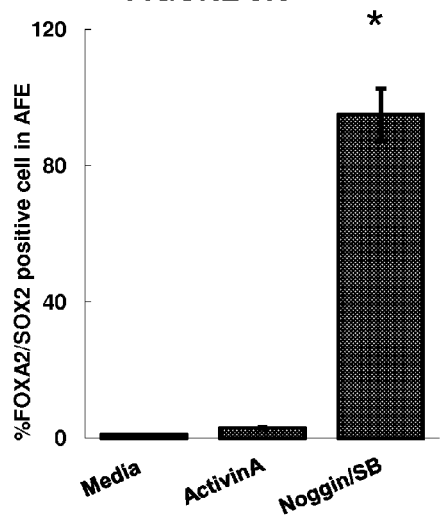
Figure 9L:
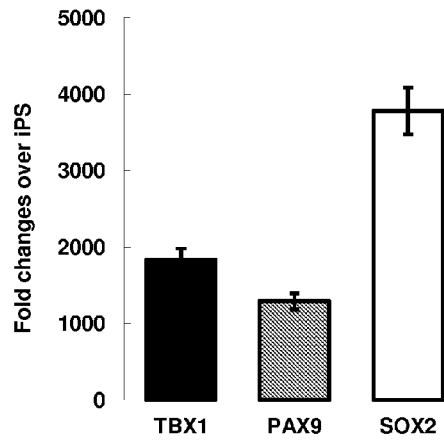
(FIG. 9L) Expression of TBX1, SOX2, and PAX9 mRNA quantified by qRT-PCR in C2 iPS cells at day 8 (Data expressed as quantification of mRNA normalized to GAPDH and average fold change in gene expression over iPSCs cells).
Figure 12A:
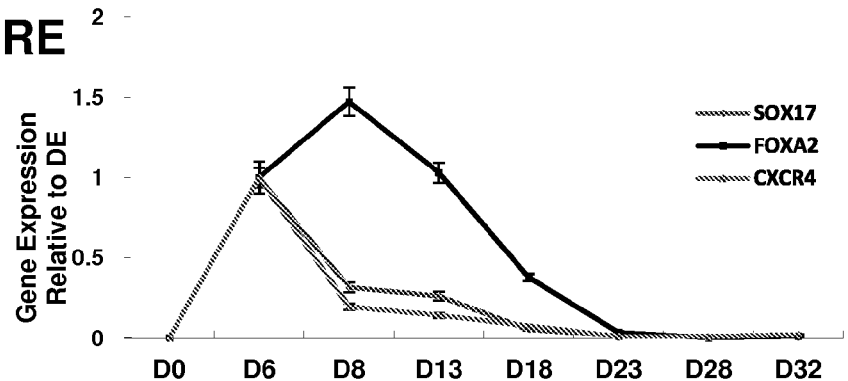
FIG. 12A through FIG. 12D, is a series of graphs depicting the results of experiments.
Figure 12B:
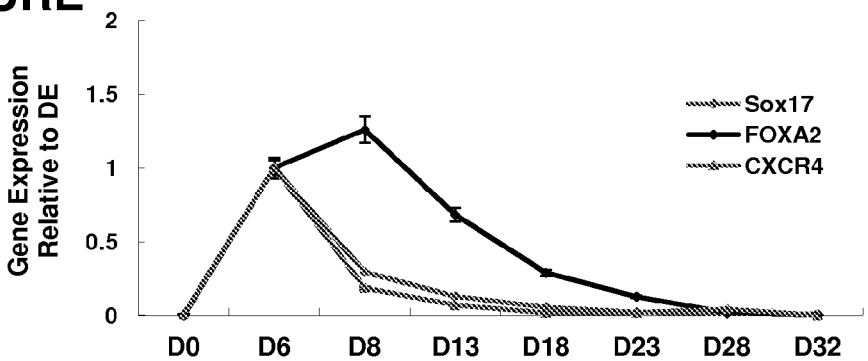

Following developmental paradigms, directed differentiation of iPS cells to alveolar epithelium should proceed by generation of definitive endoderm, followed by patterning into anterior foregut endoderm (AFE). Differentiation of AFE cells from DE was induced by exposing cells to NOGGIN (200 ng/ml) and SB-431524 (10 mM) for 2 days, per the conditions described previously by Green and colleagues (Longmire T A, et al. 2012. *Cell Stem Cell* 10(4):398-411, Green M D, et al. 2011. *Nat Biotechnol* 29(3):267-272, Mou H, et al. 2012. *Cell Stem Cell* 10(4):385-397). Application of NOGGIN/SB-431542 to definitive endoderm yielded a highly enriched population of cells with strong expression of markers associated with the AFE phenotype, including SOX2, PAX9 and TBX1 in both clones. The majority of cells co-expressed SOX2 and FOXA2, as demonstrated by immunostaining at day 8 (FIG. 2A-FIG. 2J for C1 cells, FIG. 9A-FIG. 9J for C2). Cells that were negative for definitive endoderm markers gradually died off after switching to AFE differentiation media as we visualized by microscopy. In addition, the present results show that inhibition of TGF-β signaling and activin A/nodal signaling with NOGGIN/SB-431542 was sufficient in the two iPSC clones tested to increase the anterior endoderm cell population (as defined by FOXA2$^+$/SOX2$^+$) up to 92-95% as compared to <0.1% without NOGGIN/SB-431542. (FIG. 2K, for C1 cells, FIG. 9K for C2). Quantitative RT-PCR revealed a relatively modest increase in both PAX9 and TBX1 when compared to SOX2 expression, which was highly expressed in AFE cells derived from both iPSCs colonies at day 8 (FIG. 2L, for C1 cells, FIG. 9L for C2). After activin A removal at day 6 and switching to NOGGIN/SB-431542, it was observed that both CXCR4 and SOX17 decreased from day 6 to day 12. In the case of FOXA2, an increase in expression at day 8 was observed, followed by a decrease with time in culture (FIG. 12A for C1 cells, FIG. 12B for C2). These results are expected, given that endoderm is a transient stage in lung development and is expected to peak and then fade as stem cells differentiate toward later phenotypes (Yasunaga M, et al. 2005. *Nat Biotechnol* 23(12):1542-1550).

Figure 2M:
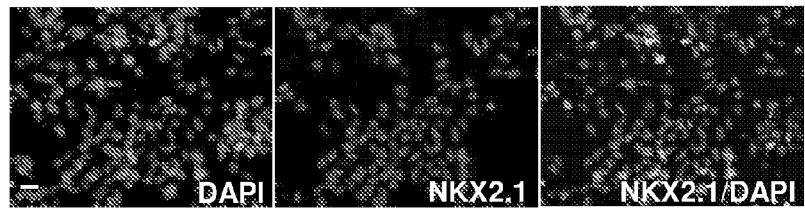
Figure 2N:
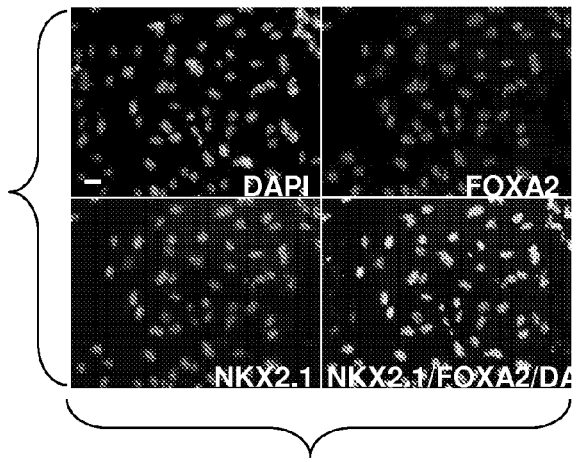
(FIG. 2N) Immunofluorescence staining showing NKX2.1 cells in AFE stained positive for FOXA2 indicating these cells are more lung progenitor rather than thyroid progenitor.
Figure 2O:
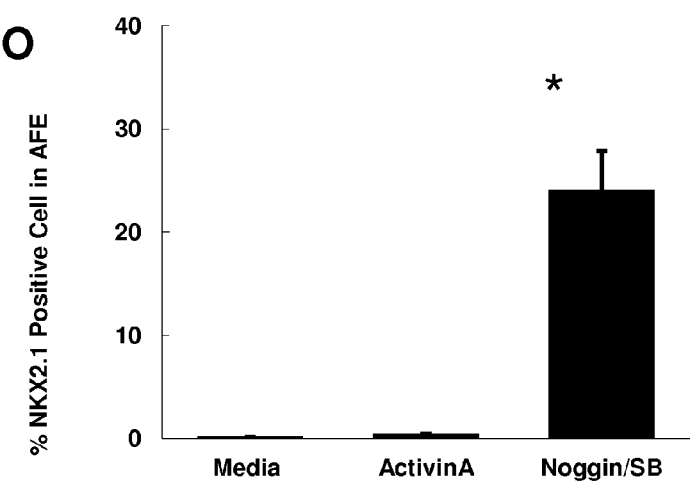
Figure 9M:
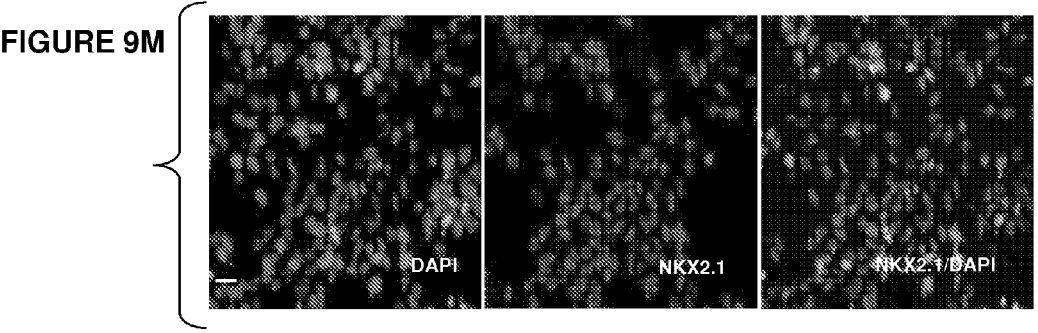
(FIG. 9M) Immunofluorescence staining of NKX2.1 in AFE derived from clone C2 at day 13 (Scale bar, 31 µm).
Figure 9N:
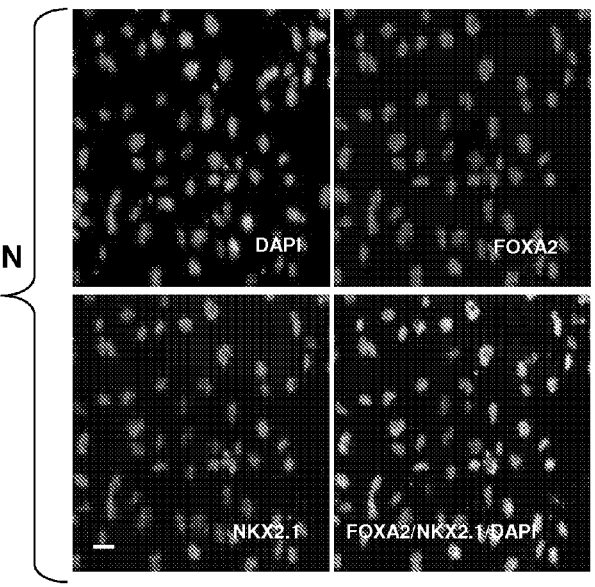
(FIG. 9N) Immunofluorescence staining showing AFE cells are positive for both NKX2.1 and FOXA2 at day 13; Most NKX2.1 positive cells were stained positive for FOXA2 (Scale bar, 31 µm).
Figure 9O:
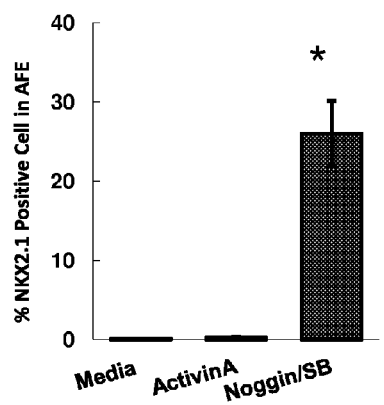

Prior to lung differentiation, all cells that will belong to the pulmonary lineage must first progress through a primordial progenitor stage defined by the upregulation of the ventral marker, NKX2.1 (Longmire T A, et al. 2012. *Cell Stem Cell* 10(4):398-411, Van Haute L, et al. 2009. *Respir Res* 10:105). NKX2.1 (homeodomain-containing transcription factor) is the earliest known marker associated with commitment to thyroid and lung, but several studies suggest that NKX2.1 induction is indicative of commitment to a lung, rather than a thyroid fate (Longmire T A, et al. 2012. *Cell Stem Cell* 10(4):398-411, Green M D, et al. 2011. *Nat Biotechnol* 29(3):267-272, Van Haute L, et al. 2009. *Respir Res* 10:105). Replacing activin A with NOGGIN/SB-431542 from day 6 to day 8, followed by the addition of a cocktail containing BMP4/Wnt3a/bFGF/KGF induced NKX2.1 expression in the AFE cell population at day 13. Most of NKX2.1 positive cells in both iPSC clones co-stained with the endoderm marker FOXA2 (FIG. 2M and FIG. 2N for C1 cells, FIG. 9M and FIG. 9N, for C2). Additionally, flow cytometric analysis showed that 24±2% of the AFE cell population derived from C1 and 26±3% from C2 was positive for NKX2.1, as compared to <1% in activin A induced cells and in cells cultured in media without NOG-GIN/SB-431542 at day 13. Continuous activin A treatment from day 6 to day 8 without the addition of NOGGIN/SB-431542 resulted in rare FOXA2$^+$/SOX2$^+$ cells and few NKX2.1$^+$ cells (FIG. 2O, for C1 cells, FIG. 9O for C2). Collectively, these expression data show that in activin A-induced definitive endoderm, exposure to NOGGIN/SB-431542 results in a highly enriched population of cells with an AFE phenotype.

Extracellular Matrix Protein Effects on Differentiation

Figure 10A:
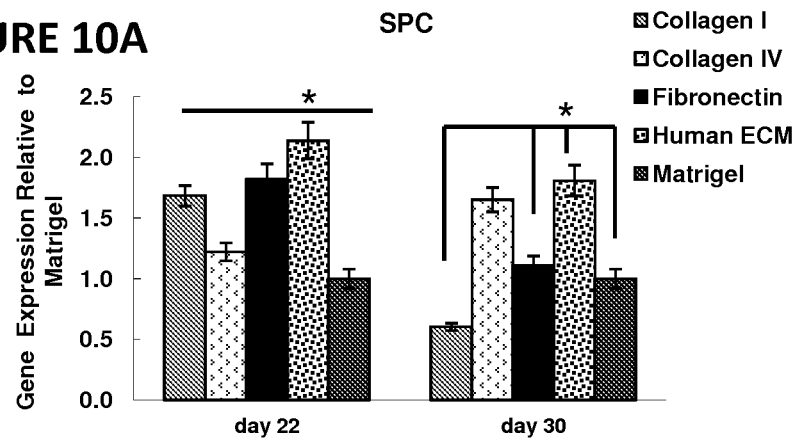
FIG. 10A through FIG. 10C, is a series of graphs demonstrating the differentiation of DE cells (day 6) to AETII (day 22) on different extracellular matrix proteins.
Figure 10B:
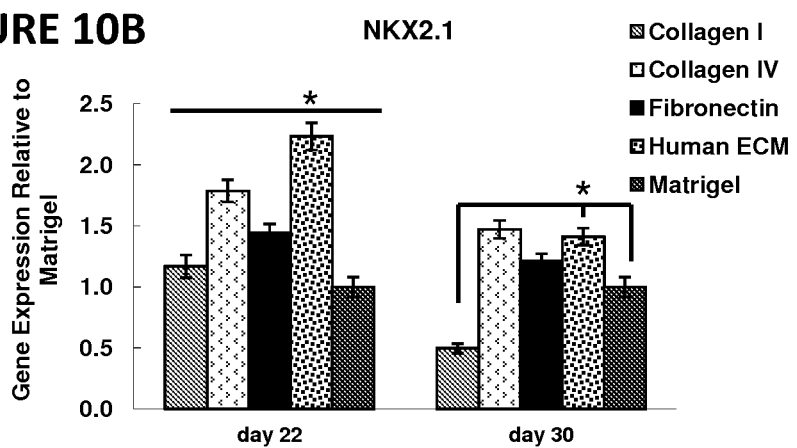
Figure 10C:
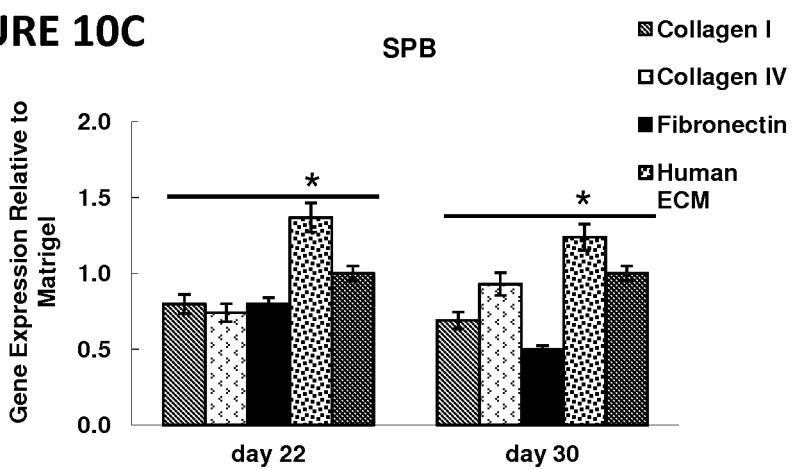

In traditional stem cell cultivation/differentiation experiments, growth factors (GFs) are added in soluble form in order to provide signals for tissue-specific differentiation (Green M D, et al. 2011. Nat Biotechnol 29(3):267-272, Mou H, et al. 2012. Cell Stem Cell 10(4):385-397, Ali N N, et al. 2002. Tissue Eng 8(4):541-550, Rippon H J, et al. 2006. Stem Cells 24(5):1389-1398, Banerjee E R, et al. 2012. PLoS One 7(3):e33165). However, differentiation has recently become increasingly linked to mechanobiological concepts such as interaction between cells and the extracellular matrix (ECM) (Reilly G C, et al. 2010. J Biomech 43(1):55-62, Lin Y M, et al. 2010. Tissue Eng Part A 16(5):1515-1526, Gutierrez J A, et al. 1998. Am J Physiol 274(2 Pt 1):L196-202). Moreover, during development, ECM protein expression represents some of the most important inducers of organ fate. Accordingly, before switching media to NOGGIN/SB-431542 to generate AFE from human pluripotent cells, the DE cells were split with trypsin and reseeded at a ratio of 1:1-2 on ECM-coated plates in media containing NOGGIN/SB-431542 for 48 hours. Adhesion of DE cells to fibronectin, collagen I, collagen IV, Matrigel, and a mixture of human ECM proteins (comprising of collagens, laminin, fibronectin, tenascin, elastin, and a number of proteoglycans and glycosaminoglycans; Sigma) was examined. Fibronectin, collagen I, collagen IV and laminin are principal components of lung matrix, and DE cells attach well to all of these proteins. However, mixed human ECM protein resulted in faster DE cell attachment and significantly higher expression of SPC, SPB, and NKX2.1 genes on both day 15 and 30 (FIG. 10A-FIG. 10C).

Efficient Derivation of Purified Lung Alveolar Type II from AFE

Figure 3G:
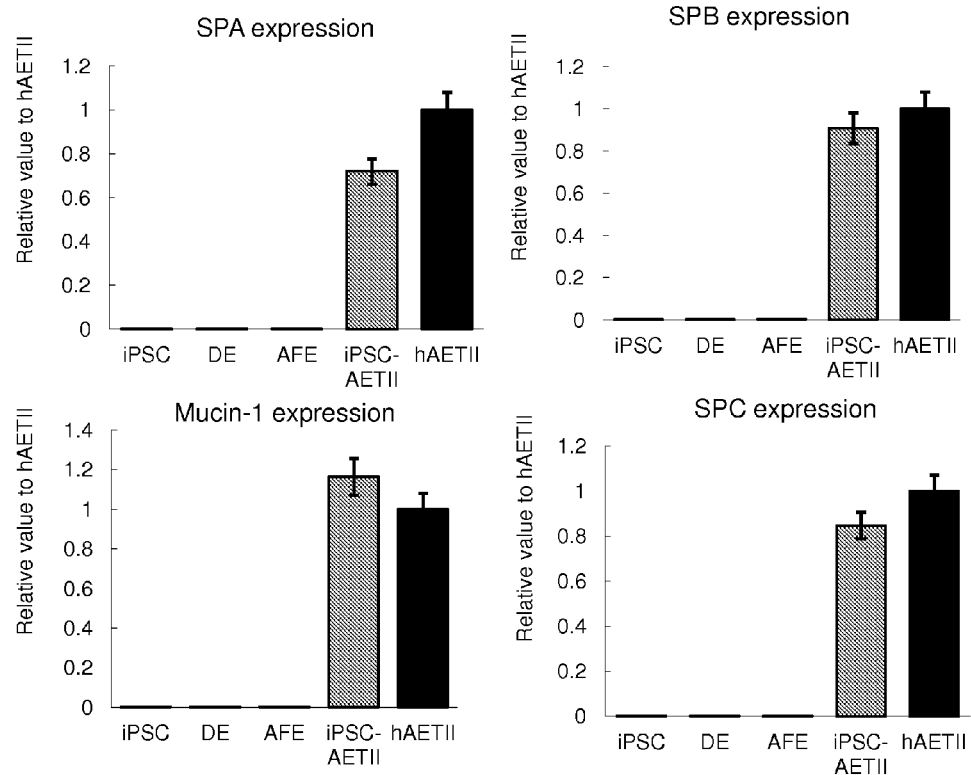
Figure 11G:
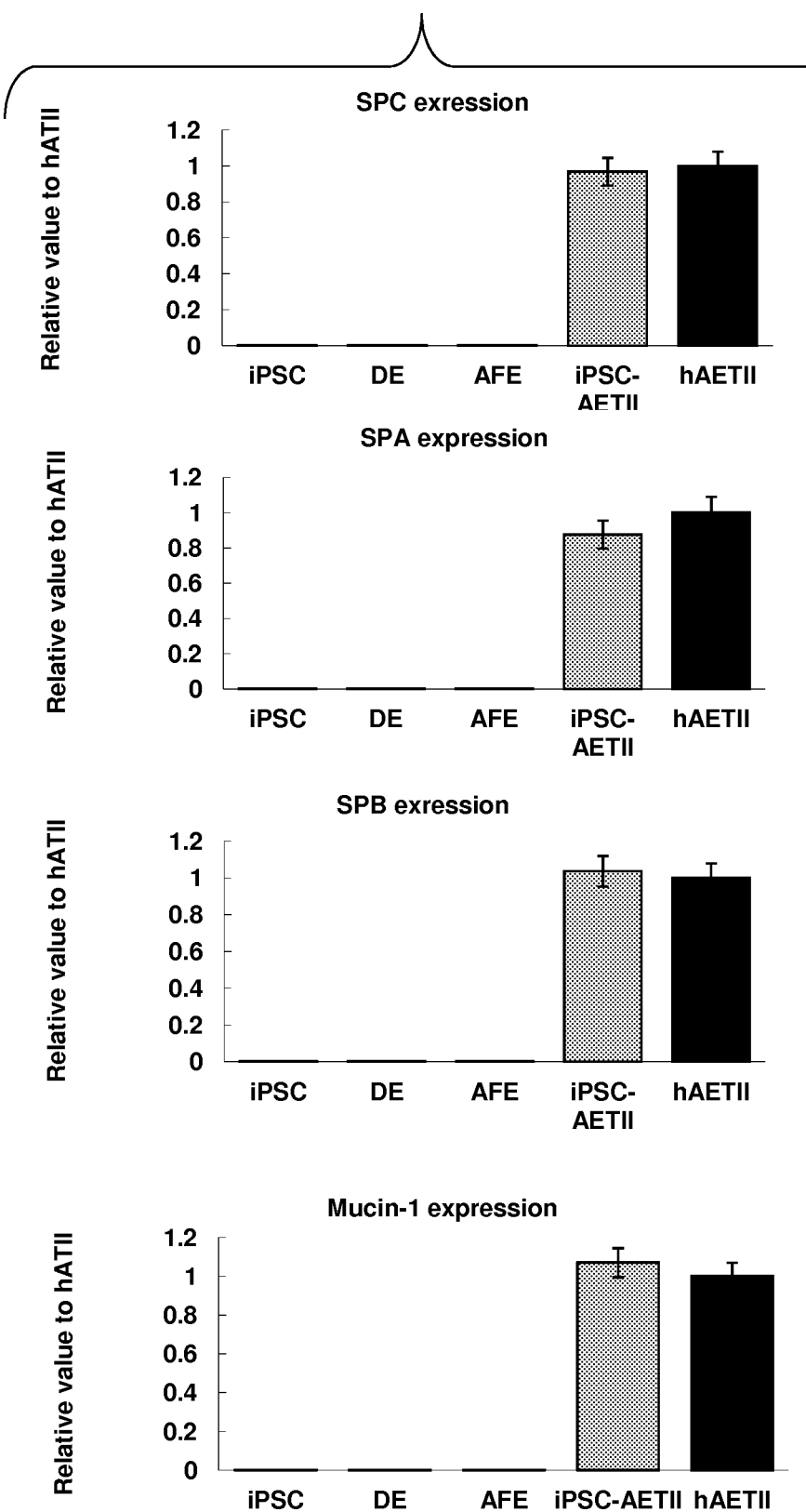
Figure 11H:
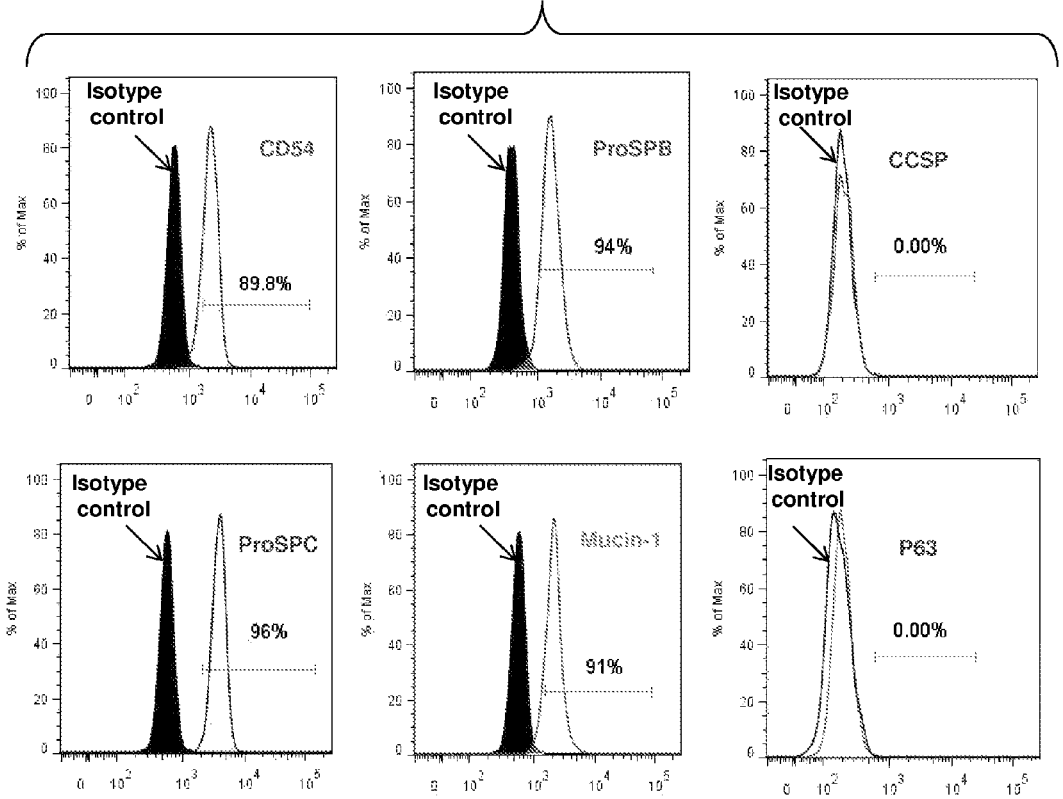
Figure 11I:
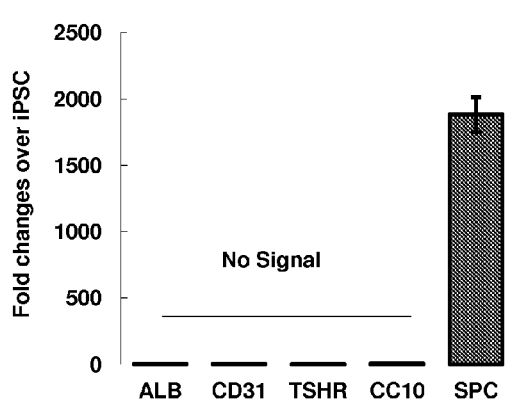
Figure 11J:
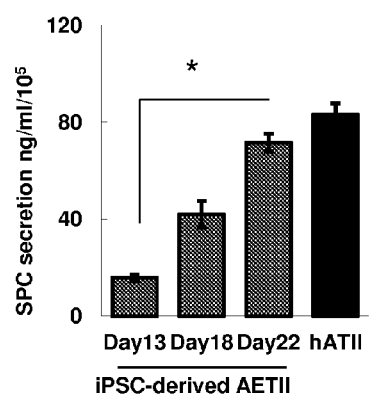

After differentiation to AFE on day 8, the medium was switched to alveolar differentiation medium containing FGF-10, EGF, WNT3a, KGF, and RA for 14 days on human ECM protein. These factors or reagents were chosen through empiric studies, and are thought to play a crucial role in alveolar pneumocyte differentiation and lung development (Longmire T A, et al. 2012. Cell Stem Cell 10(4):398-411, Green M D, et al. 2011. Nat Biotechnol 29(3):267-272, Mou H, et al. 2012. Cell Stem Cell 10(4):385-397, Ali N N, et al. 2002. Tissue Eng 8(4):541-550, Rippon H J, et al. 2006. Stem Cells 24(5):1389-1398, Banerjee E R, et al. 2012. PLoS One 7(3):e33165). Compared with other reports, it was found that the differentiation cocktail that lacked BMP4 in the final stage, resulted in distal markers, especially those associated with type II pneumocytes. After day 22, the cells—now termed AETII cells (FIG. 1A and FIG. 1C)—were maintained in SAGM culture medium containing 1% FBS. AETII cells derived from both the C1 and C2 clones were strongly positive for type II markers, including pro-SPC, pro-surfactant protein B (SPB), mucin-1 and surfactant protein A (SPA). In addition to the positive marker expression associated with type II cells, the presence of lamellar bodies, typical of human type II cells, was also examined by electron microscopy in the iPSC-derived AETII cells. TEM identification of lamellar bodies is used as a method for positively identifying type 2 pneumocytes. The TEM data clearly show the presence of lamellar bodies in the iPSC-derived AETII cells. (FIG. 3A-FIG. 3F, for C1 cells, FIG. 11A-FIG. 11F). Quantitative RT-PCR demonstrated a high percentage of expression of type II cell markers in iPSC-AETII cells, that was comparable to expression levels of freshly isolated human primary alveolar type II cells (hATII cells) (FIG. 3G, for C1 cells, FIG. 11G for C2). Up to 97% of cells were positive for SPC, 92±0.9% positive for Mucin-1, 89±0.9% positive for SPB and the vast majority of the cells, 94±0.9%, expressed the epithelial surface marker CD54 in clone C1 and 96.27±0.5% for SPC, 94.42±0.3% for SPB, and 91.54±1.8% for Mucin-1 and 89.83±0.5% for CD54 in clone C2. Moreover, AETII cells were negative for CCSP (a Clara cell marker), p63 (basal stem cell marker) and SOX2 (proximal airway epithelial cell marker) by FACS analysis, indicating that these cells are a relatively homogeneous population of type II cells (FIG. 3H and FIG. 3I, for C1 cells, FIG. 11H and FIG. 11I for C2). ELISA measurements of SPC protein in the cell culture supernatants indicated that day 13 cells synthesized and secreted SPC at a rate of 16.78 ng/ml and 15.78 ng/ml in C1 and C2 clones, respectively, every 24 h. The rate of secretion was significantly increased on day 22 of differentiation when compared to secretion at day 13 (P<0.05). At day 22, the iPSC-AETII cells from C1 and C2 produced 68.5 ng/ml and 71.5 ng/ml SPC every 24 h, which was comparable to that produced by freshly isolated human AETII cells (82.95 ng/ml) (FIG. 3J, for C1 cells, FIG. 11J for C2).

Figure 3H:
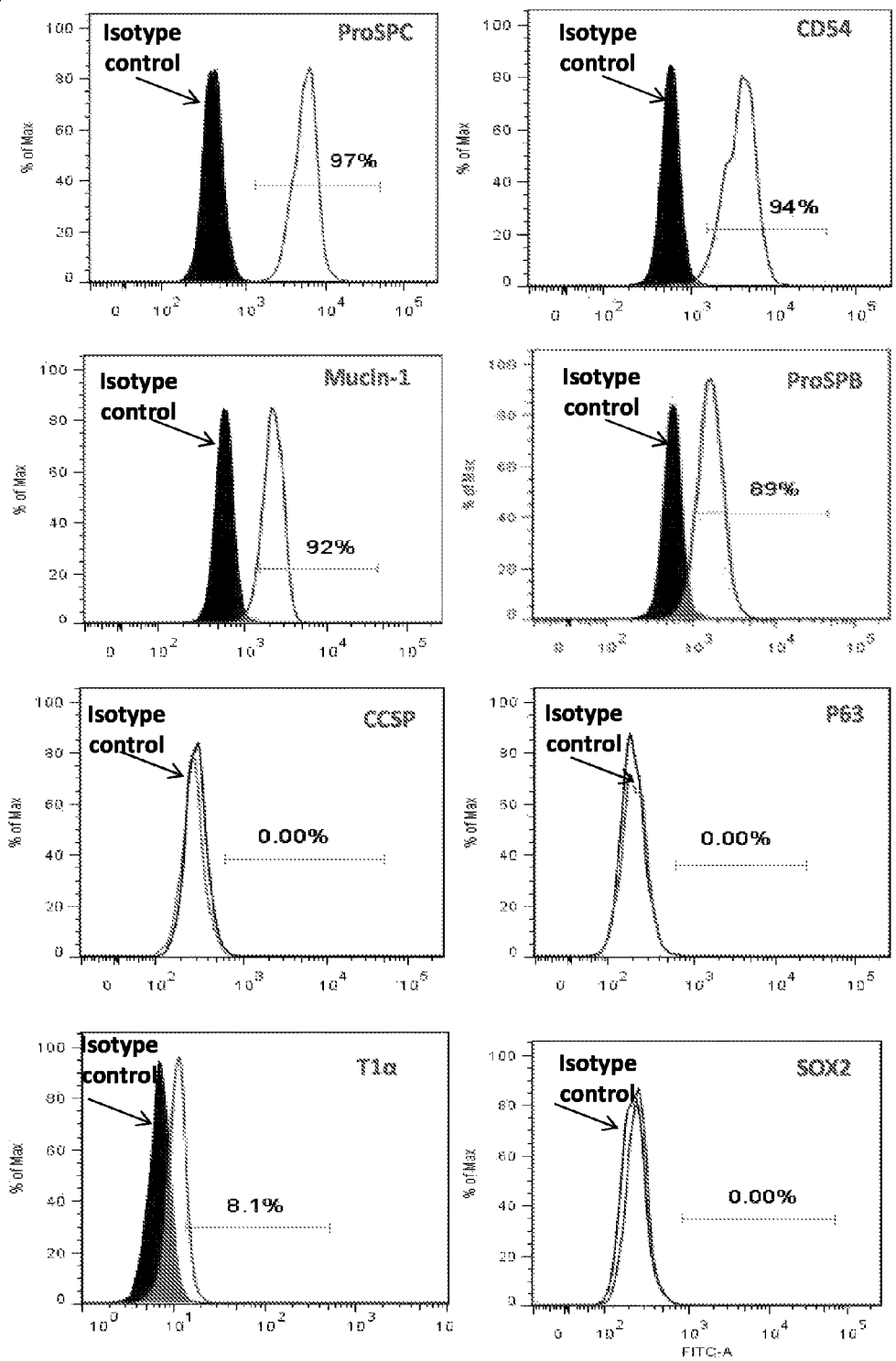

A previous study has found that airway progenitor cells, which ultimately give rise to trachea, bronchus and bronchioles, are NKX2.1$^+$/SOX2$^+$ and sustain high levels of SOX2 expression (Mou H, et al. 2012. Cell Stem Cell 10(4):385-397). However, by day 22, no NKX2.1$^+$/SOX2$^+$ cells or single positive SOX2$^+$ cells were detected in the population of differentiated iPSC-AETII cells. All the AETII cells were also negative for CCSP and p63 as determined by flow cytometry (FIG. 3H for C1 cells, FIG. 11H for C2 cells). This may indicate that these cells are not airway progenitor cells. Since anterior foregut endoderm can be theoretically differentiated into cells expressing markers of thyroid, parathyroid and lung (Longmire T A, et al. 2012. Cell Stem Cell 10(4):398-411), the expression of CD31 (endothelial marker), albumin (mature hepatocyte marker) and TSGHR (thyroid cells marker) were investigated by quantitative RT-PCR, to determine whether the iPSC-AETII cells were contaminated by cells from these other lineages. No specific markers of thyroid, endothelial cells or hepatocyte lineage were detected in iPSC-AETII cells at day 22, thereby confirming the absence of cells from these lineages in the differentiated lung progenitor population (FIG. 3I, for C1 cells, FIG. 11I for C2 cells).

Figure 12C:
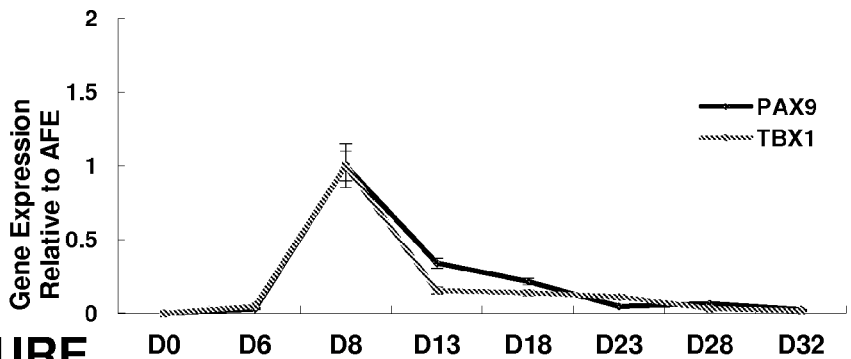
Figure 12D:
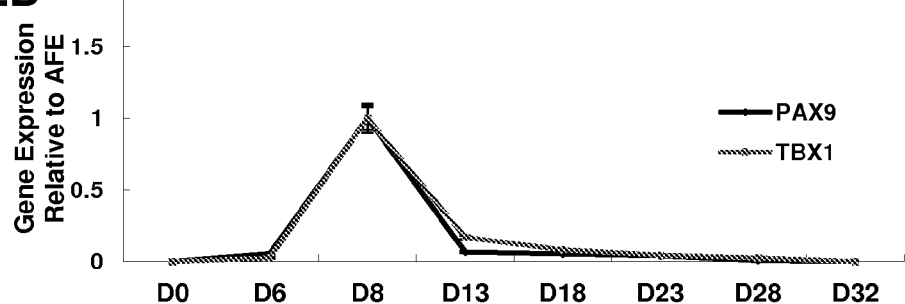
Figure 13A:
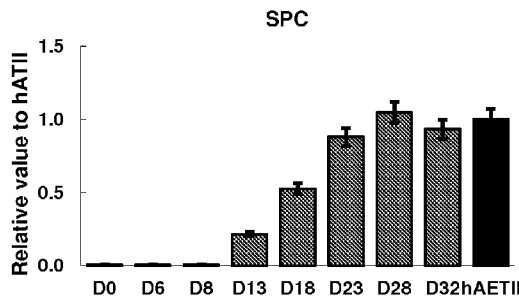
FIG. 13A through FIG. 13D, is a series of images depicting the kinetics of NKX2.1 and SPC expression during differentiation of iPSC cells (C1 clone) to lung alveolar epithelium.
Figure 13B:
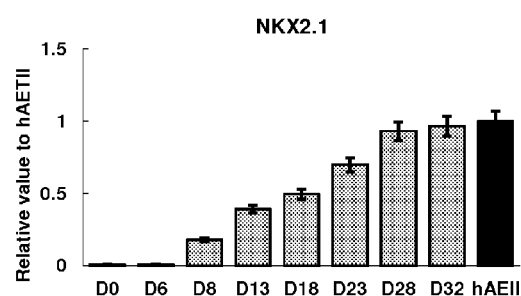
Figure 13C:
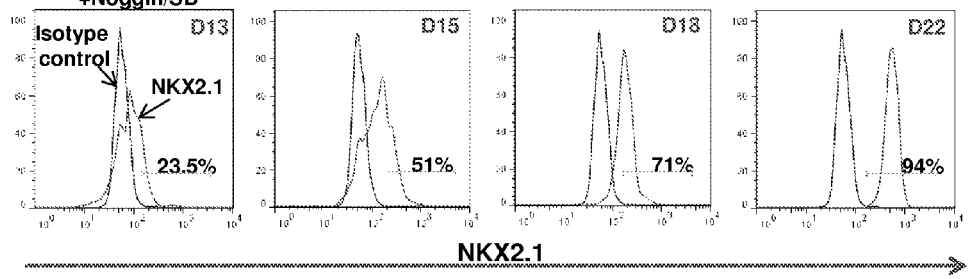
Figure 13D:
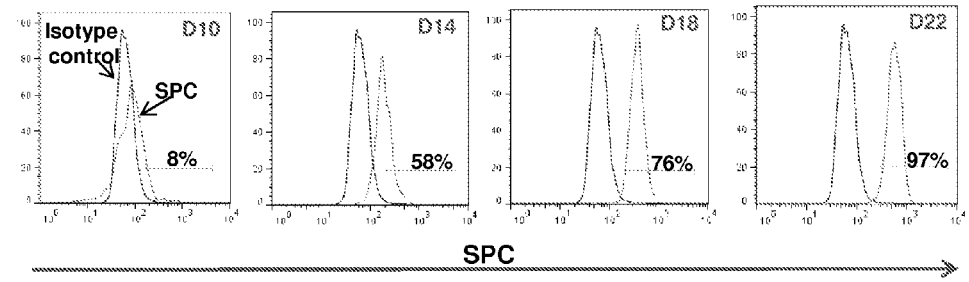
Figure 14A:
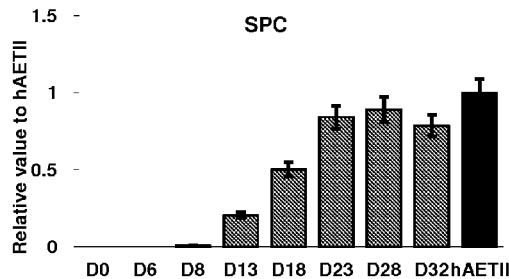
FIG. 14A through FIG. 14D, is a series of images depicting the kinetics of NKX2.1 and SPC expression during differentiation of iPSC cells (C2 clone) to lung alveolar epithelium.
Figure 14B:
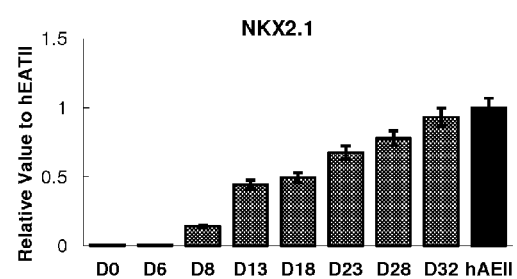
Figure 14C:
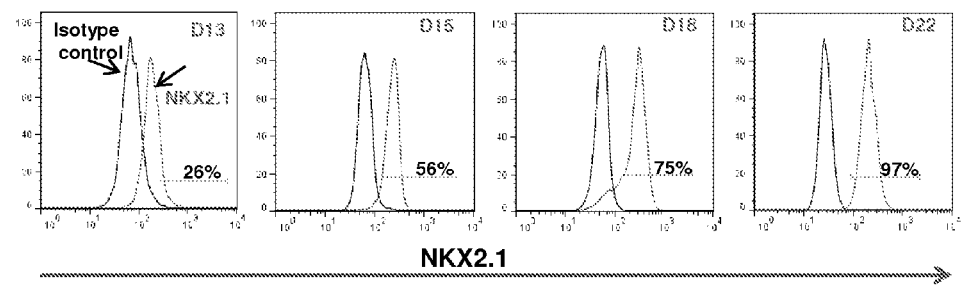
Figure 14D:
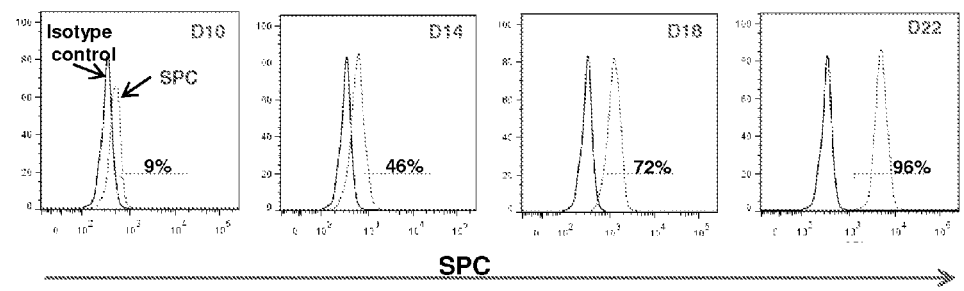
Figure 16A:
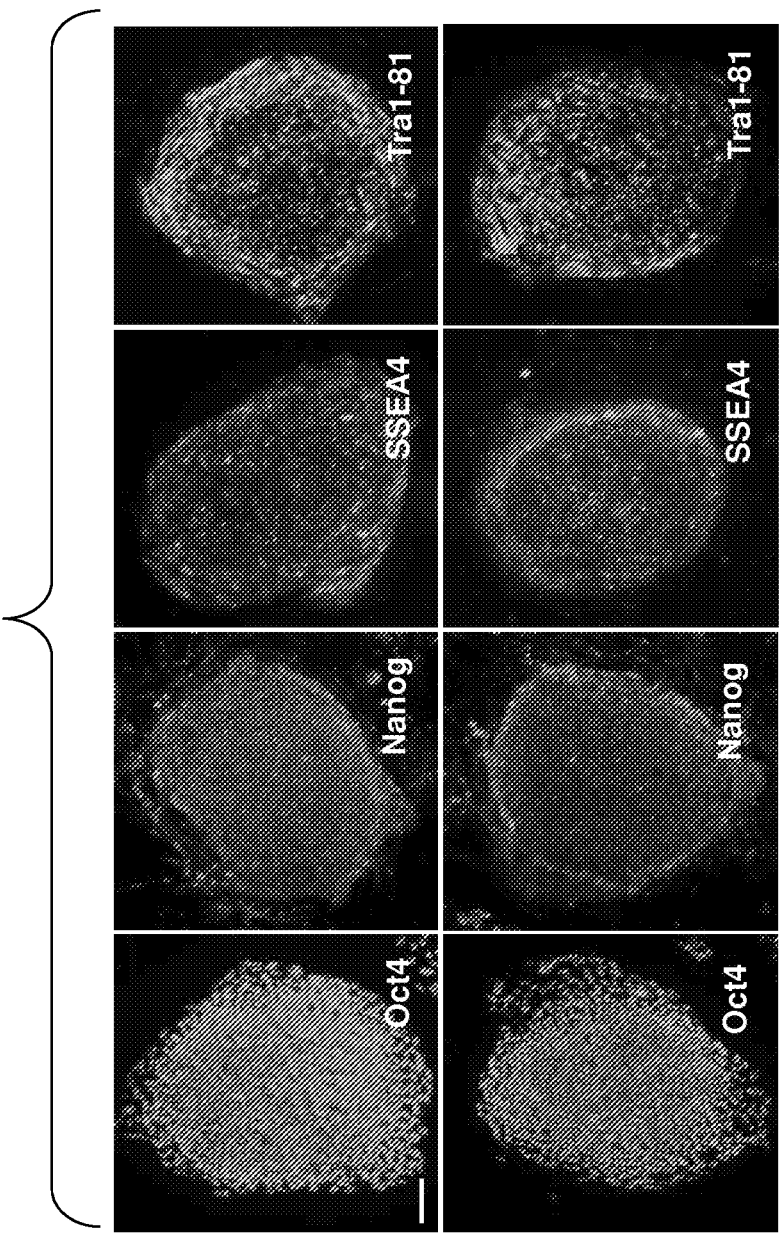
Figure 16B:
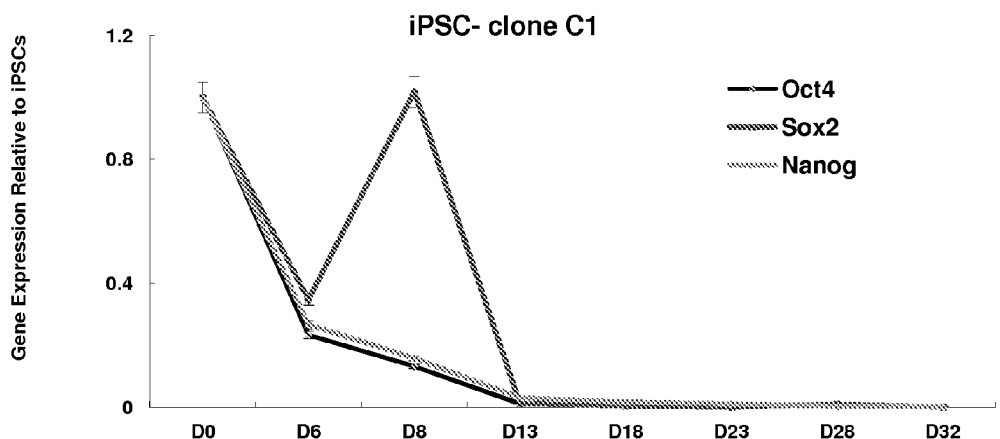
Figure 16C:
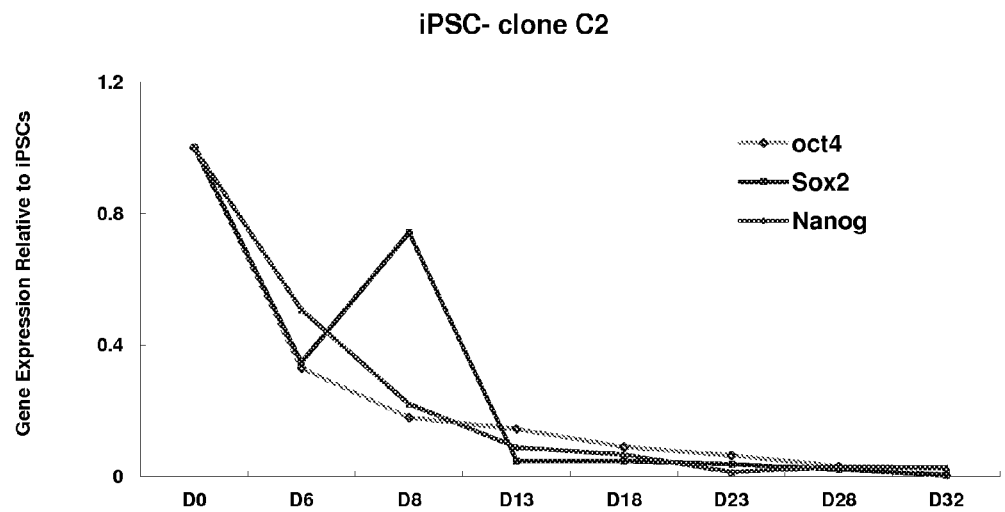

The expression of AFE markers (SOX2, PAX9 and TBX1) and DE markers (SOX17, CXCR4 and FOXA2) decreased from day 8 to day 22. By day 32, none of these markers were detectable in iPSC-AETII cells. In case of FOXA2 and SOX2, after activin A removal at day 6 and switching to NOGGIN/SB-431542 an increase in FOXA2 and SOX2 expression was observed at day 8 followed by a decrease in the expression of these genes in culture over time (FIG. 12A, FIG. 12C, and FIG. 16B for C1 cells, FIG. 12B, FIG. 12D, and FIG. 16CC for C2 cells).

Following exposure to alveolar pneumocyte induction media containing Wnt3a, EGF, KGF and FGF at day 9 of culture, there was lower expression of AFE genes, especially SOX2, and there was a concomitant upregulation of NKX2.1. After day 8, SOX2 was rapidly downregulated while NKX2.1 was upregulated. The expression of NKX2.1 gradually increased from 24±2% at day 13 to 94±0.4% at days 20-22 in C1. Quantitative RT-PCR and flow cytometry revealed that the percentage of SPC positive cells gradually increased from 58±1.6% at day 13 to 90±0.4% at days 20-22 during differentiation in the C1 clone. The same pattern of NKX2.1 and SPC expression was observed in the C2 clone during differentiation from day 8 to day 22. (FIG. 13A-FIG. 13D, for C1 cells, FIG. 14A-FIG. 14D for C2 cells). Between days 8 and 22, NKX2.1$^+$ cells proliferated slowly, ultimately leading to an increase in the number of NKX2.1 and SPC positive cells. The amount of cell death, following the switch in culture medium to alveolar epithelium differentiation medium, was negligible when compared to the earlier medium switch from DE to AFE differentiation medium from day 0 to day 8. Immunostaining for NKX2.1$^+$ cells at different days (day 13, 18 and 21) demonstrated that colonies expressing NKX2.1 were gradually expanded and over-grew the NKX2.1 negative cells. This ultimately led to an increase in the number of NKX2.1 positive cells, as shown by a gradual progression from 24% at day 13 to 94% at days 20-22.

Figure 15A:
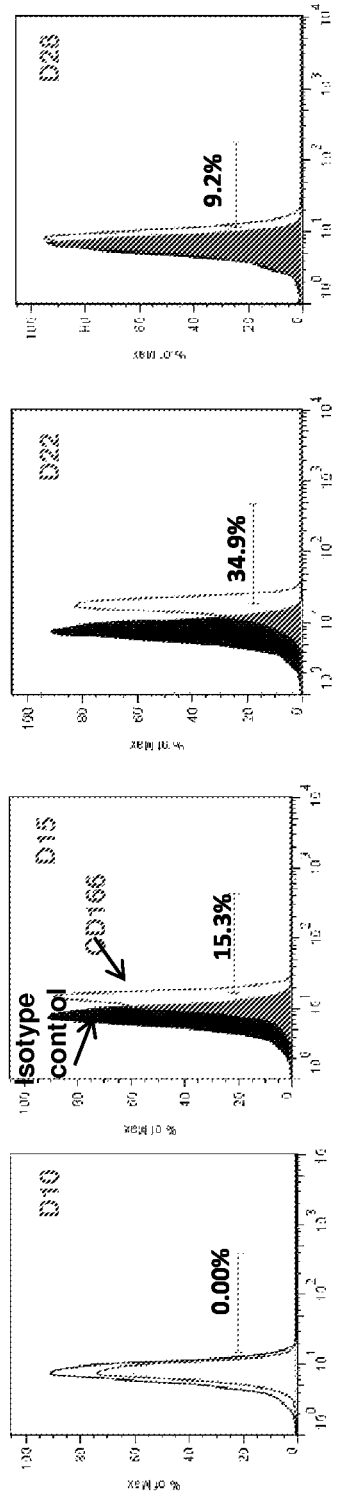
FIG. 15A through FIG. 15D, is a series of images depicting the kinetics of α6β4 and CD166 expression during differentiation of iPSC cells to lung alveolar epithelium.
Figure 15B:
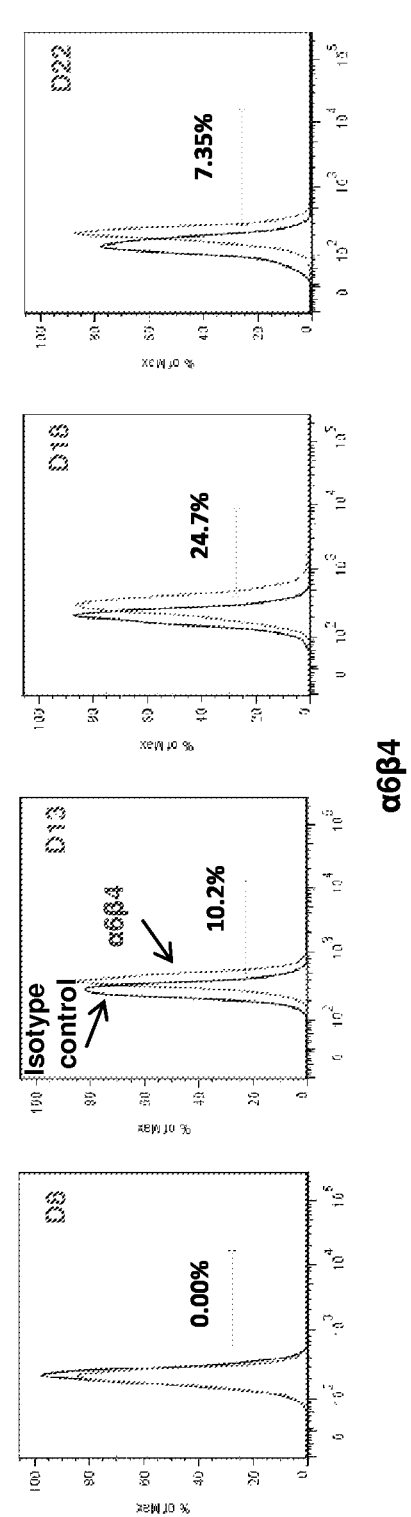
Figure 15C:
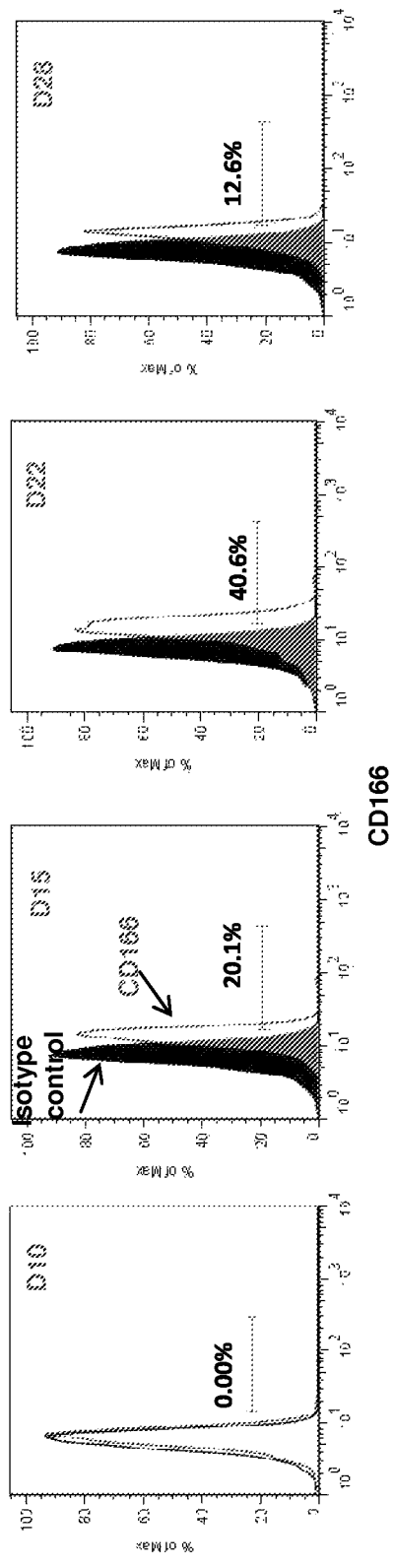
Figure 15D:
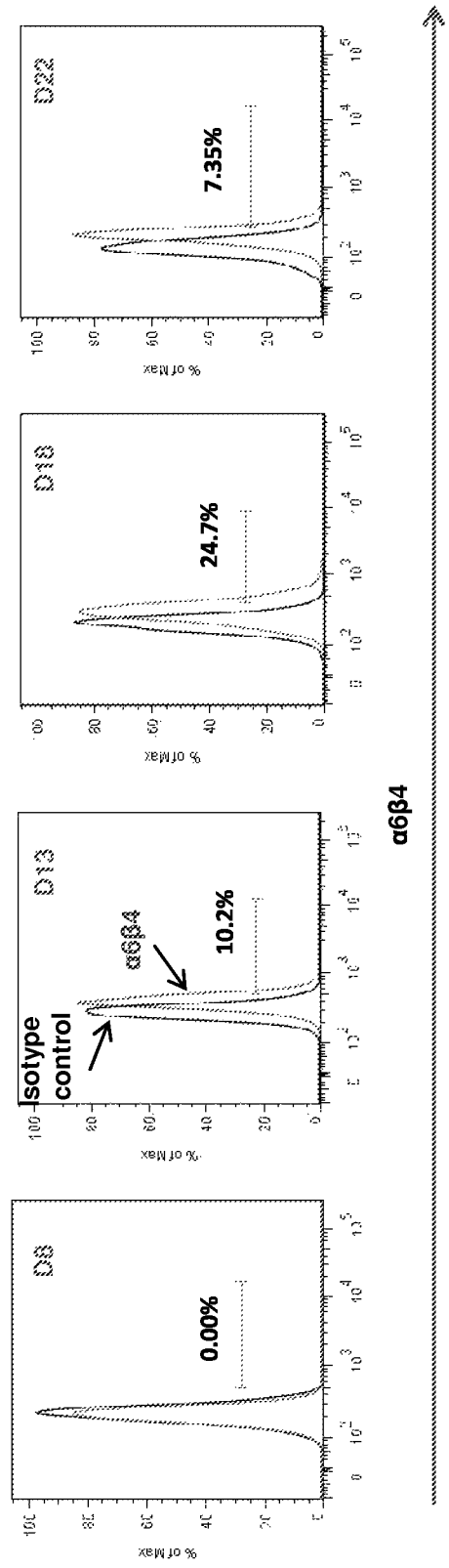

Since several recent studies have reported CD166 and α6β4 to be markers of lung epithelial progenitors (Chapman H A, et al. 2011. *J Clin Invest* 121(7):2855-2862, Whitsett J A, et al. 2011. *J Clin Invest* 121(7):2543-2545, Soh B S, et al. 2012. *Mol Ther* 20(12):2335-2346, Asselin-Labat M L, et al. 2012. *Open Biol* 2:120094), the expression of these markers were characterized during the differentiation of iPSC to epithelial cells at several time points. Flow cytometry revealed that the percentage of CD166 positive cells gradually increased from 15±0.8% at day 13 to 35±1.4% at days 20-22 during differentiation in the C1 clone. The expression of CD166 subsequently decreased in mature cultures of iPSC-derived epithelial cells at day 28. In the case of α6β4, the expression progressively increased from 10±0.7% at day 13 to 25±1.2% at day 18 in C1. By day 22 only 7-8% of the cells were positive for α6β4. The same pattern of CD166 and α6β4 expression was observed in the C2 clone during differentiation from day 8 to day 22. (FIG. 15A and FIG. 15B, for C1 cells, FIG. 15C and FIG. 15D for C2 cells).

Replacing the NOGGIN/SB-431542 media with differentiation media at day 9 of culture resulted in decreasing expression of pluripotency genes such as OCT4 and Nanog over time. As expected, from day 13 to day 22 the pluripotency gene expression was almost undetectable. Flow cytometry on iPSC-derived AETII cells from both clones showed that SPC-positive cells at day 22 were negative for OCT4 (FIG. 16A-FIG. 16E for C1 and C2 cells).

Since type II cells can spontaneously differentiate into cells expressing markers of type I cells (Fehrenbach H, et al. 2001. *Respir Res* 2(1):33-46, Bove P F et al. 2010. *J Biol Chem* 285(45):34939-34949, Fujino N, et al. 2011. *Lab Invest* 91(3):363-37833) the expression of type I markers, T1α, AQ5, and caveolin-1, were assessed by flow cytometry and qPCR. Flow cytometry revealed that 8-11% of cells expressed type I markers following the differentiation protocol. Up to 9% of the cells were positive for AQ5, 9.6% positive for caveolin-1 and 8.1% expressed the type I surface marker T1a in clone C1 (FIG. 4C).

Differentiation of iPSC-Derived AETII to Type I Cells

Figure 4D:
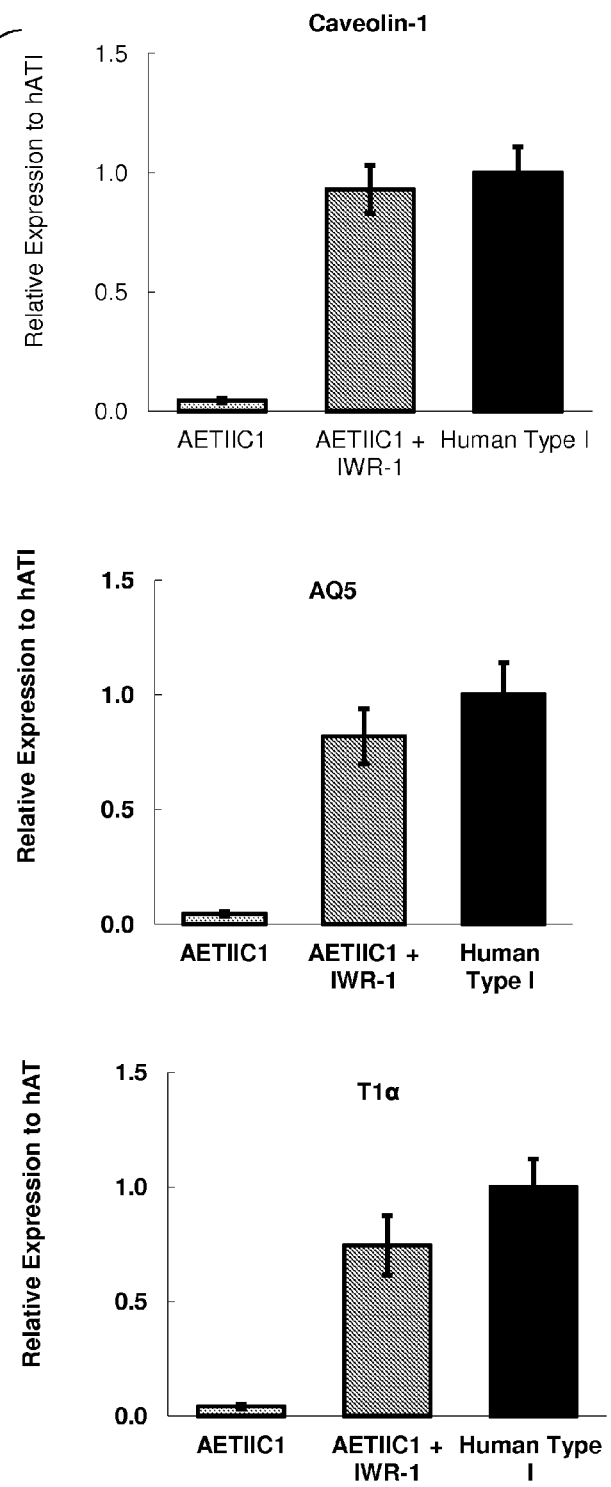

To further differentiate iPSC-AETII to AETI, we next examined the effect of modulating Wnt/β-catenin signaling on type I marker expression in AETII cells. We examined whether the selective β-catenin/CBP inhibitor IWR-1 (Banerjee E R, et al. 2012. *PLoS One* 7(3):e33165, Fehrenbach H, et al. 2001. *Respir Res* 2(1):33-46) would modulate the differentiation of iPSC-AETII cells to AETI cells. Differentiated AETII cells at day 22 were cultured on human ECM protein coated plates in DMEM-10%, FBS supplemented with 100 mM IWR-1 for 7 days. As data from independent experiments indicated, incubation of iPSC-AETII cells with IWR-1 induced the differentiation of AETII cells to the AETI cell phenotype (FIG. 4A-FIG. 4D). Following treatment with IWR-1, there was a significant increase in AETI markers AQ5, T1α and caveolin-1, in iPSCs-derived AETII compared to untreated AETII as determined by immunostaining (FIGS. 4A and 4B). Flow cytometry revealed that up to 92% of cells were positive for aquaporin-5 (AQ5), 98% positive for caveolin-1, and 88% of the cells expressed the epithelial marker T1α (FIG. 4C). In contrast, the AETII cell marker, SPC, decreased significantly as determined by flow cytometry (FIG. 4C). Quantitative RT-PCR demonstrated a high percentage of expression of type I cell markers in iPSC-AETII cells exposed to IWR-1, that was comparable to expression levels of freshly isolated human primary alveolar type I cells (hAETI cells) (FIG. 4D)

Repopulation of Rat and Human Acellular Matrix with iPSC-Derived AETII

To explore the regenerative potential of iPS-derived AETII cells to generate lung tissue in vitro, lungs from adult humans and rats were decellularized by processes that remove cellular components but leave behind a scaffold of extracellular matrix that retains the hierarchical branching structures of airways and vasculature (Petersen T H, et al. 2010. *Science* 329(5991):538-541, Booth A J, et al. 2012. *Am J Resp Crit Care Med.* 186(9): 866-76). This is an assay that was recently developed to test the regenerative potential of primary lung epithelial cells or stem cells derived lung epithelial cells (Longmire T A, et al. 2012. *Cell Stem Cell* 10(4):398-411, Petersen T H, et al. 2010. *Science* 329(5991): 538-541, Daly A B, et al. 2012. *Tissue Eng Part A* 18(1-2): 1-16, Ott H C, et al. 2010. *Nat Med* 16(8):927-933). Both ATI and ATII pneumocytes are differentiated cell types, however several reports have demonstrated that ATII cells retain a level of plasticity. When damage occurs to the ATI pneumocytes, ATII cells proliferate and can, in turn, differentiate into ATI cells (Asselin-Labat M L, et al. 2012. Open Biol 2:120094, Fehrenbach H, et al. 2001. *Respir Res* 2(1):33-46, Fujino N, et al. 2011. *Lab Invest* 91(3):363-37833). Therefore, in the studies presented herein the capacity of iPSC derived type II cells to repopulate the airway compartment of a decellularized lung extracellular matrix was examined. iPSC-AETII cells at day 28 were utilized to repopulate the acellular matrices. This stage seemed most suitable because of their commitment to a pneumocyte type II phenotype and function. The seeded matrix was cultured in a bioreactor that was designed and described previously (Petersen T H, et al. 2010. *Science* 329(5991):538-541, Petersen T H, et al. 2011. *Cell Transplant* 20(7):1117-1126). This bioreactor is capable of replicating key aspects of the in vivo fetal lung environment, including vascular perfusion and liquid ventilation. In addition to seeding iPSC-AETII cells into decellularized whole rat lung tissue, we also seeded iPSC-AETII cells onto slices of either rat or human acellular lung matrix cultured in 6-well plates (FIG. 1C)

For the rat lung bioreactor experiments, approximately 40×10$^6$ cells were injected into the airway through the trachea to repopulate the decellularized rat lung matrix (FIG. 1C). The seeded matrix was then cultured and maintained for up to 7 days in a bioreactor in SAGM (1% FBS). H&E staining showed that iPSC-AETII cells were able to diffusely repopulate alveolar lung structures within distal lung. The majority of seeded AETII cells still showed approximate AETII morphology—a cuboidal shape and round single nuclei (FIG. 5A-FIG. 5C for C1 cells, FIG. 17A-FIG. 17C for C2 cells). Many AETII cells within the lung matrix expressed the type II cell marker, pro-SPC and NKX2.1. In native lung, this marker is normally found on AETII cells. In the reseeded rat lungs, cellular expression of pro-SPC was robust in the alveoli by day 3 and remained present at day 7 (FIG. 5D-5I for C1 cells, FIG. 17D-17I for C2 cells).

It was investigated whether iPSC-derived AETII are able to proliferate in the acellular matrix. After culturing iPSC-AETII cells in the bioreactor, sections from the reseeded lung at day 3 and day 7 were stained for PCNA (proliferating cell nuclear antigen) expression. The majority of cells on the rat scaffold expressed PCNA, at both day 3 and day 7 while they displayed few markers of apoptotic cell death, as determined by immunostaining for caspase-3. However, iPSC-AETII cultured in the rat lung scaffold for 7 days had an increased rate of positive PCNA staining when compared to the day 3 cultures. The data suggest that the iPSC-AETII are able to proliferate when they are seeded in rat scaffold (FIG. 5J-5N for C1 cells, FIG. 17-17M for C2 cells).

Figure 5P:
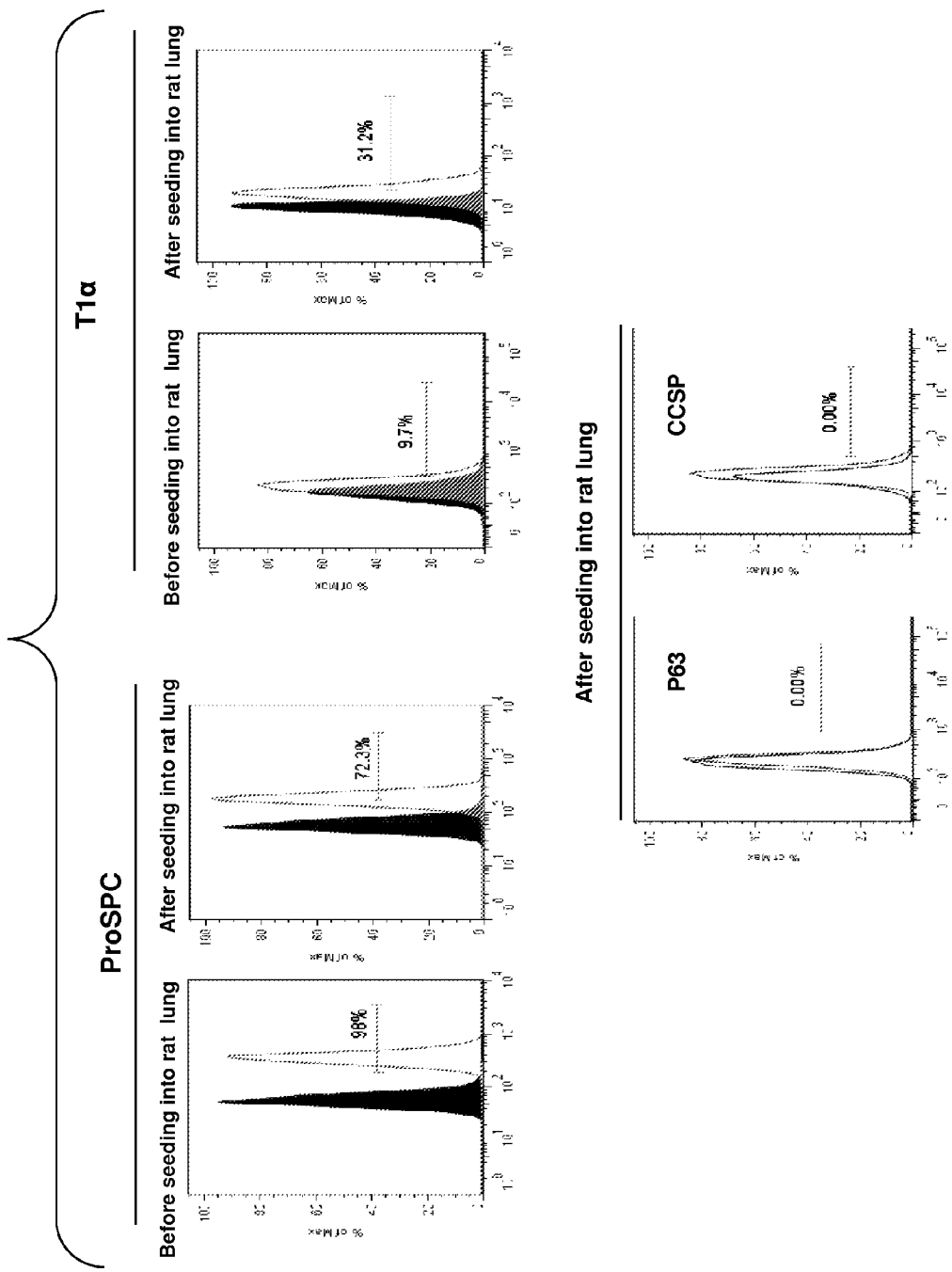

The formation of type 1 cells in vivo, from type II cells, is accompanied by a loss of the NKX 2.1 protein (Longmire T A, et al. 2012. *Cell Stem Cell* 10(4):398-411). Consistent with this pattern, some engrafted AETII cells acquired a flattened morphology, and expressed the type 1 pneumocyte marker T1α but lacked expression of NKX2.1 protein by co-staining (FIG. 5O). Moreover the number of T1α positive cells significantly increased from 9.7% before cell seeding to 31.2% after culturing cells in the rat lung bioreactor. Conversely, the number of SPC positive cells decreased from 98% before cell seeding to 72.3% after 7 days cultured in rat lung scaffold in bioreactor. Since type I cells are terminally differentiated cells and are not able to proliferate like type II cells, These observations may indicate that the extracellular matrix cues support a epithelial populations, and that iPSC-AETII are able to differentiate to type I cells within the lung scaffold. (FIG. 5P). All of the iPSC-AETII cells were negative for CCSP and p63 by FACS analysis after 7 days cultured in the rat lung scaffold (FIG. 5P).

In parallel experiments, iPSC-derived AETII were cultured on sections of rat and human lung matrix. To prepare sections of the acellular lung matrix, lungs from adult donors were treated using a procedure similar to that previously described (Petersen T H, et al. 2010. *Science* 329(5991): 538-541, Booth A J, et al. 2012. *Am J Resp Crit Care Med.* 186(9): 866-76). Then, iPSC-AETII cells were seeded in the acellular matrices by directly pipetting onto sections of the matrix (thickness: 600 μm), and maintaining in culture in 6-well plates in SAGM with 1% FBS. The iPSC-AETII cells adhered well to matrix surfaces and were initially distributed widely throughout alveoli in the matrix, in both the rat and human decellularized lung sections. Many of the cells still showed AETII morphology and there was robust expression of SPC and NKX2.1 (FIG. 6A-FIG. 6F on human lung sections and FIG. 6H-6K on rat lung sections), while some engrafted AETII cells acquired a flattened morphology and expressed the alveolar type I marker, T1α (FIG. 6C on human lung sections and FIG. 6J on rat lung section). iPSC-derived AETII are able to proliferate on both rat and human lung sections, as determined by immunostaining for PCNA and caspase-3 (FIG. 6G on human lung sections and FIG. 6L-FIG. 6O on rat lung section).

As a control for these experiments, isolated human type II cells from adult human lung (hAETII cells) were also seeded onto decellularized human lung sections. As with the iPSC-AETII cells, many of the cells with hAETII morphology expressed SPC and NKX2.1, and some of the hAETII cells gave rise to T1a positive cells (FIG. 6P-FIG. 6U). Moreover they were able to replicate on the human scaffold sections, and the majority of cells expressed PCNA, while they displayed few markers of apoptotic cell death, as determined by immunostaining for caspase-3 (FIG. 6V).

Differentiation of iPSCs Toward DE, AFE, AETII and AETI Cells

Lung epithelia remain among the least-studied lineages to be derived from ESCs and iPSCs in vitro to date, and few research groups have reported on the differentiation toward lung epithelium (Wang D, et al. 2007. *Proc Natl Acad Sci USA.* 104(11):4449-4454, Green M D, et al. 2011. *Nat Biotechnol* 29(3):267-272, Mou H, et al. 2012. *Cell Stem Cell* 10(4):385-397, Van Haute L, et al. 2009. *Respir Res* 10:105). Conditions for directing hESCs or iPSCs to differentiate along an alveolar epithelial lineage with homogeneity are not yet fully defined, and most protocols generate a mixed population of alveolar epithelium from hESCs or iPSCs. In the mouse, a NKX2.1:GFP reporter was used to isolate cells committed to the lung fate which were then amenable to further differentiation (Longmire T A, et al. 2012. *Cell Stem Cell* 10(4):398-411). Moreover, in heterogeneous cultures of differentiating ESCs, induction of late markers of development such as surfactant protein C (SPC) have been reported, but their expression appears to be stochastic, and the cells expressing these markers have been difficult to expand (Longmire T A, et al. 2012. *Cell Stem Cell* 10(4):398-411, Green M D, et al. 2011. *Nat Biotechnol* 29(3):267-272, Mou H, et al. 2012. *Cell Stem Cell* 10(4): 385-397, Ali N N, et al. 2002. *Tissue Eng* 8(4):541-550, Rippon H J, et al. 2006. *Stem Cells* 24(5):1389-1398, Banerjee E R, et al. 2012. *PLoS One* 7(3):e33165). The studies presented herein demonstrate an efficient and consistent, step-wise differentiation method to generate definitive endoderm (DE), anterior foregut endoderm (AFE), and subsequently, a relatively homogeneous population of human alveolar type II cells from two different human iPSCs clones (C1, reprogrammed from fetal lung fibroblasts and C2 reprogrammed from neonatal fibroblasts). Interestingly both iPSC clones yield similar results and had similar efficiency to differentiate toward DE, AFE, AETII and AETI cells, suggesting this protocol can be generalized to other iPSC lines from other sources. Unlike isolated human type II cells, however, these iPSC-AETII cells are capable of proliferating for several passages without losing AETII cell-associated markers, such as SPC, SPA and mucin-1, and can be used to generate tens of millions of cells with which to seed the acellular matrix scaffold. The ability to "scale up" a progenitor population will be particularly valuable when translating these technologies for use in producing human tissues, and allows for the possibility of using autologous iPSC derived cells in future lung bioengineering work.

Under appropriate culture conditions, iPSC-derived AETII cells seeded into either rat decellularized lung bioreactors, or onto decellularized rat or human lung sections, behave similarly to isolated human type II cells. In these studies, the iPSC-AETII cells were able to diffusely repopulate alveolar lung structures. Although the majority of seeded iPSC-AETII cells still showed approximate AETII morphology, the percentages of T1α positive cells increased to approximately 30% within the rat lung matrix over a 7-day culture period. While not wishing to be bound by any particular theory, it is possible that this shift in expression is a differentiating effect of correct cell-matrix interactions. Although type II cells are differentiated cells, these cells nonetheless retain a level of plasticity. Following peripheral lung injury, type II cells undergo proliferation and differentiation toward the type I phenotype. In fact, type II cells are considered to be putative alveolar stem cells and are crucial to the natural regenerative process of the alveoli (Banerjee E R, et al. 2012. *PLoS One* 7(3):e33165, Asselin-Labat M L, et al. 2012. *Open Biol* 2:120094). The interaction between AETII cells and the lung matrix may have been especially impactful since it is likely that the AETII cells are still in a progenitor state able to give rise to T1α cells when they adhere in regions where native lung contains type I cells and maintain a type II cell phenotype in regions where type II cells are typically be found. While not wishing to be bound by any particular theory, since type I cell markers were not detected in the majority of the cells cultured within lung scaffold in bioreactor, it is possible that additional stimuli, such as cyclic stretch or exposure to an air-liquid interface, may be necessary to promote expression of more type I alveolar markers (Gutierrez J A, et al. 1998. *Am J Physiol* 274(2 Pt 1):L196-202, Ostrowski L E, et al. *Expt Lung Res* 21 (6) 957-970, Alcorn D, et al. *J Anat* 123(Pt 3):649-660). Collectively, the data presented herein demonstrate that that in vitro lung regeneration from autologous cells may be a viable strategy for tissue repair and cell therapy applications.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of differentiating a population of stem cells into a population of alveolar epithelial cells, the method comprising: a) inducing a stem cell into a definitive endoderm cell; b) inducing the definitive endoderm cell into an anterior foregut endoderm cell; c) inducing the anterior foregut endoderm cell into an alveolar epithelial cell by culturing the anterior foregut endoderm cell in an alveolar differentiation medium consisting of a basal cell culture medium and one or more growth factors selected from the group consisting of fibroblast growth factor (FGF), basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor (PDGF), vascular endothelial cell growth factor (VEGF), keratinocyte growth factor (KGF), transforming growth factor (TGF), Activin-A, Wnt3a, insulin, growth hormone, erythropoietin, thrombopoietin, interleukin 3 (IL-3), interleukin 6 (IL-6), interleukin 7 (IL-7), macrophage colony stimulating factor, c-kit ligand/stem cell factor, osteoprotegerin ligand, insulin, nerve growth factor, and ciliary neurotrophic factor, wherein the alveolar epithelial cell is not selected using a selectable marker; and d) expanding the alveolar epithelial cell into a population of alveolar epithelial cells, thereby differentiating the population of stem cells into the population of alveolar epithelial cells, wherein at least 95% of alveolar epithelial cells exhibit an alveolar type II phenotype.

2. The method of claim 1, wherein the stem cell is cultured without serum in the presence of Activin A in order to induce the stem cell into the definitive endoderm cell.

3. The method of claim 1, wherein the definitive endoderm cell is cultured in the presence of an extracellular matrix (ECM) protein and a culture medium supplemented with an inhibitor of bone morphogenic protein (BMP) and an inhibitor of transforming growth factor beta (TGF-β) signaling in order to induce the definitive endoderm cell into an anterior foregut endoderm cell.

4. The method of claim 3, wherein the inhibitor of BMP is NOGGIN and the inhibitor of TGF-β signaling is SB-431542.

5. The method of claim 3, wherein the ECM protein is human ECM selected from the group consisting of collagen, laminin, fibronectin, tenascin, elastin, proteoglycan, glycosaminoglycan, and any combination thereof.

6. The method of claim 1, wherein the anterior foregut endoderm cell is cultured in the presence of the alveolar differentiation medium consisting of a basal cell culture medium and a growth factor selected from the group consisting of FGF, EGF, Wnt3a, and KGF in order to induce the anterior foregut endoderm cell into a lung cell wherein the lung cell is an alveolar epithelial type II cell.

7. The method of claim 6, wherein the alveolar type II phenotype is an alveolar epithelial type II progenitor cell phenotype.

8. The method of claim 1, wherein the alveolar type II phenotype is expression of an alveolar type II cell marker selected from the group consisting of surfactant protein C (SPC), Mucin-1, surfactant protein B (SPB), CD54, and any combination thereof.

9. The method of claim 1, wherein the alveolar epithelial cell is cultured on a decellularized lung matrix.

* * * * *

SEQUENCE LISTING

<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized

<400> SEQUENCE: 1
tccaagccac actccacga                                                  19

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized

<400> SEQUENCE: 2
ttcctctgga ttccttggg                                                  19

<210> SEQ ID NO 3
<211> LENGTH: 19
<212> TYPE: DNA
<213> ORGANISM: Artificial Sequence
<220> FEATURE:
<223> OTHER INFORMATION: Chemically synthesized

<400> SEQUENCE: 3
tgggagccga tgacctatg                                                  19

<210> SEQ ID NO 4
<211> LENGTH: 19
<212> TYPE: DNA
<213> ORGANISM: Artificial Sequence
<220> FEATURE:
<223> OTHER INFORMATION: Chemically synthesized

<400> SEQUENCE: 4
gcctccttgg ccatcttgt                                                  19

<210> SEQ ID NO 5
<211> LENGTH: 19
<212> TYPE: DNA

<213> ORGANISM: Artificial Sequence
<220> FEATURE:
<223> OTHER INFORMATION: Chemically synthesized

<400> SEQUENCE: 5
ggacgtgagc aagaacatg                                                  19

<210> SEQ ID NO 6
<211> LENGTH: 19
<212> TYPE: DNA
<213> ORGANISM: Artificial Sequence
<220> FEATURE:
<223> OTHER INFORMATION: Chemically synthesized

<400> SEQUENCE: 6
tcgctccagc tcgtacacc                                                  19

<210> SEQ ID NO 7
<211> LENGTH: 21
<212> TYPE: DNA
<213> ORGANISM: Artificial Sequence
<220> FEATURE:
<223> OTHER INFORMATION: Chemically synthesized

<400> SEQUENCE: 7
ccttcttatc gtggtggtgg t                                               21

<210> SEQ ID NO 8
<211> LENGTH: 22
<212> TYPE: DNA
<213> ORGANISM: Artificial Sequence
<220> FEATURE:
<223> OTHER INFORMATION: Chemically synthesized

<400> SEQUENCE: 8
tctccgtgtg tttctggctc at                                              22

<210> SEQ ID NO 9
<211> LENGTH: 21
<212> TYPE: DNA
<213> ORGANISM: Artificial Sequence
<220> FEATURE:
<223> OTHER INFORMATION: Chemically synthesized

<400> SEQUENCE: 9
agcttctact ctggtgcaca a                                               21

<210> SEQ ID NO 10
<211> LENGTH: 18
<212> TYPE: DNA
<213> ORGANISM: Artificial Sequence
<220> FEATURE:
<223> OTHER INFORMATION: Chemically synthesized

<400> SEQUENCE: 10
ggtggctggg aattgaga                                                   18

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized

<400> SEQUENCE: 11
cctcacttca ctgcactgta                                                 20

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized

<400> SEQUENCE: 12
caggttttct ttccctagct                                            20

<210> SEQ ID NO 13
<211> LENGTH: 19
<212> TYPE: DNA
<213> ORGANISM: Artificial Sequence
<220> FEATURE:
<223> OTHER INFORMATION: Chemically synthesized

<400> SEQUENCE: 13
cccagcagac ttcacatgt                                             19

<210> SEQ ID NO 14
<211> LENGTH: 20
<212> TYPE: DNA
<213> ORGANISM: Artificial Sequence
<220> FEATURE:
<223> OTHER INFORMATION: Chemically synthesized

<400> SEQUENCE: 14
cctcccattt ccctcgtttt                                            20

<210> SEQ ID NO 15
<211> LENGTH: 21
<212> TYPE: DNA
<213> ORGANISM: Artificial Sequence
<220> FEATURE:
<223> OTHER INFORMATION: Chemically synthesized

<400> SEQUENCE: 15
ccaaattctc ctgccagtga c                                          21

<210> SEQ ID NO 16
<211> LENGTH: 22
<212> TYPE: DNA
<213> ORGANISM: Artificial Sequence
<220> FEATURE:
<223> OTHER INFORMATION: Chemically synthesized

<400> SEQUENCE: 16
cacgtggttt ccaaacaaga aa                                         22

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized

<400> SEQUENCE: 17
ccctggtcac actggctctc                                            20

<210> SEQ ID NO 18
<211> LENGTH: 20
<212> TYPE: DNA
<213> ORGANISM: Artificial Sequence
<220> FEATURE:

<223> OTHER INFORMATION: Chemically synthesized

<400> SEQUENCE: 18
tcataactgg agggtgtgtc                                                   20

<210> SEQ ID NO 19
<211> LENGTH: 19
<212> TYPE: DNA
<213> ORGANISM: Artificial Sequence
<220> FEATURE:
<223> OTHER INFORMATION: Chemically synthesized

<400> SEQUENCE: 19
caccgcatct ggagaacca                                                    19

<210> SEQ ID NO 20
<211> LENGTH: 21
<212> TYPE: DNA
<213> ORGANISM: Artificial Sequence
<220> FEATURE:
<223> OTHER INFORMATION: Chemically synthesized

<400> SEQUENCE: 20
gcccatttcc tcggtgtagt t                                                 21

<210> SEQ ID NO 21
<211> LENGTH: 18
<212> TYPE: DNA
<213> ORGANISM: Artificial Sequence
<220> FEATURE:
<223> OTHER INFORMATION: Chemically synthesized

<400> SEQUENCE: 21
gggagcggtg aagatgga                                                     18

<210> SEQ ID NO 22
<211> LENGTH: 22
<212> TYPE: DNA
<213> ORGANISM: Artificial Sequence
<220> FEATURE:
<223> OTHER INFORMATION: Chemically synthesized

<400> SEQUENCE: 22
tcatgttgct cacggaggag ta                                                22

<210> SEQ ID NO 23
<211> LENGTH: 18
<212> TYPE: DNA
<213> ORGANISM: Artificial Sequence
<220> FEATURE:
<223> OTHER INFORMATION: Chemically synthesized

<400> SEQUENCE: 23
ggcgcagcag aatccaga                                                     18

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized

<400> SEQUENCE: 24
ccacgacttg cccagcat                                                     18

<210> SEQ ID NO 25
<211> LENGTH: 21
<212> TYPE: DNA
<213> ORGANISM: Artificial Sequence
<220> FEATURE:
<223> OTHER INFORMATION: Chemically synthesized

<400> SEQUENCE: 25
gttatgttgc tggacatggg t                                          21

<210> SEQ ID NO 26
<211> LENGTH: 22
<212> TYPE: DNA
<213> ORGANISM: Artificial Sequence
<220> FEATURE:
<223> OTHER INFORMATION: Chemically synthesized

<400> SEQUENCE: 26
gaagccgtga cagaatgact ac                                         22

<210> SEQ ID NO 27
<211> LENGTH: 19
<212> TYPE: DNA
<213> ORGANISM: Artificial Sequence
<220> FEATURE:
<223> OTHER INFORMATION: Chemically synthesized

<400> SEQUENCE: 27
gctcctacga ctattgccc                                             19

<210> SEQ ID NO 28
<211> LENGTH: 19
<212> TYPE: DNA
<213> ORGANISM: Artificial Sequence
<220> FEATURE:
<223> OTHER INFORMATION: Chemically synthesized

<400> SEQUENCE: 28
cgtattcctt gcttgccct                                             19

<210> SEQ ID NO 29
<211> LENGTH: 24
<212> TYPE: DNA
<213> ORGANISM: Artificial Sequence
<220> FEATURE:
<223> OTHER INFORMATION: Chemically synthesized

<400> SEQUENCE: 29
attgcagtgg ttatcatcgg agtg                                       24

<210> SEQ ID NO 30
<211> LENGTH: 24
<212> TYPE: DNA
<213> ORGANISM: Artificial Sequence
<220> FEATURE:
<223> OTHER INFORMATION: Chemically synthesized

<400> SEQUENCE: 30
ctcgttgttg gagttcagaa gtgg                                       24

<210> SEQ ID NO 31
<211> LENGTH: 20
<212> TYPE: DNA
<213> ORGANISM: Artificial Sequence
<220> FEATURE:
<223> OTHER INFORMATION: Chemically synthesized

```
<400> SEQUENCE: 31
tttcttaccc aagccactgc                                                  20

<210> SEQ ID NO 32
<211> LENGTH: 21
<212> TYPE: DNA
<213> ORGANISM: Artificial Sequence
<220> FEATURE:
<223> OTHER INFORMATION: Chemically synthesized

<400> SEQUENCE: 32
ttctcttcat attcctggtg g                                                21

<210> SEQ ID NO 33
<211> LENGTH: 21
<212> TYPE: DNA
<213> ORGANISM: Artificial Sequence
<220> FEATURE:
<223> OTHER INFORMATION: Chemically synthesized

<400> SEQUENCE: 33
aaacgccagt aagtgacaga g                                                21

<210> SEQ ID NO 34
<211> LENGTH: 21
<212> TYPE: DNA
<213> ORGANISM: Artificial Sequence
<220> FEATURE:
<223> OTHER INFORMATION: Chemically synthesized

<400> SEQUENCE: 34
atatctgcat ggaaggtgaa t                                                21

<210> SEQ ID NO 35
<211> LENGTH: 23
<212> TYPE: DNA
<213> ORGANISM: Artificial Sequence
<220> FEATURE:
<223> OTHER INFORMATION: Chemically synthesized

<400> SEQUENCE: 35
gacaacagcc tcaagatcat cag                                              23

<210> SEQ ID NO 36
<211> LENGTH: 23
<212> TYPE: DNA
<213> ORGANISM: Artificial Sequence
<220> FEATURE:
<223> OTHER INFORMATION: Chemically synthesized

<400> SEQUENCE: 36
atggcatgga ctgtggtcat gag                                              23
```